US006297014B1

(12) United States Patent
Taylor et al.

(10) Patent No.: US 6,297,014 B1
(45) Date of Patent: Oct. 2, 2001

(54) GENETIC TEST TO DETERMINE NON-RESPONSIVENESS TO STATIN DRUG TREATMENT

(75) Inventors: Kent D. Taylor, Santa Paula; Maren T. Scheuner, Manhattan Beach; Jerome I. Rotter, Los Angeles; Huiying Yang, Cerritos, all of CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 0 days.

(21) Appl. No.: 09/347,114

(22) Filed: Jul. 2, 1999

(51) Int. Cl.$^7$ .............................. C12Q 1/68; C07H 21/04

(52) U.S. Cl. ........................ 435/6; 536/23.1; 536/23.5; 536/24.1; 536/24.3; 536/24.33

(58) Field of Search .................................. 536/23.1, 23.5, 536/24.1, 24.33, 24.3; 435/6

(56) References Cited

U.S. PATENT DOCUMENTS

| | | | |
|---|---|---|---|
| 4,683,195 | 7/1987 | Mullis et al. | 435/6 |
| 4,683,202 | 7/1987 | Mullis | 435/6 |
| 4,988,617 | 1/1991 | Landegren | 435/6 |
| 5,384,242 | 1/1995 | Oakes | 435/6 |

OTHER PUBLICATIONS

Anguita, M. et al., Comparison of the effectiveness of lovastatin therapy for hypercholesterolemia after heart transplantation between patients with and without pretransplant atherosclerotic coronary artery diseases, Am. J. Cardiol, 74(8):776–779 (Oct. 15, 1994).
Alván, Gunnar, Editorial, Genetic polymorphisms in drug metabolisn, Journal of Internal Medicine, vol. 231, pp. 571–573, (1992).
Ballantyne, C. M., Low–density lipoproteins and risk for coronary artery disease, Am. J. Cardiol., 82(9A):3Q–12Q (Nov. 5, 1998).
Bell, D. S., A comparison of lovastatin, and HMG–CoA reductase inhibitor, with gemfibrozil, a fibrinic acid derivative, in the treatment of patients with diabetic dyslipidemia, Clin. Ther, 17(5):901–910 (Sep. 1995) Abstract Only.
Bellosta, S. et al., HMG–CoA reductase inhibitors reduce MMP–9 secretion by macrophages, Arterioscler Thromb Vasc Biol, 18(11):1671–8 (Nov. 1998).
Butowski, P.F. et al., Usual care dietary practice, achievement and implications for medication in the management of hypercholesterolaemia. Data from the U.K. Lipid Clinics Programme., Eur Heart J., 19(9):1328–33 (Sep. 1998).
Campeau, Lucien et al., The Relation of Risk Factors to the Development of Atherosclerosis in Saphenous–vein Bypass Grafts and the Progression of Disease in the Native Circulation, The New England Journal of Medicine, vol. 311, No. 21, pp. 1329–1332 (Nov. 22, 1984).

Campeau, Lucien et al., The Effect of Aggressive Lowering of Low–Density Lipoprotein Cholesterol Levels and Low-–Dose Anticoagulation on Obstructive Changes in Saphenous–vein Coronary–Artery Bypass Grafts, The New England Journal of Medicine, vol. 336, No. 3, pp. 153–162 (Jan. 16, 1997).
Cannon, C. P., Advances in the medical management of acute coronary syndromes, Curr Opin Cardiol, 13(5):327–47 (Sep 1998). Abstract Only.
Chen, L. et al., HindIII DNA polymorphism in the lipoprotein lipase gene and plasma lipid phenotypes and carotid artery atherosclerosis, Hum Genet, 98(5):551–556 (Nov. 1996).
Chuat, J. C. et al., The lipoprotein lipase–encoding human gene: sequence from intron–6 to intron–9 and presence in intron–∂of a 40–million–year–old Alu sequence, Gene, 110(2):257–61 (Jan. 15, 1992). Abstract Only.
Clark A. G. et al., Haplotype structure and population genetic inferences from nucleotide–sequence variation in human lipoprotein lipase, Am J. Hum Genet, 63(2):595–612 (Aug 1998).
Deeb, Samir S., et al., Structure of the Human Lipoprotein Lipase Gene, Biochemistry, vol. 28, No. 10, pp. 4131–4135 (May 16, 1989).
Durrington, P. N., Can we afford to treat hyperlipidaemia as we should? Strategies for rational treatment, Atherosclerosis, 139 Suppl 1:S1–5 (Sep 1998). Abstract Only.
Farmer, J. A. et al., Currently available hypolipidaemic drugs and future therapeutic developments, Bailieres Clin Endocrinol Metab, 9(4):825–847 (Oct. 1995).
Farmer, J. A. et al., Choosing the right lipid–regulating agent. A guide to selection, Drugs, 52(5):649:661 (Nov 1996).
Farmer, J. A., Economic implications of lipid–lowering trials: current considerations in selecting a statin, Am J. Cardiol, 82(6A):26M–31M (Sep. 24, 1998).
Farmer, J. A., Aggressive lipid therapy in the statin era, Prog Cardiovasc Dis, 41(2):71–94 (Sep.–Oct. 1998).

(List continued on next page.)

Primary Examiner—Lisa B. Arthur
Assistant Examiner—Jeanine Goldberg
(74) Attorney, Agent, or Firm—Sidley Austin Brown & Wood

(57) ABSTRACT

In a method for detecting a genetic predisposition in a human for non-responsiveness to statin drug treatment for coronary artery disease, nucleic acids comprising nucleotide sequences of the human lipoprotein lipase (LPL) gene are amplified and analyzed. Homozygosity for a variant allele in a non-coding or untranslated region of the 3' end of LPL, for example, LPL HindIII 2/2 or (TTTA)$_n$ 4/4 genotypes, is linked to non-responsiveness to treatment with statin drugs, including lovastatin, pravastatin, simvastatin, atorvastatin, fluvastatin, or cerivastatin. Oligonucleotide primer sequences, primer sets, and genetic testing kits allow the practitioner to practice the method and thus better individualize the treatment and improve the care of patients with coronary artery disease.

55 Claims, 2 Drawing Sheets

OTHER PUBLICATIONS

Farnier, M. et al., Current and future treatment of hyperlipidemia: the role of statins, *Am J. Cardiol*, 82(4B):3J–10J (Aug. 27, 1998).

Fisher, R. M. et al., Common variation in the lipoprotein lipase gene: effects on plasma lipids and risk of atherosclerosis, *Atherosclerosis*, 135(2):145–59 (Dec. 1997). Abstract Only.

Funke Harald et al., The low down on lipoprotein lipase, *Nature Genetics*, vol. 10, pp. 6–7 (May 1995).

Garg, A. et al., Lovastatin for lowering cholesterol levels in non–insulin–dependent diabetes mellitus, *N Engl J Med*, 318(2):81–86 (Jan. 1998).

Gerdes, C. et al., Polymorphisms in the lipoprotein lipase gene and their associations with plasma lipid concentrations in 40–year–old Danish men, *Circulation*, 92(7):1765–1769 (Oct. 1995).

Goldberg, R. et al., Comparison of the effects of lovastatin and gemfibrozil on lipids and glucose control in non–insulin–dependent diabetes mellitus, *Am J Cardiol*, 66(8):16B–21B (Sep. 18, 1990).

Guyton, J. R., et al., Effectiveness of once–nightly dosing of extended–release niacin alone and in combination for hypercholesterolemia, *Am J Cardiol*, 82(6):737–43 (Sep. 15, 1998).

Gylling, H. et al., Treatment of lipid disorders in non–insulin–dependent diabetes mellitus, *Curr Opin Lipidl*, 8(6):342–7 (Dec. 1997).

Hansson, L. et al., Effects of intensive blood–pressure lowering and low–dose aspirin in patients with hypertension: principal results of the Hypertension Optimal Treatment (Hot) randomised trial. Hot Study Group, *Lancet*, 351(9118):1755–62 (Jun. 13, 1998).

Hayden, M. R. et al., Molecular genetics of human lipoprotein lipase deficiency, *Mol Cell Biochem*, 113(2):171–176 (Aug. 18, 1992).

Heizmann, Camilla et al., DNA polymorphism haplotypes of the human lipoprotein lipase gene: possible association with high density lipoprotein levels, *Human Genetics*, vol. 86, pp. 578–584 (1991).

Humphries, S. E. et al., Lipoprotein lipase gene variation is associated with a paternal history of premature coronary artery disease and fasting and postprandial plasma triglycerides: the European Atherosclerosis Research Study (EARS), *Arterioscler Throm Vasc Biol*, 18(4):526–34 (Apr. 1998).

Huse, D. M. et al., Cost–effectiveness of statins, *Am J. Cardiol*, 82(11):1357–63 (Dec. 1, 1998).

Jukema, J. Wouter et al., The $Asp_9$ Asn Mutation in the Lipoprotein Lipase Gene is Associated with Increased Progression of Coronary Atherosclerosis, *Circulation*, vol. 94, No. 8, pp. 1913–1918 (Oct. 15, 1996).

Kirchgessner, Todd G. et al., The sequence of cDNA Encoding Lipoprotein Lipase, *The Journal of Biological Chemistry*, vol. 262, No. 18, pp. 8463–8466 (Jun. 25, 1987).

Kirchgessner, T. G. et al., Organization of the human lipoprotein lipase gene and evolution of the lipase gene family, *Proc Natl Acad Sci USA*, vol. 86, No. 24, pp. 9647–9651 (Dec. 1989).

Kleyn, Patrick W. et al., Genetic Variation as a Guide to Drug Development, *Science*, vol. 281, pp. 1820–1821 (Sep. 18, 1998).

Kornitzer, M., Primary and secondary prevention of coronary artery disease: a follow–up on clinical controlled trials, *Curr Opin Lipidol*, 9(6):557–64 (Dec. 1998). Abstract Only.

Kozaki, K. et al., Mutational analysis of human lipoprotein lipase by carboxy–terminal truncation, *J Lipid Res*, 34(10):1765–1772 (Oct. 1993). Abstract Only.

Kuivenhoven, Jan Albert et al., The role of a Common Variant of the Cholesteryl Ester Transfer Protein Gene in the Progression of Coronary Atherosclerosis, *The New England Journal of Medicine*, vol. 338, No. 2, pp. 86–93 (Jan. 8, 1998).

LaRosa, J. C., The role of diet and exercise in the statin era, *Prog Cardiovasc Dis*, 41(2):137–50 (Sep.–Oct. 1998).

McKenney, J. M., Lovastatin: a new cholesterol–lowering agent, *Clin Pharm*, 7(1):21–36 (Jan. 1988).

Mori, A. et al., Development of a direct DNA sequencing method for detecting heterozygous mutations of the human lipoprotein lipase gene, *Clin Biochem*, 30(4):315–324, (Jun. 1997). Abstract Only.

Neitzel, Gary F. et al. Atherosclerosis in Aortocoronary Bypass Grafts, Morphologic Study and Risk Factor Analysis 6 to 12 Years After Surgery, *Arteriosclerosis*, vol. 6, No. 6, pp. 594–600 (Nov./Dec. 1986).

Nickerson, Deborah A. et al., DNA sequence diversity in a 9.7–kb region of the human lipoprotein lipase gene, *Nature Genetics*, vol. 19, No. 3, pp. 233–240 (Jul. 1998).

Oka, Kazuhiro et al., Structure and polymorphic map of human lipoprotein lipase gene, *Biochimica et Biophysica Acta*, vol. 1049, pp. 21–26 (1990).

Olsson, A. G., Addressing the challenge, *Eur Heart J*, 19 Suppl M: M29–35 (Oct. 1998).

Peacock, Rachel E. et al., Associations between lipoprotein lipase gene polymorphisms and plasma correlations of lipids, lipoproteins and lipase activities in young myocardial infarction survivors and age–matched healthy individuals from Sweden, *Atherosclerosis*, vol. 97, pp. 171–185 (1992).

Pedersen, T. R. et al., Benefits and risks of HMG–CoA reductase inhibitors in the prevention of coronary heart disease: a reappraisal, *Drug Saf*, 14(1):11–24 (Jan. 1996). Abstract Only.

Pitsavos, C. E. et al., Effects of pravastatin on thoracic aortic atherosclerosis in patients with heterozygous familial hypercholesterolemia, *Am J Cardiol*, 82(12):1484–8 (Dec. 15, 1998).

Reymer, P. W. et al., A lipoprotein lipase mutation (Asn291Ser) is associated with reduced HDL cholesterol levels in premature atherosclerosis, *Nat Genet*, 10(1):28–34 (May 1995).

Rifkind, B. M., Clinical trials of reducing low–density lipoprotein concentrations, *Endocrinol Metab Clin North Am*, 27(3):585–95, viii–ix (Sep 1998). Abstract Only.

Rudski, L. et al., Systemic immune reactions to HMG–CoA reductase inhibitors. Report of 4 cases and review of the literature, *Medicine (Baltimore)*, 77(6):378–83 (Nov. 1998). Abstract Only.

Santamarina–Fojo, Silvia et al., Structure, function and role of lipoprotein lipase in lipoprotein metabolism, *Genetics and Molecular Biology, Current Opinion in Lipidology*, vol. 5, pp. 117–125 (1994).

Sass, C. et al., Evidence for a cholesterol–lowering gene in a French–Canadian kindred with familial hypercholesterolemia, *Hum Genet*, 96(1):21–26 (Jul. 1995).

Scheen, A. J., [Drug clinics. Drug of the month. Atorvastatin], *Rev Med Liege*, 53(6):374–7 (Jun. 1998). Abstract Only.

Szucs, T.D., Pharmaco–economic aspects of lipid–lowering therapy: is it worth the price?, *Eur Heart J*, 19 Suppl M:M22–8 (Oct. 1998).

Tikkanen, M. J. et al., Treatment of familial and non–familial hypercholesterolaemia: a review of HMG–CoA reductase inhibitors and probucol, *Eur Heart J*, 8 Suppl E: 97–101 (Aug. 1987). Abstract Only.

The Medical Research Council's General Practice Research Framework, Thrombosis prevention trial: randomised trial of low–intensity oral anticoagulation with warfarin and low–dose aspirin in the primary prevention of ischaemic heart disease in men at increased risk. The Medical Research Council's General practice Research Framework, *Lancet*, 351(9098):233–41 (Jan. 24, 1998).

Vesell, Elliot S., Therapeutic Lessons from Pharmacogenetics, *Annals of Internal Medicine*, vol. 126, No. 8, pp. 653–655 (Apr. 15, 1997).

von Keutz, E. et al., Preclinical safety evaluation of cerivastatin, a novel HMG–CoA reductase inhibitor, *Am J. Cardiol*, 82(4B):11J–17J (Aug. 27, 1998).

Weinshilboum, Richard, Methyltransferase Pharmacogenetics, *Pharmac Ther*, vol. 43, pp. 77–90 (1989).

Wheller, D. C., Are there potential non–lipid–lowering uses of statins?, *Drugs*, 56(4):517–22 (Oct. 1998).

Wion, Karen L. et al., Human Lipoprotein Lipase complementary DNA Sequence, *Science*, vol. 235, pp. 1638–1641 (Mar. 27, 1987).

Zuliani, Giovanni et al., Tetranucleotide repeat polymorphism in the LPL gene, Department of Molecular Genetics, University of Texas Southwestern Medical Center, 5323 Harry Hines Boulevard, Dallas, TX 75235 USA (1990).

Ahn, Y. I. Et al., Two DNA polymorphisms in the lipoprotein lipase gene and their associations with factors related to cardiovascular disease, *J Lipid Res*, 34*3):421–8 (Mar. 1993). Abstract Only.

Chamberlain, J.C. et al., DNA polymorphisms at the lipoprotein lipase gene: associations in normal and hypertriglyceridaemic subjects, *Atherosclerosis*, 79(1):85–91 (Sep. 1989).

Georges, J. L. et al., Family study of lipoprotein lipase gene polymorphisms and plasma triglyceride levels, *Genet Epidemiol*, 13(2):179–92 (1996).

Mitchell, R. J. et al., DNA polymorphisms at the lipoprotein lipase gene and their association with quantitative variation in plasma high–density lipoproteins and triacylglycerides, *Hum Biol*, 66(3):383–97 (Jun. 1994). Abstract Only.

Minnich A. et al., Lipoprotein lipase gene mutations in coronary artery disease, *Can J. Cardiol*, 14(5):711–6 (May 1998). Abstract Only.

Algret et al "Effect of hypolipidemic drugs on key enzyme activities related to lipid metabolism in normolipidemic rabbits" Eur. J. of Pharmacology, vol. 347, pp. 283–291, Apr. 1998.*

Christians et al "Metabolism and Drug Interactions of 3–Hydroxy–3–Methylglutaryl Coenzyme A reductase inhibitors in Transplant Patients: Are the Statins mechanistically similar?" Pharmacology, vol. 80, No. 1 pp. 1–35, 1998.*

Glock et al "Allelic ladder characterization of the short tandem repeats polymorphisms in intron 6 of the lipoprotein lipase gene and its application in an austrian caucasian population study" J. of Forensic Sciences, vol. 41, No. 4, pp. 579–581, Jul. 1996.*

Takagi et al "Identification of two new alleles at the LPL STR locus results in seven polymorphic allels in the Japanes population" Molecular and Cellular Probes, vol. 10, pp. 227–228, 1996.*

Chaut et al "The lioprotein lipase–encoding human gene" Gene, vol. 110, pp. 257–261, Jan. 1992.*

Gotoda et al "Detection of three separate DNA polymorphisms in the human LPL gene by gene amplification and restriction endonuclease digestion" J. of Lipid Research, vol. 33, No. 7, pp. 1067–1072, 1992.*

Paulweber et al "Molecular basis of lipoprotein lipase deficiency in two Austrian families with type I hyperlipoproteinemia" Artherosclerosis, vol. 86, No. 2–3, pp. 239–250, Feb. 1991.*

Stratagene Catalog, p. 38, 1988.*

Schoonjans et al "3–Hydroxy–3–methylglutaryl CoA reductase inhibitors reduce serum triglyceride levels through modulation of apolipoprotein C–III and lipoprotein lipase" FEBS Letters, VOI 452, No. 3, pp. 160–164, Jun. 1999.*

* cited by examiner

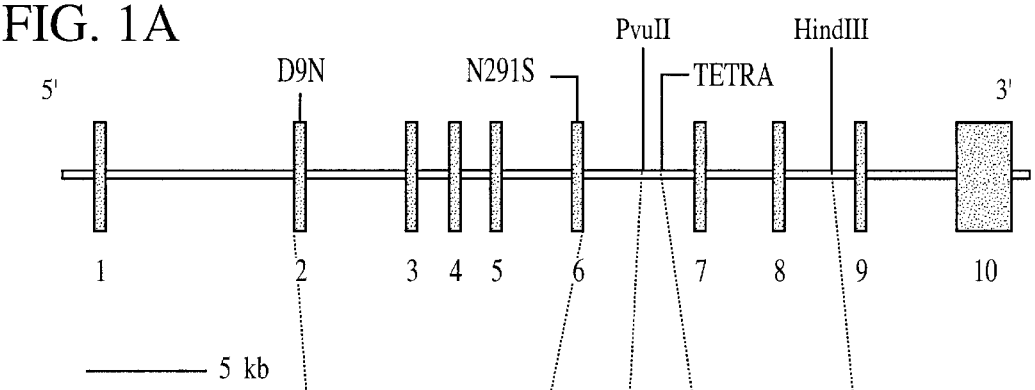
FIG. 1A
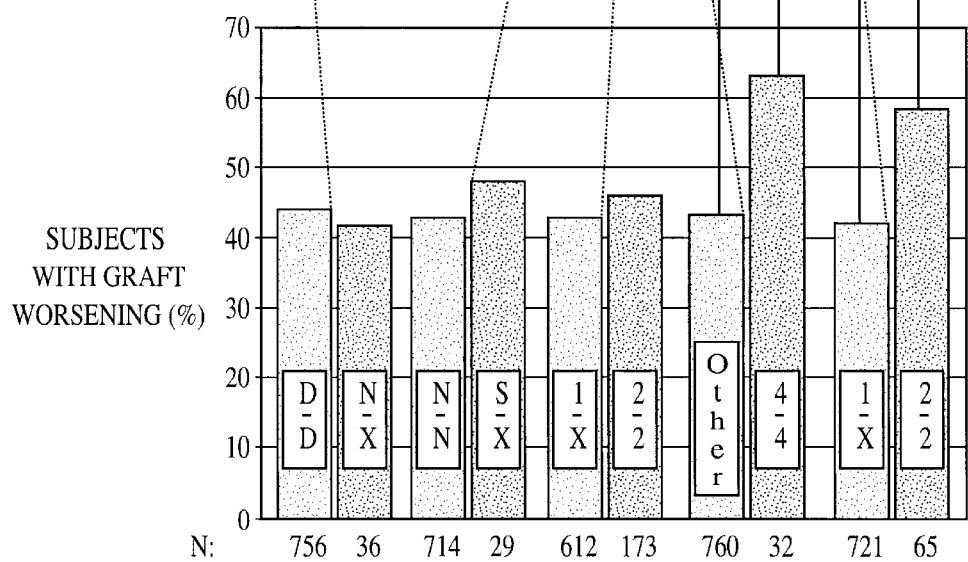
FIG. 1B
FIG. 1C

GENETIC TEST TO DETERMINE NON-RESPONSIVENESS TO STATIN DRUG TREATMENT

BACKGROUND OF THE INVENTION

Throughout this application various publications are referenced within parentheses. The disclosures of these publications in their entireties are hereby incorporated by reference in this application in order to more fully describe the state of the art to which this invention pertains.

1. The Field of the Invention

This invention relates to the medical arts. In particular, it relates to the field of genetic testing methods and diagnostic kits.

2. Discussion of the Related Art

Statin drugs—the most potent lipid-lowering agents currently available—are 3-hydroxy-3-methylglutaryl coenzyme A (HMG-CoA) reductase inhibitors. They include lovastatin, pravastatin, simvastatin, atorvastatin, fluvastatin, and cerivastatin. All these statin drugs share a common mechanism of action and have similar toxicity profiles. (E. von Kreutz and G. Schluter, Preclinical safety evaluation of cerivastatin, a novel HMG-CoA reductase inhibitor, Am. J. Cardiol. 82(4B):11J–17J [1998]; A. G. Ollson [1998]).

The statin drugs are effective in reducing the primary and secondary risk of coronary artery disease and coronary events, such as heart attack, in middle-aged and older men and women (under 76 years), in both diabetic and non-diabetic patients, and are often prescribed for patients with hyperlipidemia. (A. G. Ollson, Addressing the challenge, Eur. Heart J. Suppl. M:M29–35 [1998]; M. Kornitzer, Primary and secondary prevention of coronary artery disease: a follow-up on clinical controlled trials, Curr. Opin. Lipidol. 9(6):557–64 [1998]; M. Farnier and J. Davignon, Current and future treatment of hyperlipidemia: the role of statins, Am. J. Cardiol. 82(4B):3J–10J[1998]). Statins used in secondary prevention of coronary artery or heart disease significantly reduce the risk of stroke, total mortality and morbidity and attacks of myocardial ischemia; the use of statins is also associated with improvements in endothelial and fibrinolytic functions and decreased platelet thrombus formation. (M. Kornitzer [1998]; M. Farnier and J. Davignon, Current and future treatment of hyperlipidemia: the role of statins, Am. J. Cardiol. 82(4B):3J–10J [1998]).

The use of statin drugs has recently decreased the need for surgical coronary revascularization, known as coronary artery bypass graft (CABG). (B. M. Rifkind, Clinical trials of reducing low-density lipoprotein concentrations. Endocrinol. Metab. Clin. North Am. 27(3):585–95, viii-ix [1998]). But CABG is still a common surgical intervention for patients who develop atherosclerotic occlusion in coronary arteries. Approximately 12,000–14,000 CABG procedures are performed annually. (G. F. Neitzel et al., Atherosclerosis in Aortocoronary Bypass Grafts, Atherosclerosis 6(6):594–600 [1986]). The patient's own saphenous vein, or brachial or mammary artery, is used to bypass the affected coronary artery. The majority of CABG patients experience good long-term results, but 30–40% require a second CABG within 10–12 years after surgery, and continuing atherosclerosis in the graft is an important factor in late graft failure. (L. Campeau et al., The effect of aggressive lowering of low-density lipoprotein cholesterol levels and low-dose anticoagulation on obstructive changes in saphenous-vein coronary-artery bypass grafts, N. Eng. J. Med. 336(3):153–62 [1997]).

Atherosclerosis in bypass grafts is associated with elevated serum levels of very low density lipoproteins (VLDL), low density lipoprotein cholesterol (LDL-C), and triglycerides, and low levels of high density lipoprotein cholesterol (HDL-C). (J. T. Lie et al., Aortocoronary bypass saphenous vein atherosclerosis: Anatomic study of 99 vein grafts from normal and hyperlipoproteinemic patients up to 75 months postoperatively, Am. J. Cardiol. 40:906 [1977]; L. Campeau et al, The relation of risk factors to the development of atherosclerosis in saphenous vein bypass grafts and the progression of disease in the native circulation, N. Eng. J. Med. 311(21): 1329–32 [1984]). It is standard for CABG patients to be prescribed statin drugs to lower their serum LDL-C.

Lipid lowering therapy has been demonstrated to delay the progression of atherosclerosis in coronary arteries. (E.g., G. Brown et al., Regression of coronary artery disease as a result of intensive lipid lowering therapy in men with high levels of apolipoprotein B, N. Engl. J. Med. 323:1289–98 [1990]; J. P. Kane et al., Regression of coronary atherosclerosis during treatment of familial hypercholesterolemia with combined drug regimens, JAMA 264:3007–12 [1990]; Jukema et al., 1995). Prior to the Post-CABG Trial, few data were available to determine the efficacy of LDL-lowering therapy to delay the obstruction of saphenous-vein grafts. (D. H. Blankenhorn et al., Beneficial effects of combined colestipol-niacin therapy on coronary atherosclerosis and coronary venous bypass grafts, JAMA 257:3233–40 [1987]). Furthermore, thrombosis had also been observed to contribute to graft obstruction (G. F. Neitzel et al., Atherosclerosis in aortocoronary bypass grafts. morphologic study and risk factor analysis 6 to 12 years after surgery, Arteriosclerosis 6:594–600 [1986]). Low-dose anticoagulation therapy prevented emboli after major surgery (A. G. G. Turpie et al., Randomised comparison of two intensities of oral anticoagulant therapy after tissue heart valve replacement, Lancet 1:1242–45 [1988]; L. Poller et al., Fixed minidose warfarin: a new approach to prophylaxis against venous thrombosis after major surgery, Br. Med. J. 295:1309–12 [1987]), and this implied that low-dose anticoagulation treatment would also be able to delay graft obstruction.

Statin drug treatment beneficially affects the long-term outcome for most CABG patients. In a large clinical study, the Post-CABG Trial, CABG patients received statin drug treatment to lower serum LDL-C; in comparing patients who had received aggressive lovastatin treatment (LDL-C lowered to 93–97 mg/dl) to those who had only received moderate lovastatin treatment (LDL-C lowered to 132–136 mg/dl), the percentages of patients with atherosclerotic worsening of grafts within 4 years were 39% and 51%, respectively,. (L. Campeau et al. [1997]). The number of patients in the aggressive lovastatin-treatment group who required a second CABG procedure was 29% lower than the number in the moderate-treatment group.

In addition to serum lipid concentrations, there are other risk factors, that may have a genetic basis, and that may independently affect atherosclerotic coronary artery disease and occlusion of bypass grafts or that interact with statin treatment to lower serum lipids, which can affect atherosclerotic stenosis. Several laboratories have observed a link between variant alleles of the lipoprotein lipase gene (LPL) and the occurrence and/or progression of atherosclerosis. The involvement of LPL in coronary artery disease was suspected, since rare homozygotes for defects in this gene have type I hyperlipoproteinemia (OMIM 238600) and premature coronary artery disease. (P. Benlian et al., Premature atherosclerosis in patients with familial chylomicronemia caused by mutations in the lipoprotein lipase gene. N. Engl. J. Med. 335:848–54 [1996]).

Lipoprotein lipase (LPL; E.C. 3.1.1.34), also known as triacylglycerol acylhydrolase, is a heparin-releasable glycoprotein enzyme bound to glycosaminoglycan components of macrophages and to the luminal surface of capillary epithelial cells in a variety of human tissues, including heart, skeletal muscle, adipose, lung, and brain. (K. L. Wion et al., Human lipoprotein lipase complementary DNA sequence, Science 235:1638 [1987]; C. Heizmann et al., DNA polymorphism haplotypes of the human lipoprotein lipase gene: possible association with high density lipoprotein levels, Hum. Genet. 86:578–84 [1991]). Lipoprotein lipase is active as a dimer of identical subunits, each approximately 62,500 D in unglycosylated form. (M. R. Taskinen et al., Enzymes involved in triglyceride hydrolysis. In: James Shepard (Ed.), Bailliere's Clinical Endocrinology and Metabolism, Vol. 1, No.3, Bailliere Tindall, London, pp.639–66 [1987]).

Lipoprotein lipase is the rate-limiting enzyme for the hydrolysis and removal of triglyceride-rich lipoproteins, such as chylomicrons, VLDL, and LDL-C from the blood stream. (Jukema et al., The $Asp_9Asn$ Mutation in the Lipoprotein Lipase Gene Is Associated With Increased Progression of Coronary Atherosclerosis, Circulation 94(8):1913–18 [1996]). The enzymatic action of LPL results in the generation of mono- and diglycerides and free fatty acids that can be used as fuel for energy or reesterified for storage in peripheral adipose tissue.

The gene sequence of human LPL is known, including the 3' region through exon 10 and the 3' untranslated region (3'-UTR). (K. L. Wion et al., Human lipoprotein lipase complementary DNA sequence, Science 235:1638–41 [1987]; T. G. Kirchgessner et al., The sequence of cDNA encoding lipoprotein lipase, J. Biol. Chem. 262(18):8463–66 [1987]; K. Oka et al., Structure and polymorphic map of human lipoprotein lipase gene. Biochim. Biophys. Acta 1049:21–26 [1990]; D. A. Nickerson et al., DNA sequence diversity in a 9.7-kb region of the human lipoprotein lipase gene, Nat. Genet. 19:233–40 [1998]). Nickerson et al. sequenced the region of the LPL gene spanning exons 4–9 (containing the major catalytic portion of the enzyme) of 71 individuals taken from 3 different populations and observed 88 different DNA variants or polymorphisms, with 78 of these present at an allele frequency greater than 1% (D. A. Nickerson et al., [1998]).

Two LPL polymorphisms are known to affect LPL activity. The D9N mutation in exon 2 has been associated with increased triglyceride levels and with the occurrence of coronary atherosclerosis, attenuating the ability of pravastatin to lower LDL-C. (J. Jukema et al. [1996]). The N291S mutation in exon 6 has been associated with reduced HDL-C levels. (P. Reymer et al., A lipoprotein lipase mutation [asn291ser] is associated with reduced HDL cholesterol levels in premature atherosclerosis, Nat. Gen. 10:28–34 [1995]; H. H. Wittrup et al., A common substitution [asn291ser] in lipoprotein lipase is associated with increased risk of ischemic heart disease, J. Clin. Inves. 99:1606–13 [1997]). The N291S mutation is also linked with increased coronary stenosis (narrowing of arterial lumen) seen on angiography in women with verified ischemic heart disease compared to controls. (H. H. Wittrup et al. [1997]).

Two other LPL polymorphisms have demonstrated association with the development of atherosclerosis, although their functional significance is unknown. The first is the PvuII polymorphism in intron 6, which is linked with the number of coronary blood vessels with greater than 50% obstruction. (X. Wang et al., Common DNA polymorphisms at the lipoprotein lipase gene: association with severity of coronary artery disease and diabetes, Circulation 93:1339–45 [1996]). The second is the HindIII polymorphism in intron 8, associated with the angiographic severity of coronary artery disease. (R. Mattu et al., DNA variants at the LPL gene locus associate with angiographically defined severity of atherosclerosis and serum lipoprotein levels in a Welsh population, Arterio. Thromb. 14:1090–97 [1994]; R. Peacock et al., Associations between lipoprotein lipase, lipoproteins and lipase activities in young myocardial infarction survivors and age-matched healthy individuals from Sweden, Atherosclerosis 97:171–85 [1992]).

Progress in pharmacogenetics has shown that human genetic variation underlies different individual responses to drug treatment within a population. (Reviewed in G. Alvan, Genetic polymorphisms in drug metabolism, J. Int. Med. 231:571–73 [1992]; P. W. Kleyn and E. S. Vesell, Genetic variation as a guide to drug development, Science 281:1820–22 [1998]). For example, alleles of the NAT1 and NAT2 genes (N-Acetyltransferases) create a "slow acetylator" phenotype in 40–60% of Caucasians, resulting in a slow clearance and associated toxicity of many drugs including isoniazid and procainamide (K. P. Vatsis et al., Diverse point mutations in the human gene for polymorphic N-acetyltransferase, Proc. Natl. Acad. Sci. USA 88(14):6333–37 [1991]). A defect in CYP2D6 (a member of the cytochrome P450 family) leads to the "poor metabolizer" phenotype in 5–10% of Caucasians, affecting the metabolism of many drugs including some beta-blockers and antiarrhythmics. (Reviewed in A. K. Daly et al., Metabolic polymorphisms, Pharmac. Ther. 57:129–60 [1993]). Some genetic variation can be associated with the accumulation of toxic products, for example treatment of TPMT-deficient (thiopurine methyltransferase) patients with 6-mercaptopurine or azathioprine can lead to a potentially fatal hematopoietic toxicity due to higher than normal levels of thioguanine nucleotides. (R. Weinshilboum, Methyltransferase pharmacogenetics, Pharmac. Ther. 43:77–90 [1989]; E. S. Vesell, Therapeutic lessons from pharmacogenetics, Ann. Intern. Med. 126:653–55 [1997]).

The presence of multiple genetic and environmental factors capable of creating such large variations in how drugs operate in the patient argues that individualization of the choice of drug and dosage is required for optimal treatment of disease, including atherosclerotic coronary artery disease. Jukema et al. (1996) reported that the HMG-CoA reductase inhibitor pravastatin did not lower the LDL-cholesterol level in subjects with the LPL N9 polymorphism to the same extent as in those with the LPL D9 polymorphism. In addition, J. A. Kuivenhoven et al. (1998) observed that pravastatin slowed the progression of atherosclerosis in subjects with the CETP B1B1 genotype, but not in those with the CETP B2B2 genotype. (J. A. Kuivenhoven et al., The role of a common variant of the cholesteryl ester transfer protein gene in the progression of coronary atherosclerosis, N. Engl. J. Med. 338:86–93 [1998]). These reports suggest that there are interactions between statin drugs and some genetic determinants of atherosclerosis.

There has been a definite need for a reliable predictive test for determining which patients suffering from coronary artery disease, or which CABG patients, will likely not respond positively to statin drug treatment with respect to stenosis of a coronary artery or bypass graft. Such a genetic testing method can provide useful information so that patients can be given more individually suited alternative treatments to prevent further injury.

This and other benefits of the present invention are described herein.

SUMMARY OF THE INVENTION

The present invention relates to a method of detecting a genetic predisposition in a human subject for non-responsiveness to statin drug treatment for coronary artery disease. This genetic testing method involves analyzing amplification products of the nucleic acids in a human tissue sample that includes a non-coding or untranslated region within the 3' end of the human LPL gene. Homozygosity for a variant allele in a non-coding or untranslated region within the 3' end of the human LPL gene indicates a genetic predisposition for non-responsiveness to treatment with statin-class drugs, such as lovastatin, pravastatin, simvastatin, atorvastatin, fluvastatin, and cerivastatin, which are typically prescribed to treat atherosclerotic stenosis in subjects with coronary artery disease, or to prevent graft worsening (stenosis) in CABG patients.

The present invention also relates to oligonucleotide primer sequences, primer sets, and genetic testing kits for practicing the method.

BRIEF DESCRIPTION OF THE DRAWINGS

FIG. 1 shows graft worsening in subjects related to different LPL variant alleles in the LPL gene.

FIG. 1(a) shows the location of some variant alleles in the LPL gene. Vertical bars represent exons. FIG. 1(b) shows the percentage of subjects with graft worsening. Each pair of vertical bars represents two genotype groups for each marker as defined in the box at the base of the bar. The number of subjects in each genotype group (N) is given below each bar. FIG. 1(c) represents the odds ratios and 95% confidence limits for graft worsening for each polymorphism.

DETAILED DESCRIPTION OF THE PREFERRED EMBODIMENTS

Figure 2:
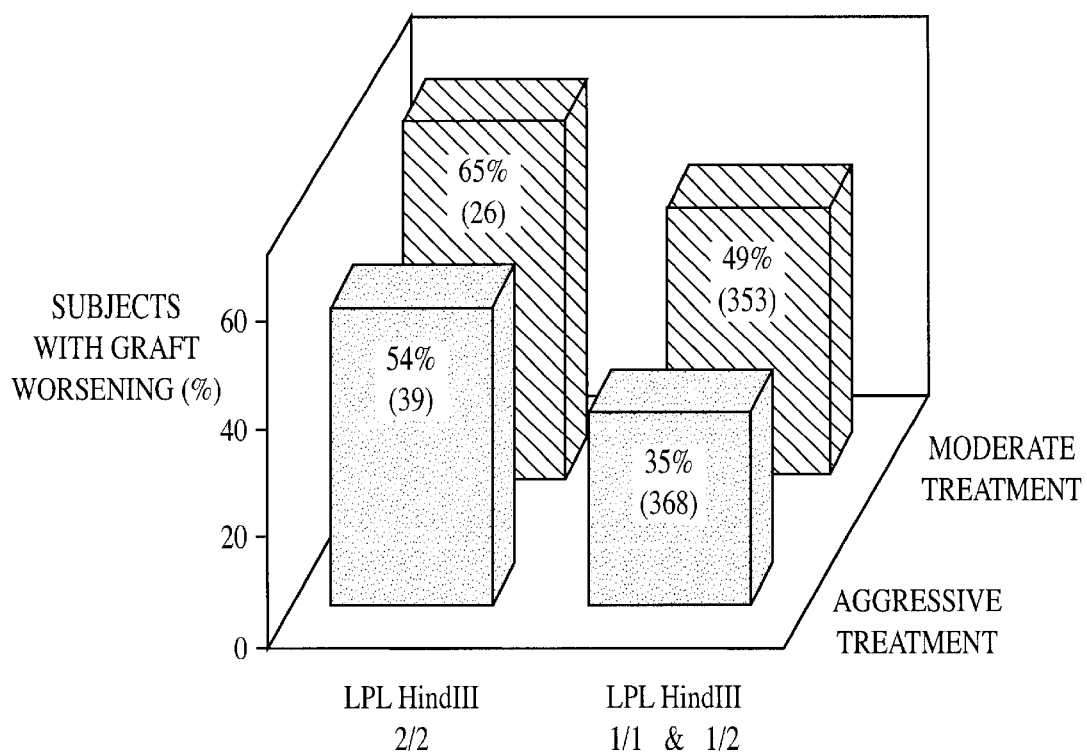
FIG. 2 shows graft worsening in subjects by HindIII genotype and drug treatment groups. The total number of subjects in each group is given on each vertical bar.

The present invention is directed to a method of detecting a genetic predisposition in a human subject for non-responsiveness to statin drug treatment for coronary artery disease or high blood pressure. This genetic testing method involves analyzing amplification products of the nucleic acids in a human tissue sample for homozygosity with respect to a variant allele in a non-coding or untranslated region of the 3' end of the human LPL gene. The present invention does not rely on and is not committed to any particular mechanism by which a variant allele or LPL polymorphism in a non-coding or untranslated region of the 3' end of the human LPL gene produces a phenotype of non-responsiveness to statin drug treatment.

The LPL gene is located on the short arm of human chromosome 8, at 8p22. (R. S. Sparkes et al., Human genes involved lipolysis of plasma lipoproteins: Mapping, of loci for lipoprotein lipase to 8p22 and hepatic lipase to 15q21, Genomics 1:138–44 [1987]). The gene is near microsatellite marker D8S1715 and flanked by microsatellites D8S261 and D8S280. Closer flanking sequences of human LPL are defined by GenBank accession numbers M94221 and M94222 (S. Wood et al., Support for founder effect for two lipoprotein lipase [LPL] gene mutations in French Canadians by analysis of GT microsatellites flanking the LPL gene, unpublished [1992]). The gene spans about 30 kb and contains 10 exons encoding a 475 amino acid protein including a 27 amino acid secretory signal peptide. (S. Deeb and R. Peng, Structure of the human lipoprotein lipase gene, Biochemistry 28(10):4131–35 [1989], T. G. Kirchgessner et al., Organization of the human lipoprotein lipase gene and evolution of the lipase gene family, Proc. Natl. Acad. Sci. USA 86:9647–51 [1989]).

The 3' end of the human lipoprotein lipase gene, for purposes of the present invention, includes nucleotide positions 4801 through 9734 of the Nickerson reference sequence extending from intron 6 into intron 9. (GenBank accession No. AF050163). (D. A. Nickerson et al., DNA sequence diversity in a 9.7-kb region of the human lipoprotein lipase gene, Nat. Genet. 19:233–40 [1998]). The complete Nickerson reference sequence is the following:

```
  1    TGTAACACAA AATTAAAATA AGTAGAATTA GTTTTCAGTA TTTCCTATAT TTGGAAAACA   (SEQ.ID.NO.:80)

61    ATATTTATAT TCATTTTGTT TCTTTTAGTT TTATTTTTGG CAGAACTGTA AGCACCTTCA

121    TTTTCTTTTT CTTCCAAAGG AGGAGTTTAA CTACCCTCTG GACAATGTCC ATCTCTTGGG

181    ATACAGCCTT GGAGCCCATG CTGCTGGCAT TGCAGGAAGT CTGACCAATA AGAAAGTCAA

241    CAGAATTACT GGTAAGAAAG CAATTTCGTT GGTCTTATCA TAAGAGGTGA AAAGACTGTC

301    ATTCTGAGAG AGAATCAGAA CAAATTTTGT TAAATACCCA CATGTGTGGT GTTCTTCCCG

361    GAGACATGAC CAGCACTTGA TTATCTCATT GTAGGGCTCT TTATTAGGGA TAAGAAAAAA

421    CACAGACGCT CTCACTGGCT TACTATCCAC TGGCAATAGC ACAGAAATAA AGCATAATTA

481    CACACAATGC CTGCAGATTT CTCTGGGAAG CCTGTTTCCT CCCACTCTCA GCTCTGTGTT

541    TTAGTAGTGT AAATGCACAT CAGTACTAGG AGAAAAGAAG AAGGACCAAT TCCAGAGGCC

601    ACTTCGAAAG AAGACCGTCA TCTAGGCAAA GGTGTGGCAT ACACACAGAG AGAAAGAACC

661    CACCACTGTT TATACATCTT CTCGACATAT TCAGAAATAA TCTACAAAAG GAAATCCAGC

721    CATCCTGAGT GGAAATTGCT GCATAAGGCT AGTTTAAGAG ACTCAAATTC ATTTTAGAAG

791    GAGCCAAGCC TCCTTTTATG TCTCTCTAAG TAAAGATACC ATGACTGTAG AATAGGAGCT

841    AATAAGAATC TAAATAGCTG CCAGTGCATT CAAATGATGA GCAGTGACAT GCGAATGTCA

901    TACGAATGGA AATTTACAAA TCTGTGTTCC TGCTTTTTTC CCTTTTAAGG CCTCGATCCA
```

-continued

```
 961 GCTGGACCTA ACTTTGAGTA TGCAGAAGCC CCGAGTCGTC TTTCTCCTGA TGATGCAGAT
1021 TTTGTAGACG TCTTACACAC ATTCACCAGA GGGTCCCCTG GTCGAAGCAT TGGAATCCAG
1081 AAACCAGTTG GGCATGTTGA CATTTACCCG AATGGAGGTA CTTTTCAGCC AGGATGTAAC
1141 ATTGGAGAAG CTATCCGCGT GATTGCAGAG AGAGGACTTG GAGGTAAATA TTATTTAGAA
1201 GCGAATTAAA TGTGACTCTT ATCCTTAACC CTTATTGACC CAATGTCCTA CTCAGTAGCT
1261 TCAAAGTATG TAGTTTTCAT ATACACATTT GGCCAAATTA TGTTTCTGAA GAATTCTGCA
1321 ATGTTCAGCA TGACCACCTT AGAGCCAGGC AGACAGCCAT TTTATCTTTT ATTTACTATA
1381 CTGTAGGCTA CACTGAGCAG TGCACTTACA GTAGCAAGAG AAAAAGGTGG GATTTTAGAC
1441 AGGAAGACTC CACTGACCTC AATAATGGCA TCATAAAATG CTATCTGGCC ACATGTTGTC
1501 ATACCTTGAA TGTAGCTGCA AAGCCAATGG AAAGATTTTA GATGTTACTG GAACAGAAGA
1561 TGTTAATTAG CATAAATCTT CCAAAATGTT CAGAACATAA TGTTAGCTTA ATGTTTTACT
1621 TTAATAATGT TAGCTTGTGT TAAATTTATG ATTTTTGTTT GTTTGTTTTT TGAGATAGAG
1681 TCTTATTCTA TTGCCCAAGC TGGGGTGCAG TCACACAATC ACAGGGACTT GCAATGTTGC
1741 CCAGGCTGGT CTCAAACTCC TGGCCTCAAG TGATCCTCCT GCCTCAGCCT CCCAAAGTTC
1801 TGGGATTGCA GCTGTGAGCC ACCACGCCCA GTTTACGATT TATTTTTAAG AGCCCCTTGC
1861 ATACTTTATA GACATTGGGA CCTACCTAGG ATATTCTCGT TATTTTTGTG CACGTAATAG
1921 AACTTAGAGC ATATTGTTAC TATTTTCGAT TGTCCTAAAA ACTTACAAGG AATTCATTCT
1981 TATGGCATTG CTGATTATTT CTATGTTCAT TTGATATAAA AGAGTGTTAG TAGGGGCAGA
2041 ACCCTCAATT GTACATAATA TCAATGATAA AATACAATTC ATTAACAAT TACCCTCTTA
2101 AGATGTGGTT TCTAGAAATA CAAATTGTCC CTAACTTACA GTTTTCCAAC TTTACAATTG
2161 GGCTGTAACA CCATTTTAAG TTGAGAAGCA CGTGATGGTT TGACTTAAAA CTTTTTGACA
2221 TTATGATGGG TTTTGGGGGT ATTAAGTGCA TTTTGACTTA CAGTATTTTT GACTTATGAA
2281 GAATTTATTG TAAGGCAAGG GGCAGGTATA TGTTTCTAGA AGCACCTAGA AGTGTTAGAC
2341 ACTTTCAATG TAAGAGAAGG ATGAGATAAA CAAGGAAATC ACACCTCCAC CTTGGAGGCT
2401 TATTACAGCT TCATAAACAT ACTCATAAAT ATAAGAAGCA CAAAAGTCAA AAATTCCCTG
2461 TGAACTTGCA ACTTTCACTC TCTTGAAGGT GGGTGGGCCG CTACCACCAA GAATATCTCC
2521 TGAAATAGGG CCTACAATCA TAAATGCACA GGACTATATC CTTGGGTGAT TCTACTCTAA
2581 CACCACATCT CACCTATTTT AGACATGCCA AATGAAACAC TCTTTGTGAA TTTCTGCCGA
2641 GATACAATCT TGGTGTCTCT TTTTTACCCA GATGTGGACC AGCTAGTGAA GTGCTCCCAC
2701 GAGCGCTCCA TTCATCTCTT CATCGACTCT CTGTTGAATG AAGAAAATCC AAGTAAGGCC
2761 TACAGGTGCA GTTCCAAGGA AGCCTTTGAG AAAGGGCTCT GCTTGAGTTG TAGAAAGAAC
2821 CGCTGCAACA ATCGGGCTA TGAGATCAAT AAAGTCAGAG CCAAAAGAAG CAGCAAAATG
2881 TACCTGAAGA CTCGTTCTCA GATGCCCTAC AAAGGTAGGC TGGAGACTGT TGTAAATAAG
2941 GAAACCAAGG AGTCCTATTT CATCATGCTC ACTGCATCAC ATGTACTGAT TCTGTCCATT
3001 GGAACAGAGA TGATGACTGG TGTTACTAAA CCCTGAGCCC TGGTGTTTCT GTTGATAGGG
3061 GGTTGCATTG ATCCATTTGT CTGAGGCTTC TAATTCCCAT TGTCAGCAAG GTCCCAGTGC
3121 TCAGTGTGGG ATTTGCAGCC TTGCTCGCTG CCCTCCCCTG TAAATGTGGC CATTAGCATG
3161 GGCTAGGCTA TCAGCACAGA GCTCAGAGCT CATTTGGAAC CATCCACCTC GGGTCAACAA
3241 ACTATAACCC TTGTGCCAAA TCCAGCCTAC TTCCTGCTTT TGTAAATAGT TTTTTTAAAA
3301 CTTTTAAGTT CAGGGGTACG TATGTAGGTT TGCTAAAAAG GTAAACTTGT GACATGGGAG
```

-continued

```
3361 TTTGTTGTCC AGAATATTCC ATCACCCAGG TATTAAGCTT AGTACCCATT AGTTACTTTT
3421 CCTGAAGCTC TCCCTCCTCC CACCCTCTGG GAGGCCCCAG TGTCTGTTGT TCCCCTCTAT
3481 GTGCTCATGC AAAGTTTTAT TAGGACACAG CCACACACAT TCATTACCAT ATTGTCAAAG
3541 GCTGGTTTCA TGCCACCATA ACAGAGTTGA TAGCCCACAG AGCCTAAAAT ATTTACTCCC
3601 TGGCCCTTTA CAGAATGTTC ACAACTTACA TAAAGGCAAG GACCATCTGT CTTATTTATT
3661 TATTTATTTA ATTTGAGATG AAGTCTAGCT TTCTCCTAGG CTGGAGGAGA GGGGCATGAT
3721 CTTGGCTCAC CACAACCTCT GCCTCCCGGG TTCAAATGAT TCCCCTGCCT CAGCCTCCGG
3781 AGTAGCTGGG ATAACAGGCA TGCACCATCA TGCCCAGCTA ATTTTTGTAT TTTTAGTAGA
3841 GAGGGGGTTT CACCGTGTTG ACCAGGCTGG TCTCGAACTG CTGACCTCAG GTGATCTGCC
3901 CTCCTTGGCC TCATCTGTCT TTTTAAATGC AACTATTCCT GGAAGGCAAG AATATCTCAC
3961 ACCTTCTAAG ATACTGCCAT TTTGCCAGGA GTTTGTTTCA CACTTGAATT TCAAGCTTGG
4021 CCTCTTGTTT AGAGGCAGAC CTAAAGGAAT GGTCGGAAAA TGAGAGAGGA GGTCTTCGGA
4081 TAAATCCGGT GAGAGGGACC AACTTCAGGA AGGGTGGCTT TTGTGGAATC CAGATGGAAA
4141 CCTGAGGGAA GGGATGATAT TAAAGAACAG TGGCCCCAGG TAAAACATAT GGCACCCATG
4201 TGTAAGGTGA TTCTTAGAAT CTGTAGAGGT GTCTTTCGTG GTATAGAGGT TGAGGCACCT
4261 GTGCTTCAAG GAAACCTTAA CTCTTCAAAA TCAGGCAATG CGTATGAGGT AAAGAGAGGA
4321 CTGTGGGACC ATAATCTTGA AGACACAGAC AGGCTTCACT CATCCCTGCC TCCTGCACCA
4381 GTGGGTTCAA GGCTCTGTCA GTGTCCCCTA GGGGCACCTC ACCACTCCCA GCTTCTTCAG
4441 CTCTGGCCTG TCCTGCTGCC TGCAAGGGTT TTGCTTAATT CTCAATTCAA TGTCTCTTCA
4501 TCTTTTAGTA GCTGTGGGGT TTTGTTGTTG TTCTTCTGTT TTTGCTTAGT ATCTGACTAC
4561 TTTTTAATTA TAAAAAGAGA TGTATCTAAA CAAAATAGAG ATTGTTATCA GAAGTTCACA
4621 ACATTTATTA AAAATTTTTT CACCTGGACA AGAGTCTAAA GCAGCATAAA AATATGGTCT
4681 GCTATATTCT AAACCATCAG TCTTAAGAGA TCTGTGTCTC AGCTTAAGAG AAAATACATT
4741 TAATAGACAG TAACACAAAT AAGAAAAAAA TCTGACCAAG GATAGTGGGA TATAGAAGAA
4801 AAAACATTCC AAGAATTATT TTATTTATTT ATTTATTTAT TTATTTATTT ATTTATTTAT
4861 TTTTGAGACA CGGTCTCGCT CAGTTACCCA GGCTGGAGTG CAGCGGCGCA ATCTTAACTC
4921 ACTGCAACCT CTGCTTTCCG GTTCAAGCGA TTCTCCTGCC TCAGCCTCCT GAGTAACTGG
4981 GATTACAGGC ACCCGCCACC ACGCCCAACT AATTTCTGTA TTTTTCTTAG TAGAAACAGG
5041 GTTTCACCAT GTTGGCCAAG CTAGTCTCAA ACTCCTGACC TCAGGTGATT CACCCACCAA
5101 GGCCTCCCAA AGTGCTGGGA TTACAGGCAT GAGCCACCAT GCCTGGCCTC AAAAACTCT
5161 TTTTTCCTCC ATCATCATGG TTCTATTTTA GTCCTGCTGC CTTTCCTTTT AACCTCTCCC
5221 CAGGCCCATT TGCTCAGGGT TTTTGGTAGA GACCAGAGGA GGGGCAGGGA GGAGATATAG
5281 AAGTTCAACT ACCTGCTTCC AGAGGCTGTC CCTAGTATAG AATACTTTAG GGGCTGGCTT
5341 TACAAGGCAG TCCTTGTGGC CTCACTGATG GCTCAATGAA ATAAGTTCTT TTTTAAAAAA
5401 AATTTTATTT ATTTCCATAG GTTATTGGGG GAACAGGTGG TGTTTGGTTA CATGAGTAAG
5461 TTCTTTAGTA GTGATTTGTG AGATTTTGGT GTGCCCATTA CGGAATGGAA AAATCAACGA
5521 AATAAGTTCT ATGATGCACC TACTAGACAC CTAATCTGCA CTAGATGGTG GGGGAATTAA
5581 GAGCATGGGC ATGATCCTGT GACCGGAAGC CCGCTTACAG TCAGGGTGGA GGACAGACCT
5641 ACTCATGAAA CAAACACAGT GACATATAGT GACACAGAAG CAAATGTCAA ATATGCTTGC
5701 TCCAGATGCT AAGGCACAAG ATGGCCAAGG ATGGCGGAGT TCATGGAGAA AGCATCATGA
```

-continued

```
5761 GTGTTTTGGC CTTCTGATTT GATCTCCCTA GCACCCCTCA AAGATGGCTA CTTCCTAATG

5821 CTGCTTGGCA ATTCAGACAC ATTTGGGTTT TTCCTATGCA TATAACCACA CTTTTCTGAA

5881 AGGGAGTAGA ATTCAAGGTC TGCATTTTCT AGGTATGAAC ACTGTGCATG ATGAAGTCTT

5941 TCCAAGCCAC ACCAGTGGTT CCATGTGTGT GCACTTCCGG TTTGAGTGCT AGTGAGATAC

6001 TTCTGTGGTT CTGAATTGCC TGACTATTTG GGGTTGTGAT ATTTTCATAA AGATTGATCA

6061 ACATGTTCGA ATTTCCTCCC CAACAGTCTT CCATTACCAA GTAAAGATTC ATTTTTCTGG

6121 GACTGAGAGT GAAACCCATA CCAATCAGGC CTTTGAGATT TCTCTGTATG GCACCGTGGC

6181 CGAGAGTGAG AACATCCCAT TCACTCTGTG AGTAGCACAG GGGGCGGTC ATCATGGCAC

6241 CAGTCCCTCC CCTGCCATAA CCCTTGGTCT GAGCAGCAGA AGCAGAGAGC GATGCCTAGA

6301 AAACAAGTCT TTAGTTAAAA AAATCAGAAT TCAAAATTG AGGTCTTTCC TCTATTTGAT

6361 ATTGAGAAAA AAATGCTTCA AATTGGCCAT TTTATTTTCA CTTACTAGTT ATATTTTTTT

6421 ATTTATCATC TTATATCTGT TTATTTCTTT TATAAAGCTG CTGTTAAACA ATATAATTAA

6481 ACTATCTCAA AAGGTTTGAC ATTAAAGAAA ATGAGCAATG GTAACAGGAA ACCACTCTAT

6541 AGATGTACAT ATAATATGTA CAGAAAATAT AAGTAGTAAG AAGTCCATGA CAAAGTGTTA

6601 GCTCTTTTTT TTTTTTTTT TTTTTTTTT TTTGAGATGG AGTCTCTCTC CTATTGCCCA

6661 GGCTGGAGTG CAGTGATTCG ATCTCAGCTC ACTGCAACCT CTACCTCCCG AGTTCAAACA

6721 ATTCTTCTGT CTCAGCCTCC CGAGTAGCTG GGGCTGCAGG TGCCCACCAC CATGCCCAGC

6781 TAATTTTTGT ATTTTTAGTA GCGACAGGGT CTCACCATGT TGGCCAAGCT GGTCTTGAAT

6841 TCCTGATCTC AGGTGATCCA CCCGCCTCGG CCTCCCAAAG TGCTGGGATT ACAGGTGTGA

6901 GCCACCATGC CCAGCCTACC CTTTACTACT AATCAAAGAA ATAAAAGTAA GGCAACTTGA

6961 TACTTTTACA ATTACTAGAT GAACAAATCT TTAAAAATAG CCAGTGCAGA CAAGGTGGTG

7021 AAGCAGAACA TGCAACCTA CCATGCATCA TTCACGGCTA GAACCCTCCA GGTGCGGAAG

7081 GTAGTATTTT AATAACTTTC CATAGCTACA AAATATTATT ACATAGAAGG GAGTGATTTT

7141 TTTCTAATAT TTATCCTAAA GAAATAGTCA ACAAACATTT TAAAAAACA TCAATTACAG

7201 TCGTACCTAT ACTAGCATAA ATTAGAAACC CAGTATCCAA CATTGAGGCA GTGGGTAAAT

7261 GAATCGTGGT TTATCAAGTC ATTAAAATCA ATCTAGCCTT TAAAAACTAT AATTGTAGGA

7321 AACCCAGGAA AACATAGTAA AAAATGGAAT ATAAAATCTA AAGAGAATAA AGAATAGAGA

7381 ATCGTATGTG TGCTATGATT GTAGCTAAAT AATGTTCAAG TATCAACACA AATTGAAAAG

7441 GAATACATGA AAATGAAAAT TATATTTCTG AATGATTGAC TTCAGGATTT TCTTTTAGAA

7501 TTGTATTAAA TAGTTCATGT CATTAGGATA AATGCTGGAA TGTGGATATA ATTTAAAATA

7561 TACTAAATGC CATCGACCTT CATTTTGAGT TCTTTGTTGG ACATTTTTGT GCATTTTTAA

7621 AATATCCCCT AAATAATAAA GCTATTTATA TTTGGAGAGG AGAAAAAAAA GTGGGGGGCA

7681 GGGAGAGCTG ATCTCTATAA CTAACCAAAT TTATTGCTTT TTTGTTTAGG CCTGAAGTTT

7741 CCACAAATAA GACATACTCC TTCCTAATTT ACACAGAGGT AGATATTGGA GAACTACTCA

7801 TGTTGAAGCT CAAATGGAAG AGTGATTCAT ACTTTAGCTG GTCAGACTGG TGGAGCAGTC

7861 CCGGCTTCGC CATTCAGAAG ATCAGAGTAA AAGCAGGAGA GACTCAGAAA AAGTAATTAA

7921 ATGTATTTTT CTTCCTTCAC TTTAGACCCC CACCTGATGT CAGGACCTAG GGGCTGTATT

7981 TCAGGGGCCT TCACAATTCA GGGAGAGCTT TAGGAAACCT TGTATTTATT ACTGTATGAT

8041 GTAGATTTTC TTTAGGAGTC TTCTTTTATT TTCTTATTTT TGGGGGCGG GGGGGGAAGT

8101 GACAGTATTT TTGTATTTCA TGTAAGGAAA ACATAAGCCC TGAATCGCTC ACAGTTATTC
```

-continued

```
8161 AGTGAGAGCT GGGATTAGAA GTCAGGAATC TCAGCTTCTC ATTTGGCACT GTTTCTTGTA

8221 AGTACAAAAT AGTTAGGGAA CAAACCTCCG AGATGCTACC TGGATAATCA AAGATTCAAA

8281 CCAACCTCTT CAAGAAGGGT GAGATTCCAA GATAATCTCA ACCTGTCTCC CCAGCCCCAC

8341 CCATGTGTAC CCATAAAATG AATTACACAG AGATCGCTAT AGGATTTAAA GCTTTTATAC

8401 TAAATGTGCT GGGATTTTGC AAACTATAGT GTGCTGTTAT TGTTAATTTA AAAAAACTCT

8461 AAGTTAGGAT TGACAAATTA TTTCTCTTTA GTCATTTGCT TGTATCACCA AAGAAGCAAA

8521 CAAACAAACA AAAAAAAAAA GAAAAAGATC TTGGGGATGG AAATGTTATA AAGAATCTTT

8581 TTTACACTAG CAATGTCTAG CTGAAGGCAG ATGCCCTAAT TCCTTAATGC AGATGCTAAG

8641 AGATGGCAGA GTTGATCTTT TATCATCTCT TGGTGAAAGC CCAGTAACAT AAGACTGCTC

8701 TAGGCTGTCT GCATGCCTGT CTATCTAAAT TAACTAGCTT GGTTGCTGAA CACCGGGTTA

8761 GGCTCTCAAA TTACCCTCTG ATTCTGATGT GGCCTGAGTG TGACAGTTAA TTATTGGGAA

8821 TATCAAAACA ATTACCCAGC ATGATCATGT ATTATTTAAA CAGTCCTGAC AGAACTGTAC

8881 CTTTGTGAAC AGTGCTTTTG ATTGTTCTAC ATGGCATATT CACATCCATT TTCTTCCACA

8941 GGGTGATCTT CTGTTCTAGG GAGAAAGTGT CTCATTTGCA GAAAGGAAAG GCACCTGCGG

9001 TATTTGTGAA ATGCCATGAC AAGTCTCTGA ATAAGAAGTC AGGCTGGTGA GCATTCTGGG

9061 CTAAAGCTGA CTGGGCATCC TGAGCTTGCA CCCTAAGGGA GGCAGCTTCA TGCATTCCTC

9121 TTCACCCCAT CACCAGCAGC TTGCCCTGAC TCATGTGATC AAAGCATTCA ATCAGTCTTT

9181 CTTAGTCCTT CTGCATATGT ATCAAATGGG TCTGTTGCTT TATGCAATAC TTCCTCTTTT

9241 TTTCTTTCTC CTCTTGTTTC TCCCAGCCCG GACCTTCAAC CCAGGCACAC ATTTTAGGTT

9301 TTATTTTACT CCTTGAACTA CCCCTGAATC TTCACTTCTC CTTTTTTCTC TACTGCGTCT

9361 CTGCTGACTT TGCAGATGCC ATCTGCAGAG CATGTAACAC AAGTTTAGTA GTTGCCGTTC

9421 TGGCTGTGGG TGCAGCTCTT CCCAGGATGT ATTCAGGGAA GTAAAAAGAT CTCACTGCAT

9481 CACCTGCAGC CACATAGTTC TTGATTCTCC AAGTGCCAGC ATACTCCGGG ACACACAGCC

9541 AACAGGGCTG CCCCAAGCAC CCATCTCAAA ACCCTCAAAG CTGCCAAGCA AACAGAATGA

9601 GAGTTATAGG AAACTGTTCT CTCTTCTATC TCCAAACAAC TCTGTGCCTC TTTCCTACCT

9661 GACCTTTAGG GCTAATCCAT GTGGCAGCTG TTAGCTGCAT CTTTCCAGAG CGTCAGTACT

9721 GAGAGGACAC TAAG
```

Also for purposes of the present invention, the 3' end of the human lipoprotein lipase gene includes exon 10 and the 3' untranslated region (3'UTR), at least partially defined by nucleotide positions 1 through 3240 of the reference sequence of Oka et al., (GenBank accession No. X52978 and X53518; K. Oka et al., Structure and polymorphic map of human lipoprotein lipase gene, Biochim. Biophys. Acta 1049(1):21–26 [1990], Erratum:[Biochim Biophys Acta Nov. 11, 1991;1090(3):357]). In the reference sequence of Oka et al., the first and second polyadenylation signals are at nt. 15–20 and 411–416, respectively (in bold), and two analogous AGTAAA sequences are at nt. 468–473 and 529–534 (in bold). The poly (A) addition site is at nt. 439. The following is the reference sequence of Oka et al.:

```
  1   GAATTCTCTC TAAAAATAAA ATGATGTATG ATTTGTTGTT GGCATCCCCT TTATTAATTC     (SEQ.ID.NO.:94)

61   ATTAAATTTC TGGATTTGGG TTGTGACCCA GGGTGCATTA ACTTAAAAGA TTCACTAAAG

121   CAGCACATAG CACTGGGAAC TCTGGCTCCG AAAAACTTTG TTATATATAT CAAGGATGTT

181   CTGGCTTTAC ATTTTATTTA TTAGCTGTAA ATACATGTGT GGATGTGTAA ATGGAGCTTG

241   TACATATTGG AAAGGTCATT GTGGCTATCT GCATTTATAA ATGTGTGGTG CTAACTGTAT

301   GTGTCTTTAT CAGTGATGGT CTCACAGAGC CAACTCACTC TTATGAAATG GGCTTTAACA
```

-continued

```
 361 AAACAAGAAA GAAACGTACT TAACTGTGTG AAGAAATGGA ATCAGCTTTT AATAAAATTG
 421 ACAACATTTT ATTACCACAC TAAGTCATTA TTTTGTATCA TTTTTAAAGT AAATTTATTC
 481 TTAGGTCAGA TTCACTCAGC ATATTTTGAC TAAGTAACCA CTGTACTTAG TAAACCGAAG
 541 AGCTTCTGAG AATTATAGTG TACCGTATAG ATATTTTTAA CATTTATATT TGTATAAAGC
 601 TAAAGAAAGC CTTACATATC CTTTAAACTG ACTATAGAAG AAAATGATAC AGAATTTTGC
 661 CTGCATAAAG TACACAGGAC TATTCTTGCC TACAATATGC TTTTTCACAA GCAAAATGTT
 721 AGACTAATAT AAGGCATCTT TGGCCATTTT ATAGTGTACA TCATCTCTAT TTCTGAGGCC
 781 TCATTGTTAG CTGTAACGCA AGTAGCATTT GTGCAATAAA ATGAACTATT TGGGATGGGA
 841 GGGTACATTT TTTAGAACTT TGCTTTGGGT TGCCTTGATA ATTAATAGCA TATAGTCCAT
 901 TTATGCAGCT AAGTAGGGAT TGCTTCTTAG TACAGTCAGG AAGAATTTAG CCCAGAAAAC
 961 AATTATTTCA ATGGCCACTG ACCCAAACTT CCAGGCTGAA GAGCAATGGC GTGATCATGG
1021 CTCACTGCAC CTCCACCTCC CAGGCTCAAG TGATTCTCCT GCCTCAGCCT CCCAAGTAGA
1081 TGGTACTACA AGCACACGCC ACTGCACCCA GCTAATTTTT GTATTTTTTG TAGAGATGGG
1141 GGTTTCACCA TGTTGCCCAG GCTGGTCTTA AATTCCTGGC CTCAAGTGTC TGCCCCCCTT
1201 GGCCTCCCAA AGTGCTGGAA TTACAGGCAT GAGCCACCAT GTCCAGCCTT GACCCAAACT
1261 TTTATTGTCA GTTAGCTATT GGGGCTTCT GGAGTTTGGG TCTCCCCTGA CAGGAGGGGG
1321 CTCCCCAGTT CACACTTGGC CACTGCCCAT CAATTCCTGT TGATATGATC AACAAGATAG
1381 ACAATTGCAA ATGTTGCTGA GGATGTGGAG AAGTGTGAAC CTGTGTAAGT GGCTGATGGG
1441 AATGTAAAAT GGCACAGCCA CTATGGAGAA CAATTTGGTA GTATTTCCAA AGTTAAGCAT
1501 AGAGTTTAAC CCATATGACC CAGCAATTCC ACTCCTAGAT ATATACCCAA GAGAAATGAA
1561 AACACAGATC CACAAAGATT TGCACACACA GGTTCATAGC AGCATTAATC AGATTAGTCC
1621 CAAAGTGGAC AACCCAAATG TCCATGAACT TGTGAAAGAG ATAAGCAAAA TGTGACAAAT
1681 TCACATAATA AAATATTATT CAGAAGTAAA AGAACAAGC AGCAGATATA TGATACAACA
1741 CGATGCGCCT TGAAAACGTT TAGCCATATG AAAGAAACCA GATGCAAAAT GGAACCATGG
1801 CTTAGGGGAG GAGAACGGCA CAATGGTGTA AAAGTTGCAG AGAGGAACAA AAAGGCTACC
1861 TGCCTCGCTC CCAGGCCAAG TAACACAGGA GGAAAGAAAA TATCCACATA TGCGAGGGCT
1921 AAAGGAAAGA GGTGTTCTCA AGCTGAAGCA GGAGGTGGGA CTCAACTCTG GAGGTGGGCC
1981 TCACACACTG TACCAAATTG AGGACTAGCT AAAACAGGGA TGGGGGTGAA AGCACCTTTT
2041 CGTAAGACAT GCCCACCATT GTCCCGTTCT CCTCCCTTAA GCCCTTGTCT TGCTCATGTC
2101 AGCAAGCTTA TTGCCATCTA TTCTTCCTAG TTACAGACAT CTGTGGAGCT CTGAGTTTTT
2161 TGCCTAATCA TTATTTTAGA ACCTGGTTCA CTCTCTCTCC CTTCTACACT AGTTCTGTCA
2221 TTATTATTAC TGATTTCAGT ACCTCTGAGG TGATAGATTT TATTTTCCAA TGGCAGCCAC
2281 AACACTACCT CCCATTCTAT ATGTTCCCCT GCAATGTTGC CTTGACATCC CTATTAAGAG
2341 TTGGAATCTA GTCACCCCGC TTTTCTAGTC TCCCCACTCC TTTGAACTTG TGTGGGCCCT
2401 AAGATTGCTT CTACTAGTAG AATAGAACTA AAATGACCCT GGACCAGTGT GGGGTGCAGC
2461 CCTTAACTGG CCTGGCAGCT TCTGCTTTTG GTTCCTTGGG GCACTCACTC TTGGGAAACT
2521 TCCCTTTGGA ACTCAGCATT CATGATGCGG AAGTTGAAGC CACATGAAAA GAGCATATGG
2581 TGGTTCTCTC AGCTCCCAGC CAACAACCAG TCTCGACTGT CAGCCATGTG AGTGAGGCAT
2641 CTTGGACCTC CGGCCAGTTG AGTGTTCAGA AGACTGCAGC TCGAGCTGGC ATCTGGATGC
2701 AACCACATGA GAGACGCTCT GCCCAGCCAA GCCCAGCCAA CTCACAGTAC TATGAGAGAT
```

```
                                 -continued
2761 ACTAATAACT TGTTGTTGTT GTTGTTGTTG TTGTTTTTAT TATTAAACTT TAAGTTTTAG

2821 CATACACGTG CACAACGTGC AGGTTAGTTA CATATGTATA CCTGGGCCAT GTTGGTGTGC

2881 TGCACCCAGT AACTCGTCAT TTAACATTAG GTATATCTCC AAATGCTATC CCTCCCCCCT

2941 CCCTAAGTTT TTAGGAGTTT GCTTTGCAAC GATAGATAGT TGAAACATCT GGATGATGCA

3001 TCCAGTATTC TGGCTTCTCA CTGCCTTTAC CTCCTCTCTC CCATGGCCTT GTCTTCTAAA

3061 TCTACCTTTA CATAGAAACA TTCAGTCACG TGCTATACTA TATCATGCCA TTACTAATAA

3121 CTCATAAACT CAATTTCAAC TTCTCCCTTC TTTGACTACC ACATGCTATC

3181 AATCAA GTGCTCTCAG TTCAACAGCT CCTCAACTGC CCCAGGACCT CCAATACATT//.
```

Also for purposes of the present invention, the 3' end of the human lipoprotein lipase gene includes the intervening nucleotide sequence between the end of the Nickerson reference sequence in intron 9 and the beginning of the reference sequence of Oka et al.

A non-coding or untranslated region of the 3' end of the human LPL gene includes any non-transcribed or untranslated nucleotide sequence within the 3' end, including all intronic sequences. Included are the part of intron 6 extending from Nickerson reference sequence position nt. 4801 through nt. 6086; intron 7 from nt. 6208 through nt. 7729; intron 8 from nt. 7913 through nt. 8941; and intron 9 from nt. 9047 through nt. 9734. Also included is exon 10 and the 3'UTR.

A variant allele in a non-coding or untranslated region of the 3' end of the human LPL gene is a mutation or polymorphism with respect to the Nickerson or Oka et al. reference sequences, of any class, such as, but not limited to, a single nucleotide polymorphism (SNP). Included among the sources of variant alleles in a non-coding or untranslated region of the 3' end of the human LPL gene are deletion mutations, insertion mutations, inversions, translocations, transitions, tranversions, or repeats.

Examples of homozygous genotypes that indicate a genetic predisposition to non-responsiveness to statin drug treatment, in accordance with the present method, include, but are not limited to, the HindIII 2/2 and (TTTA)$_n$ 4/4 genotypes.

et al. [1990]; C. Heinzmann et al., RFLP for the human lipoprotein lipase [LPL] gene. HindIII, Nuc. Acids Res. 15:6763 [1987]; D. A. Nickerson et al. [1998]). For purposes of the present invention, nucleic acids comprising the normal locus of the HindIII recognition site in intron 8 of the human LPL gene are any nucleic acid sequences that overlap the entire six-basepair region at positions 8389–8394 of the Nickerson reference sequence, whether or not the nucleic acid sequence of a particular human subject at that locus is AAGCTT.

The tetranucleotide (TTTA)$_n$ repeat sequence in intron 6 of the LPL gene begins at position 4819 of the Nickerson reference sequence and extending to position 4864. There are five known (TTTA)$_n$ alleles or polymorphisms. Allele 4 yields a 131 bp nucleotide fragment when PCR amplification is done using a primer set comprising reverse primer GZ-15 (5'-CCT GGG TAA CTG AGC GAG ACT GTG TC-3'; SEQ. ID. NO. 33) and forward primer GZ-14 (5'-ATC TGA CCA AGG ATA GTG GGA TAT A-3'; SEQ. ID. NO.:34).

In the (TTTA)$_n$ 4 variant allele, two additional TTTA repeats (shown below in underlined boldface type) are added to give the (TTTA)$_n$ 4 allele length of 131 bp. Nucleotide position numbers with respect to the Nickerson reference sequence will be off from that point on:

```
4501 TCTTTTAGTA GCTGTGGGGT TTTGTTGTTG TTCTTCTGTT TTTGCTTAGT ATCTGACTAC    (SEQ.ID.NO.:93)

4561 TTTTTAATTA TAAAAGAGA TGTATCTAAA CAAAATAGAG ATTGTTATCA GAAGTTCACA

4621 ACATTTATTA AAAATTTTTT CACCTGGACA AGAGTCTAAA GCAGCATAAA AATATGGTCT

4681 GCTATATTCT AAACCATCAG TCTTAAGAGA TCTGTGTCTC AGCTTAAGAG AAAATACATT

4741 TAATAGACAG TAACACAAAT AAGAAAAAAA TCTGACCAAG GATAGTGGGA TATAGAAGAA

4801 AAAACATTCC AAGAATTATT TTATTTATTTATTTATTT ATTTATTTAT TTATTTATTT ATTTATTTAT

4861 TTTTGAGACA CGGTCTCGCT CAGTTACCCA GGCTGGAGTG CAGCGGCGCA ATCTTAACTC

4921 ACTGCAACCT CTGCTTTCCG GTTCAAGCGA TTCTCCTGCC TCAGCCTCCT GAGTAACTGG

4981 GATTACAGGC ACCCGCCACC ACGCCCAACT AATTTCTGTA TTTTTCTTAG TAGAAACAGG

5041 GTTTCACCAT GTTGGCCAAG CTAGTCTCAA ACTCCTGACC TCAGGTGATT CACCCACCAA

5101 GGCCTCCCAA AGTGCTGGGA TTACAGGCAT GAGCCACCAT GCCTGGCCTC CAAAAACTCT//
```

The HindIII 2 variant allele, is created by a T to G transition in the single HindIII recognition site mapped in intron 8, i.e., AAGCTT to AAGCGT (SEQ. ID. NO.:99), at position 8393 of the Nickerson reference sequence. (K. Oka A statin drug is any 3-hydroxy-3-methylglutaryl coenzyme A (HMG-CoA) reductase inhibitor, including, but not limited to, lovastatin, pravastatin, simvastatin, atorvastatin, fluvastatin, and cerivastatin.

A human subject, particularly a CABG patient, who has a genetic predisposition for non-responsiveness to statin drug treatment possesses an hereditary inclination, susceptibility, or tendency to develop atherosclerotic stenosis of coronary blood vessels, including of a native coronary artery, or of any coronary artery bypass graft using a saphenous vein or any other vein or artery, in a manner that does not respond to statin drug treatment. It does not mean that at any time such a person will actually develop stenosis of a coronary blood vessel, or graft worsening (graft lumen narrowing). It merely means that he or she has a greater likelihood of developing stenosis, when statin treatment is given; this is in comparison to the general population of individuals who are not homozygous for a mutation in the 3' end of the LPL gene, for example for the HindIII 2 allele or $(TTTA)_n$ 4 allele, including those who have atherosclerotic coronary artery disease, who are coronary artery bypass graft patients.

A CABG patient is a human subject who is a candidate for coronary artery bypass graft surgery or one who has undergone a coronary artery bypass graft procedure.

Any human tissue containing nucleic acids can be sampled and collected for the purpose of practicing the methods of the present invention. A most preferred and convenient tissue for collecting is blood. Collecting a tissue sample includes in vitro harvest of cultured human cells derived from a subject's tissue or any means of in vivo sampling directly from a subject, for example, by blood draw, spinal tap, tissue smear or tissue biopsy. Optionally, tissue samples are stored before analysis by well known storage means that will preserve a sample's nucleic acids in an analyzable condition, such as quick freezing, or a controlled freezing regime, in the presence of a cryoprotectant, for example, dimethyl sulfoxide (DMSO), glycerol, or propanediol-sucrose. Tissue samples can also be pooled before or after storage for purposes of amplifying them for analysis.

Amplifying nucleic acids from a tissue sample of a subject to obtain amplification products includes any conventional means of amassing sufficient nucleic acid material for analysis. Most preferably, amplification is by conventional polymerase chain reaction (PCR) methods. Alternatively, amplification of nucleic acids is by in vitro cell culture and harvest of the subject's cultured cells, or by multiple sampling from the subject's tissues in vivo and pooling of multiple tissue samples from a subject. Nucleic acids thus amplified are amplification products if they include a non-coding or untranslated nucleotide sequence from the 3' end of the LPL gene, for example, the normal locus of the HindIII recognition site in intron 8, or the tetranucleotide $(TTTA)_n$ repeat region of intron 6, of the human LPL gene.

In a preferred embodiment of the present method, nucleotide sequencing is used to analyze the amplification products of the nucleic acids in a tissue sample to detect homozygosity for a mutation in the 3' end of human LPL. The skilled artisan can detect the mutation by any nucleotide sequencing means, for example conventional dideoxy sequencing or preferably by using a commercially available automated sequencer, then comparing the subject's nucleotide sequences to other known human LPL sequences available in genomic sequence databases, such as GenBank.

In a most preferred embodiment that employs nucleotide sequencing, sequencing of 3' end LPL sequences is accomplished by using fluorescence-based single strand conformation polymorphism analysis (SSCP), a routine and reliable means of identifying point mutations, small insertions or deletions. (J. S. Ellison, Fluorescence-based mutation detection. Single-strand conformation polymorphism analysis [F-SSCP], Mol. Biotechnol. 5(1):17–31 [1996]; H. Iwahana et al., Multiple fluorescence-based PCR-SSCP analysis using internal fluorescent labeling of PCR products, Biotechniques 21(3):510–14, 516–19 [1996]; R. Makino et al., F-SSCP. fluorescence-based polymerase chain reaction-single-strand conformation polymorphism [PCR-SSCP], PCR Methods Appl. 2(1):10–13 [1992]). An automated system may be used, such as an Applied Biosystems DNA sequencer, equipped with GENESCAN 672®, Genotyper®, or another appropriate analytical software package.

Optionally, high throughput analysis may be achieved by PCR multiplexing techniques well known in the art. (E.g., Z. Lin et al., Multiplex genotype determination at a large number of gene loci, Proc. Natl. Acad. Sci. USA 93(6):2582–87 [1996]).

In a most preferred embodiment, nucleotide sequencing is unnecessary for analyzing the amplification products. For example, heteroduplex analysis on high resolution gel matrices are employed to detect even single nucleotide polymorphisms. (M. T. Hauser et al., Generation of co-dominant PCR-based markers by duplex analysis on high resolution gels, Plant. J. 16(1):117–25 [1998]). The PCR/OLA procedure can be used for analyzing amplification products to detect SNPs in the 3' end of the human LPL gene. (B. R. Glick and J. J. Pasternak, Molecular Biotechnology: Principles and Applications of Recombinant DNA, ASM Press, Washington, D.C., pp. 197–200 [1994]). Conformation-sensitive gel electrophoresis of amplification products may also be employed as a means of analysis by the skilled artisan in practicing the methods of the present invention. (A. Markoff et al., Comparison of conformation-sensitive gel electrophoresis and single strand conformation polymorphism analysis for detection of mutations in the BRCA1 gene using optimized conformation analysis protocols, Eur. J. Genet. 6(2):145–50 [1998]).

Electrophoresis for analyzing amplification products is done rapidly and with high sensitivity by using any of various methods of conventional slab or capillary electrophoresis, with which the practitioner can optionally choose to employ any facilitating means of nucleic acid fragment detection, including, but not limited to, radionuclides, UV-absorbance or laser-induced fluorescence. (K. Keparnik et al., Fast detection of a (CA)18 microsatellite repeat in the IgE receptor gene by capillary electrophoresis with laser-induced fluorescence detection, Electrophoresis 19(2);249–55 [1998]; H. Inoue et al., Enhanced separation of DNA sequencing products by capillary electrophoresis using a stepwise gradient of electric field strength, J. Chromatogr. A. 802(1):179–84 [1998]; N. J. Dovichi, DNA sequencing by capillary electrophoresis, Electrophoresis 18(12–13):2393–99 [1997]; H. Arakawa et al., Analysis of single-strand conformation polymorphisms by capillary electrophoresis with laser induced fluorescence detection, J. Pharm. Biomed. Anal. 15(9–10):1537–44 [1997]; Y. Baba, Analysis of disease-causing genes and DNA-based drugs by capillary electrophoresis. Towards DNA diagnosis and gene therapy for human diseases, J. Chromatgr B. Biomed. Appl. 687(2):271–302 [1996]; K. C. Chan et al., High-speed electrophoretic separation of DNA fragments using a short capillary, J. Chromatogr B. Biomed. Sci. Appl. 695(1):13–15 [1997]). Any of diverse fluorescent dyes can optionally be used to label primers of the present invention or amplification products for ease of analysis, including but not limited to, SYBR Green I, Y1O-PRO-1, thiazole orange, Hex (i.e., 6-carboxy-2',4',7',4,7- hexachlorofluoroscein), pico green, edans, fluorescein, FAM (i.e., 6-carboxyfluorescein), or TET (i.e., 4,7,2',7'-tetrachloro-6-carboxyfluoroscein). (E.g., J. Skeidsvoll and P. M. Ueland, Analysis of double-stranded DNA by capillary electrophoresis with laser-induced fluorescence detection using the monomeric dye SYBR green I, Anal. Biochem. 231(20):359–65 [1995]; H. Iwahana et al., Multiple fluorescence-based PCR-SSCP analysis using internal fluorescent labeling of PCR products, Biotechniques 21(30:510–14, 516–19 [1996]).

Analyzing the amplification products can also be done by means of restricting the amplification products with one or more restriction enzymes. When the amplification products comprise the normal locus of the HindIII recognition site in intron 8 of the human LPL gene, the restriction enzyme employed is preferably HindIII. Restriction of nucleic acids is followed by separation of the resulting fragments and analysis of fragment length or differential fragment migration in denaturing high-performance liquid chromatography (DHPLC) or gel electrophoresis, as above, including restriction-capillary electrophoresis. For example, this can be achieved by techniques known in the art, such as PCR-restriction fragment-SSCP, which can detect single base substitutions, deletions or insertions. (M. Tawata et al., A mass screening device of genome by polymerase chain reaction-restriction fragment-single strand conformation polymorphism analysis, Genet. Anal. 12(3–4):125–27 [1996]; H. H. Lee et al., Mutational analysis by a combined application of the multiple restriction fragment-single strand conformation polymorphism and the direct linear amplification DNA sequencing protocols, Anal. Biochem. 205(2) ;289–93 [1992]).

The present invention also relates to an oligonucleotide primer for detecting a genetic predisposition for non-responsiveness to statin drug treatment in a human. Useful oligonucleotide primers for amplifying the nucleic acids include any 15 to 28-mer nucleotide sequence that hybridizes with a nucleic acid fragment of the Nickerson or Oka reference sequences, under conventional conditions of stringency used for hybridization in PCR, and together in a set with another primer sequence amplifies a non-coding or untranslated region within the 3' end of the human LPL gene. A preferred primer is a 20 to 24-mer.

Useful for amplifying non-coding or untranslated nucleic acid sequences from intron 6 (beginning at position 5988 of the Nickerson reference sequence) through intron 9, is a set of oligonucleotide primers having nucleotide sequences that are fragments of the nucleotide sequences in GenBank accession numbers M76722 (below) and M76723 (opposite strand). The nucleotide sequence of M76722 is the following:

```
   1    TCTGCATTTT CTAGGTATGA ACACTGTGCA TGATGAAGTC TTTCCAAGCC              (SEQ.ID.NO.:81)

61    ACACCAGTGG TTCCATGTGT GTGCACTTCC GGTTTGAGTG CTAGTGAGAT ACTTCTGTGG

121    TTCTGAATTG CCTGACTATT TGGGGTTGTG ATATTTTCAT AAAGATTGAT CAACATGTTC

181    GAATTTCCTC CCCAACAGTC TTCCATTACC AAGTAAAGAT TCATTTTTCT GGGACTGAGA

241    GTGAAACCCA TACCAATCAG GCCTTTGAGA TTTCTCTGTA TGGCACCGTG GCCGAGAGTG

301    AGAACATCCC ATTCACTCTG TGAGTAGCAC AGGGGGGCGG TCATCATGGC ACCAGTCCCT

361    CTCCTGCCAT AACCCTTGGT CTGAGCAGCA GAAGCAGAGA GCGATGCCTA GAAAACAAGT

421    CTTTAGTTAA AAAAATCAGA ATTTCAAAAT TGAGGTCTTT CCTCTATTTG ATATTGAGAA

481    AAAAATGCTT CAAATTGGCC ATTTTATTTT CACTTACTAG TTATATTTTT TTATTTATCA

541    TCTTATATCT GTTTATTTCT TTTATAAAGC TGCTGTTAAA CAATATAATT AAACTATCTC

601    AAAAGGTTTG ACATTAAAGA AAATGAGCAA TGGTAACAGG AAACCACTCT ATAGATGTAC

661    ATATAATATG TACAGAAAAT ATAAGTAGTA AGAAGTCCAT GACAAAGTGT TAGCTCTTTT

721    TTTTTTTTTT TTTTTTTTTT TTTTTGAGAT GGAGTCTCTC TCTATTGCCC AGGCTGGAGT

781    GCAGTGATTC GATCTCAGCT CACTGCAACC TCTACCTCCC GAGTTCAAAC AATTCTTCTG

841    TCTCAGCCTC CCGAGTAGCT GGGGCTGCAG GTGCCCACCA CCATGCCCAG CTAATTTTTG

901    TATTTTTAGT AGCGACAGGG TCTCACCATG TTGGCCAAGC TGGTCTTGAA TTCCTGATCT

961    CAGGTGATCC ACCCGCCTCG GCCTCCCAAA GTGCTGGGAT TACAGGTGTG AGCCACCATG

1021    CCCAGCCTAC CCTTTACTAC TAATCAAAGA AATAAAGTA AGGCAACTTG ATACTTTTAC

1081    AATTACTAGA TGAACAAATC TTTAAAAATA GCCAGTGCAG ACAAGGTGGT GAAGCAGAAC

1141    ATGCGAACCT ACCATGCATC ATTCACGGCT AGAACCCTCC AGGTGCGGAA GGTAGTATTT

1201    TAATAACTTT CCATAGCTAC AAAATATTAT TACATAGAAG GGAGTGATTT TTTTCTAATA

1261    TTTATCCTAA AGAAATAGTC AACAAACATT TTTAAAAACA TCAATTACAG TCGTACCTAT

1321    ACTAGCATAA ATTAGAAACC CAGTATCCAA CATTGAGGCA GTGGGTAAAT GAATCGTGGT
```

```
                                      -continued
1381 TTATCAAGTC ATTAAAATCA ATCTAGCCTT TAAAAACTAT AATTGTAGGA AACCCAGGAA

1441 AACATAGTAA AAAATGGAAT ATAAAATCTG AAGAGAATAA AGAATAGAGA ATCGTATGTG

1501 TGCTATGATT GTAGCTAAAT AATGTTCAAG TATCAACACA AATTGAAAAG GAATACATGA

1561 AAATGAAAAT TATATTTCTG AATGATTGAC TTCAGGATTT TCTTTTAGAA TTGTATTAAA

1621 TAGTTCATGT CATTAGGATA AATGCTGAA TGTGGATATA ATTTAAAATA TACTAAATGC

1681 CATCGACCTT CATTTTGAGT TCTTTGTTGG ACATTTTTGT GCATTTTTAA AATATCCCCT

1741 AAATAATAAA GCTATTTATA TTTGGAGAGG AGAAAAAAAA GTGGGGGGCA GGGAGAGCTG

1801 ATCTCTATAA CTAACCAAAT TTATTGCTTT TTTGTTTAGG CCTGAAGTTT CCACAAATAA

1861 GACCTACTCC TTCCTAATTT ACACAGAGGT AGATATTGGA GAACTACTCA TGTTGAAGCT

1921 CAAATGGAAG AGTGATTCAT ACTTTAGCTG GTCAGACTGG TGGAGCAGTC CCGGCTTCGC

1981 CATTCAGAAG ATCAGAGTAA AAGCAGGAGA GACTCAGAAA AAGTAATTAA ATGTATTTTT

2041 CTTCCTTCAC TTTAGACCCC CACCTGATGT CAGGACCTAG GGGCTGTATT TCAGGGGCCT

2101 TCACAATTCA GGGAGAGCTT TAGGAAACCT TGTATTTATT ACTGTATGAT GTAGATTTTC

2161 TTTAGGAGTC TTCTTTTATT TTCTTATTTT TGGGGGGCGG GGGGGGAAGT GACAGTATTT

2221 TTGTATTTCA TGTAAGGAAA ACATAAGCCC TGAATCGCTC ACAGTTATTC AGTGAGAGCT

2281 GGGATTAGAA GTCAGGAATC TCAGCTTCTC ATTTGGCACT GTTTCTTGTA AGTACAAAAT

2341 AGTTAGGGAA CAAACCTCCG AGATGCTACC TGGATAATCA AAGATTCAAA CCAACCTCTT

2401 CCAGAAGGGT GAGATTCCAA GATAATCTCA ACCTGTCTCC GCAGCCCCAC CCATGTGTAC
```

For example, oligonucleotide primer sequences that are useful for amplifying nucleic acids that comprise the normal locus of the HindIII recognition site in LPL intron 8, include but are not limited to the following sequences (designation after the SEQ. ID. NO. includes the nucleotide position within M76722, e.g., 2701 or 2397, at which the 5'-terminus of the primer sequence begins if it is an upper ["U"; i.e., forward] primer; at which position complementary to a position within M76722 its 3'-terminus ends if it is a lower ["L"; i.e., reverse] primer; and the primer length, e.g., 24 bases):

```
5'-GCA TCT GCC TTC AGC TAG ACA TTG-3'(SEQ.ID.NO.:1;LPL HindIII:2701L24);

5'-TCT TCC AGA AGG GTG AGA TTC CAA-3'(SEQ.ID.NO.:2;LPL HindIII:2397U24);

5'-GGA AAA CAT AAG CCC TGA ATC-3'(SEQ.ID.NO.:3;LPL HindIII:2236U21);

5'-GAA AAC ATA AGC CCT GAA TCG-3'(SEQ.ID.NO.:4;LPL HindIII:2237U21);

5'-AAC ATA AGC CCT GAA TCG CTC-3'(SEQ.ID.NO.:5;LPL HindIII:2240U21);

5'-CCT GAA TCG CTC ACA GTT ATT-3'(SEQ.ID.NO.6:;LPL HindIII:2249U21);

5'-CTG AAT CGC TCA CAG TTA TTC-3'(SEQ.ID.NO.:7;LPL HindIII:2250U21);

5'-AAT CGC TCA CAG TTA TTC AGT-3'(SEQ.ID.NO.:8;LPL HindIII:2253U21);

5'-TTG GCA CTG TTT CTT GTA AGT-3'(SEQ.ID.NO.:9;LPL HindIII:2313U21);

5'-CAC TAT AGT TTG CAA AAT CCC-3'(SEQ.ID.NO.:10;LPL HindIII:2521L21);

5'-CAAACCTCC GAG ATG CTA CCT GGA-3'(SEQ.ID.NO.:11;LPL HindIII:2351U24);

5'-AGATGCTACCTG GAT AAT CAA AGA-3'(SEQ.ID.NO.:12;LPL HindIII:2361U24);

5'-GATGCTACC TGG ATA ATC AAA GAT-3'(SEQ.ID.NO.:13;LPL HindIII:2362U24);

5'-CTTCCAGAA GGG TGA GAT TCC AAG-3'(SEQ.ID.NO.:14;LPL HindIII:2398U24);

5'-CCAGAAGGGTGA GAT TCC AAG ATA-3'(SEQ.ID.NO.:15;LPL HindIII:2401U24);

5'-CAGAAGGGTGAG ATT CCA AGA TAA-3'(SEQ.ID.NO.:16;LPL HindIII:2402U24);
```

-continued

5'-CCCACCCAT GTG TAC CCA TAA AAT-3'(SEQ.ID.NO.:17;LPL HindIII:2446U24);

5'-CCACCCATG TGT ACC CAT AAA ATG-3'(SEQ.ID.NO.:18;LPL HindIII:2447U24);

5'-CCCATGTGT ACC CAT AAA ATG AAT-3'(SEQ.ID.NO.:19;LPL HindIII:2450U24);

5'-GTACCCATA AAA TGA ATT ACA CAG-3'(SEQ.ID.NO.:20;LPL HindIII:2457U24);

5'-CCCATAAAATGA ATT ACA CAG AGA-3'(SEQ.ID.NO.:21;LPL HindIII:2460U24);

5'-ATGAATTAC ACA GAG ATC GCT ATA-3'(SEQ.ID.NO.:22;LPL HindIII:2468U24);

5'-ACACAGAGA TCG CTA TAG GAT TTA-3'(SEQ.ID.NO.:23;LPL HindIII:2475U24);

5'-TTATAA CAT TTC CAT CCC CAA GAT-3'(SEQ.ID.NO.:24;LPL HindIII:2658L24);

5'-CATCTG CCT TCA GCT AGA CAT TGC-3'(SEQ.ID.NO.:25;LPL HindIII:2700L24);

5'-CTGCAT TAA GGA ATT AGG GCA TCT-3'(SEQ.ID.NO.:26;LPL HindIII:2719L24);

5'-AGATCA ACT CTG CCA TCT CTT AGC-3'(SEQ.ID.NO.:27;LPL HindIII:2745L24);

5'-TCT TAT GTT ACT GGG CTT TCA CCA-3'(SEQ.ID.NO.:28;LPL HindIII:2781L24);

5'-AGCCTA GAG CAG TCT TAT GTT ACT-3'(SEQ.ID.NO.:29;LPL HindIII:2793L24);

5'-CAGCCT AGA GCA GTC TTA TGT TAC-3'(SEQ.ID.NO.:30;LPL HindIII:2794L24);

5'-ACAGCC TAG AGC AGT CTT ATG TTA-3'(SEQ.ID.NO.:31;LPL HindIII:2795L24);

5'-AGACAGCCT AGA GCA GTC TTA TGT-3'(SEQ.ID.NO.:32;LPL HindIII:2797L24);

5'-CTTTATAACATTTCCATCCCCAAG AT-3'(SEQ.ID.NO.:35;LPL HindIII:2658L26);

5'-TGTACCCATAAAATGAATTACACAGA-3'(SEQ.ID.NO.:36;LPL HindIII:2456U26);

5'-ACCCATAAAATGAATTACACAGAGAT-3'(SEQ.ID.NO.:37;LPL HindIII:2459U26);

5'-AAAATGAATTACACAGAGATCGCTAT-3'(SEQ.ID.NO.:38;LPL HindIII:2465U26);

5'-TTACACAGAGATCGCTATAGGATTTA-3'(SEQ.ID.NO.:39;LPL HindIII:2473U26);

5'-CAGCCTAGAGCAGTCTTA TGT TAC T-3'(SEQ.ID.NO.:40;LPL HindIII:2793L25);

5'-ACAGCCTAGAGCAGTCTTATG TTA C-3'(SEQ.ID.NO.:41;LPL HindIII:2794L25);

5'-GACAGCCTAGAGCAGTCTTAT GTT A-3'(SEQ.ID.NO.:42;LPL HindIII:2795L25);

5'-ATAAAATGAATTACACAGAGATCGCTAT-3'(SEQ.ID.NO.:43;LPL HindIII:2463U28);

5'-AAGATTCTTTATAACATTTCCATC CC-3'(SEQ.ID.NO.:44;LPL HindIII:2664L26);

5'-AATTACACAGAGATCGCTATAGGATTTA-3'(SEQ.ID.NO.:45;LPL HindIII:2471U28);

5'-ACAGCCTAGAGCAGTCTTATGTTACT-3'(SEQ.ID.NO.:46;LPL HindIII:2793L26);

5'-CCC ACC CAT GTG TAC CCA T-3'(SEQ.ID.NO.:47;LPL HindIII:2446U19);

5'-CCA CCC ATG TGT ACC CAT-3'(SEQ.ID.NO.:48;LPL HindIII:2447U18);

5'-CAC CCA TGT GTA CCC ATA AAA-3'(SEQ.ID.NO.:49;LPL HindIII:2448U21);

5'-ACC CAT GTG TAC CCA TAA AA-3'(SEQ.ID.NO.:50;LPL HindIII:2449U20);

5'-GGC TTT CAC CAA GAG ATG ATA A-3'(SEQ.ID.NO.:51;LPL HindIII:2770L22);

5'-GGG CTT TCA CCA AGA GAT GAT A-3'(SEQ.ID.NO.:52;LPL HindIII:2771L22);

5'-TGA ATT ACA CAG AGA TCG CTA T-3'(SEQ.ID.NO.:53;LPL HindIII:2469U22);

5'-ACA GAG ATC GCT ATA GGA TTT A-3'(SEQ.ID.NO.:54;LPL HindIII:2477U22);

5'-GTT ACT GGG CTT TCA CC-3'(SEQ.ID.NO.:55;LPL HindIII:2782L17);5'-CTT ATG TTA CTG GGC TTT CA-3'(SEQ.ID.NO.:56;LPL HindIII:2784L20);

5'-TCT TAT GTT ACT GGG CTT TC-3'(SEQ.ID.NO.:57;LPL HindIII:2785L20);

5'-CCA CCC ATG TGT ACC CAT A-3'(SEQ.ID.NO.:58;LPL HindIII:2447U19);

-continued
```
5'-CAC CCA TGT GTA CCC ATA-3'(SEQ.ID.NO.:59;LPL HindIII:2448U18);

5'-ACC CAT GTG TAC CCA TAA-3'(SEQ.ID.NO.:60;LPL HindIII:2449U18);

5'-CCC ATG TGT ACC CAT AAA-3'(SEQ.ID.NO.:61;LPL HindIII:2450U18);

5'-CAA CTC TGC CAT CTC TTA GC-3'(SEQ.ID.NO.:62;LPL HindIII:2745L20);

5'-TCA ACT CTG CCA TCT CTT AG-3'(SEQ.ID.NO.;63;LPL HindIII:2746L20);

5'-ATC AAC TCT GCC ATC TCT TA-3'(SEQ.ID.NO.:64;LPL HindIII:2747L20);

5'-GAA AAC ATA AGC CCT GAA-3'(SEQ.ID.NO.:65;LPL HindIII:2237U18);

5'-AAA ACA TAA GCC CTG AAT C-3'(SEQ.ID.NO.:66;LPL HindIII:2238U19);

5'-ACA TAA GCC CTG AAT CG-3'(SEQ.ID.NO.:67;LPL HindIII:2241U17);

5'-CTG AAT CGC TCA CAG TT-3'(SEQ.ID.NO.:68;LPL HindIII:2250U17);

5'-TGA ATC GCT CAC AGT TAT T-3'(SEQ.ID.NO.:69;LPL HindIII:2251U19);

5'-ATC GCT CAC AGT TAT TCA G-3'(SEQ.ID.NO.:70;LPL HindIII:2254U19);

5'-TCG CTC ACA GTT ATT CAG T-3'(SEQ.ID.NO.:71;LPL HindIII:2255U19);

5'-CGC TCA CAG TTA TTC AGT G-3'(SEQ.ID.NO.:72;LPL HindIII:2256U19);

5'-AAT CCC AGC ACA TTT AGT AT-3'(SEQ.ID.NO.:73;LPL HindIII:2507L20);

5'-ACT ATA GTT TGC AAA ATC CC-3'(SEQ.ID.NO.:74;LPL HindIII:2521L20);

5'-TGA GAG CTG GGA TTA GAA-3'(SEQ.ID.NO.:75;LPL HindIII:2273U18);

5'-GAG AGC TGG GAT TAG AAG T-3'(SEQ.ID.NO.:76;LPL HindIII:2274U19);

5'-AGA GCT GGG ATT AGA AGT C-3'(SEQ.ID.NO.:77;LPL HindIII:2275U19);

5'-AAT CCC AGC ACA TTT AGT AT-3'(SEQ.ID.NO.:78;LPL HindIII:2507L20);

5'-CCC ACC CAT GTG TAC CCA TA-3'(SEQ.ID.NO.:79;LPL HindIII:2446U20).
```

Any 15- to 28-mer primer sequence overlapping any of SEQ. ID. NOS: 1–32 or 35–79 can also be used to amplify nucleic acids comprising the normal locus of the HindIII recognition site in LPL intron 8. The primer sequence can overlap the entire sequence of any of SEQ. ID. NOS.: 1–32 and 35–79, or can overlap at one or more contiguous nucleotide positions of any of SEQ. ID. NOS.: 1–32 and 35–79 and additional nucleotides adjacent to the position(s) based upon the Nickerson reference sequence.

Other primer sequences are useful for amplifying nucleic acid sequences including the (TTTA)$_n$ tetranucleotide repeat region in intron 6. These include SEQ. ID. NOS.:33 and 34, described above and the following primer sequences (designation includes the nucleotide position within the Nickerson reference sequence in Genbank accession AF050163, e.g., 4644 or 4934, at which the 5'-terminus of the primer sequence begins if it is an upper ["U"; i.e., forward] primer; or the position complementary to a position in AF050163 at which its 3'-terminus ends if it is a lower ["L"; i.e., reverse] primer; and primer length, e.g., 24 bases):

```
5'-CTG GAC AAG AGT CTA AAG CAG CAT-3'(SEQ.ID.NO.:82;LPL:4644U24);

5'-GAA TCG CTT GAA CCG GAA AG-3'(SEQ.ID.NO.:83;LPL:4934L20:);

5'-ACC ATC AGT CTT AAG AGA TCT GTG-3'(SEQ.ID.NO.:84;LPL:4934L24);

5'-CAC AGA TCT CTT AAG ACT GAT GGT-3'(SEQ.ID.NO.:85;LPL:4693L24);

5'-TTT TTC ACC TGG ACA AGA GT-3'(SEQ.ID.NO.:86;LPL:4636U20);

5'-GGG TAA CTG AGC GAG ACC GT-3'(SEQ.ID.NO.:87;LPL:4870L20);

5'-TTC ACC TGG ACA AGA GTC TA-3'(SEQ.ID.NO.:88;LPL:4639U20);

5'-GCT TGA ACC GGA AAG-3'(SEQ.ID.NO.:89;LPL:4934L15);

5'-TCA CCT GGA CAA GAG TCT AA-3'(SEQ.ID.NO.90;LPL:4640U20);

5'-CTC CAG CCT GGG TAA CT-3'(SEQ.ID.NO.:91;LPL:4882L17);

5'-ACA AGA GTC TAA AGC AGC AT-3'(SEQ.ID.NO.92;LPL:4648U20); and
```

Any 15- to 28-mer primer sequence overlapping any of SEQ. ID. NOS:37 and 38 or 82–92 can also be used to amplify nucleic acids comprising the $(TTTA)_n$ tetranucleotide repeat region in LPL intron 6. The primer sequence can overlap the entire sequence of any of SEQ. ID. NOS.:33–34 and 82–92, or can overlap at one or more contiguous nucleotide positions of any of SEQ. ID. NOS.:33–34 and 82–92 and additional nucleotides adjacent to the position(s) based upon the Nickerson reference sequence.

Other primer sequences are useful for amplifying nucleic acid sequences in exon 10 and the 3'-UTR. These include the following primer sequences (SEQ. ID. NOS.:95–106) (designation includes the nucleotide position within the Oka reference sequence in GenBank accession X52978 X53518, e.g., 2564, at which the 5'-terminus of the primer sequence begins if it is an upper ["U"; i.e., forward] primer; or the position complementary to a position in X52978 X53518 at which its 3'-terminus ends if it is a lower ["L"; i.e., reverse] primer; and primer length, e.g., 22 bases):

The present invention also relates to a primer set for detecting a genetic predisposition for non-responsiveness to statin drug treatment in a human. The primer set functions to initiate nucleic acid synthesis in PCR from both the 5' and 3' ends of a nucleic acid template comprising a non-coding or untranslated region of the 3' end of the human LPL gene. The primer set comprises any two suitable oligonucleotide primers of the present invention, as described herein, as long as the primer set includes both a forward (upper or "U") and a reverse (lower or "L") primer.

For example, a preferred primer set for amplifying nucleic acids comprising the normal locus of the HindIII recognition site in intron 8 of LPL includes any pair lower and upper primers from among SEQ. ID. NOS.:1–36 or 39–83 (described above), or primer sequences overlapping any of them with respect to the Nickerson reference sequence. A most preferred set of primers is reverse (lower) primer SEQ. ID. NO.:1 and forward (upper) primer SEQ. ID. NO.:2.

Additional primer sets that are useful for amplifying the region of the $(TTTA)_n$ tetranucleotide repeat include any

```
5'-ATG AAA AGA GCA TAT GGT GGT T-3'(SEQ.ID.NO.95;LPL 3'end Oka

2564U22);

5'-TGG CCC AGG TAT ACA TAT GTA ACT A-3'(SEQ.ID.NO.96;LPL 3'end Oka

2845L25);

5'-GGC CCA GGT ATA CAT ATG TAA CTA A 3'(SEQ.ID.NO.97;LPL-3'end Oka

2844L25);

5'-TGA AAA GAG CAT ATG GTG GTT C 3'(SEQ.ID.NO.98;LPL-3'end Oka

2565U22);

5'-GAA AAG AGC ATA TGG TGG TTC-3'(SEQ.ID.NO.99;LPL 3'end Oka 2566U21);

5'-GCC CAG GTA TAC ATA TGT AAC TAA C-3'(SEQ.ID.NO.100;LPL 3'end Oka

2843L25);

5'-AAA AGA GCA TAT GGT GGT TC-3'(SEQ.ID.NO.101;LPL 3'end Oka2567U20);

5'-GGT TCT CTC AGC TCC CAG CCA ACA A-3'(SEQ.ID.NO.102;LPL 3'end Oka

2582U25);

5'-AGC ACA CCA ACA TGG CCC AGG TA-3'(SEQ.ID.NO.103;LPL 3'end Oka

2869L23);

5'-CTC AGC TCC CAG CCA ACA ACC AGT C-3'(SEQ.ID.NO.104;LPL 3'end Oka

2588U25);

5'-CAG CAC ACC AAC ATG GCC CAG GTA-3'(SEQ.ID.NO.105;LPL 3'end Oka

2859L24); and

5'-AGC TCC CAG CCA ACA ACC AGT CTC G-3'(SEQ.ID.NO.106;LPL 3'end Oka

2591U25).
```

Any 15- to 28-mer primer sequence overlapping any of SEQ. ID. NOS: 95–106 with respect to its position on the Oka reference sequence can also be used to amplify nucleic acids comprising LPL exon 10 and the 3'UTR. The primer sequence can overlap the entire sequence of any of SEQ. ID. NOS.:95–106 or can overlap at one or more contiguous nucleotide positions of any of SEQ. ID. NOS.:95–106 and additional nucleotides adjacent to the position(s) based upon the Oka reference sequence.

pair of lower and upper primers from among SEQ. ID. NOS.:33–34 and 82–92 (described above), or primer sequences overlapping any of them with respect to the Nickerson reference sequence. A most preferred embodiment of a primer set for detecting the presence of the $(TTTA)_n$ 4 allele includes primers comprising SEQ. ID. NOS.:33 and 34.

Additional primer sets that are useful for amplifying exon 10 and the 3'UTR include any pair of lower and upper primers from among SEQ. ID. NOS.:95–106 (described above), or primer sequences overlapping any of them with respect to the Oka reference sequence.

The present invention also relates to a genetic testing kit for detecting in a human subject a genetic predisposition for non-responsiveness to statin drug treatment. The genetic testing kit is a ready assemblage of materials for facilitating the amplifying of nucleic acids from a human subject comprising a nucleotide sequence from a non-coding or untranslated region of the 3' end of the human LPL gene and/or analyzing amplification products thereof. A genetic testing kit of the present invention contains at least one oligonucleotide primer of the present invention and preferably comprises a primer set of the present invention, as described above, together with instructions for the practice of the present method. The materials or components assembled in the genetic testing kit are provided to the practitioner stored in any convenient and suitable way that preserves their operability and utility. For example the components can be in dissolved, dehydrated, or lyophilized form; they can be provided at room, refrigerated or frozen temperatures.

Another preferred embodiment of the genetic testing kit incorporates an array of oligonucleotide primers specific for single nucleotide polymorphisms in the human nucleotide sequence of the 3' end of LPL, particularly of non-coding or untranslated regions, preassembled in a "DNA chip" (or "gene chip") configuration for facilitating the amplifying of nucleic acids and the analyzing of amplification products. (E.g., J. G. Hacia et al., Enhanced high density oligonucleotide array-based sequence analysis using modified nucleoside triphosphates, Nucleic Acids Res. 26(2):4975–82 [1998]); R. W. Wallace, DNA on a chip: serving up the genome for diagnostics and research, Mol. Med. Today 3(9):384–89 [1997]; T. Pastinen et al., Minisequencing: a specific tool for DNA analysis and diagnostics on oligonucleotide arrays, Genome Res. 7(6):606–14 [1997]); M. T. Cronin et al., Cystic fibrosis mutation detection by hybridization to light-generated DNA probe arrays, Hum. Mutat. 7(3):244–55 [1996]; A. C. Pease et al., Light-generated oligonucleotide arrays for rapid DNA sequence analysis, Proc. Natl. Acad. Sci. USA 91(11):5022–26 [1994]; E. M. Southern et al., Arrays of complementary oligonucleotides for analyzing the hybridisation behaviour of nucleic acids, Nucleic Acids Res. 22(8):1368–73 [1994]).

The skilled practitioner will appreciate that homozygosity for a mutation in a non-coding or untranslated region of the 3' end of the human LPL gene such as the HindIII 2/2 or (TTTA)$_n$ 4/4 genotypes, is a risk factor for atherosclerotic stenosis in coronary artery disease independent and additive to the use of statin drugs to reduce LDL. For example, the effect of the LPL HindIII 2/2 genotype on atherosclerotic graft worsening is of the same magnitude as the use of moderate rather than aggressive drug therapy to lower LDL. Such a genotype apparently does not act via an effect on lipid levels, nor the amount of drug needed to achieve lower levels. However, it is associated with a modest effect on blood pressure.

Using the methods, primers, primer sets, and genetic testing kits of the present invention for detecting a genetic predisposition in a human for non-responsiveness to statin drug treatment for coronary artery disease, the practitioner can identify patients homozygous for a variant allele in a non-coding or untranslated region of the 3' end of LPL, for example those with the HindIII 2/2 or (TTTA)$_n$ 4/4 genotype. These patients are predisposed to develop atherosclerotic progression despite their compliance with aggressive lipid lowering therapy with lovastatin or other statin class drugs.

A high level of LDL-C is an important risk factor of heart disease and atherosclerosis, but it is not the sole risk factor. The present invention provides the practitioner a valuable tool for better characterizing individual patients and identifying those patients likely to need individualized alternative interventions other than LDL-C lowering therapy with statin class drugs. For example, direct blood pressure lowering therapy may be indicated for patients identified as homozygous for a variant genotype in accordance with the present invention, because they tend to have blood pressures at the high end of the normal range. Such treatment can include, for example, angiotensinogen converting enzyme (ACE) inhibitors or $Ca^{2+}$ channel blockers. Alternatively, beta blockers, diuretics, or a combination of modalities can be a more appropriate blood pressure lowering therapy for a given patient. Blood pressure lowering in conjunction with aspirin treatment can prevent heart disease in some patients. (See L. Hansson et al., Effects of intensive blood-pressure lowering and low-dose aspirin in patients with hypertension: principle results of the hypertension Optimal Treatment [HOT] randomised trial, Lancet 351(9118):1755–62 [1998]; Thrombosis prevention trial: randomised trial of low-intensity oral anticoagulation with warfarin and low-dose aspirin in the primary prevention of ischemic heart disease in men at increased risk, Lancet 351(9098):233–41 [1998]).

For patients identified as homozygous for a variant allele in accordance with the present invention, the practitioner can look at a variety of other known or suspected atherogenic risk factors, beyond LDL-C levels, that may be amenable to treatment in an individual patient. For example, small LDL particle sizes may be amenable to treatment with fibric acid-derivative drugs, e.g., lopid, or high dose niacin. (See J. R. Guyton et al., Effectiveness of once-nightly dosing of extended-release niacin alone and in combination for hypercholesterolemia, Am. J. Cardiol. 82(6):737–43 [1998]). High Lp(a) levels may be treatable with niacin, or estrogen replacement therapy in women or testosterone replacement in men.

For some patients identified as homozygous for a variant allele in accordance with the present invention, such as the HindIII 2/2 or (TTTA)$_n$ 4/4 genotype, the practitioner can appropriately focus on altering atherogenic life style factors such as diet, smoking, and exercise. (E.g., see J. C. LaRosa, The role of diet and exercise in the statin era, Prog. Cardiovasc. Dis. 41(2):137–50 [1998]).

In view of the substantial cost of statin drugs, a secondary benefit to be derived from identifying patients having a genetic predisposition to non-responsiveness to statin drug treatment, for coronary artery disease or high blood pressure, is the cost savings to patients and health care systems that can be gained by relying on more individually suited alternative treatments instead of statin treatment regimens, for those individuals for whom statins are likely to be ineffective. (See D. M. Huse et al., Cost-effectiveness of statins, Am. J. Cardiol. 82(11):1357–63 [1998]; P. N. Durrington, Can we afford to treat hyperlipidaemia as we should? Strategies for rational treatment, Atherosclerosis 139(Suppl. 1):S1–5 [1998]; J. A. Farmer, Economic implications of lipid-lowering trials: current considerations in selecting a statin, Am J. Cardiol. 82(6A):26M–31M [1998]).

By using the methods, primers, primer sets, and genetic testing kits of the present invention, the practitioner can better individualize the treatment and improve the care of patients with coronary artery disease.

The detailed examples which follow describe the genetic association between variant alleles in non-coding or untranslated regions of the 3' end of the human LPL gene and atherosclerotic stenosis in coronary artery disease that is non-responsive to statin drug treatment. These examples are intended merely to illustrate and in no way limit the present invention.

EXAMPLES

Genetic Link Between Mutant LPL Genotypes and Phenotypic Atherosclerotic Stenosis in Coronary Artery Disease that is Non-responsive to Statin Drug Treatment The following examples describe further data and analyses that support a genetic association between the LPL HindIII 2/2 or $(TTTA)_n$ 4/4 genotypes and a phenotype of atherosclerotic stenosis in coronary artery disease that is non-responsive to statin drug treatment.

Example 1

Study Design

A genetic association study was conducted by a within-case comparison ancillary to the Post Coronary Artery Bypass Graft Trial. (The Post Coronary Artery Bypass Graft Trial Investigators. The effect of aggressive lowering of low-density lipoprotein cholesterol levels and low-dose anticoagulation on obstructive changes in saphenous-vein coronary-artery bypass grafts, N. Engl. J. Med. 336:153–62 [1997]). A two stage design was followed. First, EBV-transformed lymphoblastoid cell lines were established for subjects from the Los Angeles (L.A.) cohort providing a permanent source of DNA for testing hypotheses related to atherosclerosis-related candidate genes. Then, significant results were tested in a second stage by genotyping all available subjects in the post-CABG trial using DNA isolated from whole blood shipped to Cedars-Sinai Medical Center from the other participating centers.

Participants were randomly assigned, following a two by two design, to receive 1) lovastatin therapy to lower the LDL-cholesterol level to within the range of 93–97 mg/dl (aggressive treatment group) or 132–136 mg/dl (moderate treatment group), and 2) placebo or low-dose warfarin (Post-CABG, 1997). Coronary angiograms of 1351 subjects at enrollment and an average of 4.3 years later were compared using a quantitative assessment of the severity of graft stenosis. Graft worsening was defined as a decrease in lumen diameter of 0.6 mm or more. The percentage of subjects with worsening of one or more grafts was 39% in the aggressive treatment group compared to 51% in the moderate treatment group (p<0.001) and the mean percentage of grafts per patient showing worsening was 27% in the aggressive treatment group compared to 39% in the moderate treatment group (p<0.001).

These results demonstrated the efficacy of lowering LDL-cholesterol levels with statin drug treatment in reducing the risk of graft worsening in most CABG patients. No effect of the warfarin treatment on graft worsening was observed.

Example 2

Subjects

A total of 1351 subjects from seven clinical centers throughout North America were included in the clinical trial and all were eligible as participants. Genetic material was received from 891 subjects who were included in this ancillary study. Inclusion criteria for the clinical trial were: bypass surgery 1–11 years prior to the study; an LDL-cholesterol level of 130–175 mg/dl; and at least one patent vein graft as determined by angiography. Subjects were excluded if there was: (a) the likelihood of revascularization or death within the study period of 5 years; (b) unstable angina or myocardial infarction within six months before the start of the trial; (c) severe angina; (d) heart failure; or (e) contraindications to the study medications. Id. Subjects were randomly assigned in a two by two factorial design for treatment to lower LDL-cholesterol levels aggressively (target LDL 93–97 mg/dl) or moderately (target LDL 132–136 mg/dl) with lovastatin and cholestyramine if needed, and for treatment with either placebo or warfarin sufficient to maintain an international normalized ratio of less than 2. Id. Graft worsening was determined by comparing the initial angiogram at enrollment with a follow-up angiogram repeated an average of 4.3 years later. "Worsening" was defined as a reduction in diameter $\geq 0.6$ mm in diameter. "Subjects with worsening" were defined as those subjects with one or more grafts showing worsening.

Example 3

Data Collection

Questionnaire data regarding demographics, family and medical history, and angiographic and clinical data were collected as part of the post-CABG trial. Additional family history data were collected from 891 subjects in the genetic ancillary study.

Example 4

DNA

During years 2–3 of the clinical trial, cell lines from 224 subjects in the L.A. cohort were established by transformation of peripheral blood lymphocytes with Epstein-Barr virus (EBV). (M. A. Anderson and J. F. Gusella, Use of cyclosporin-A in establishing Epstein-Barr virus transformed human lymphoblastoid cell lines. In Vitro 21:856–58 [1984]; S. Pressman and J. I. Rotter, Epstein-Barr virus transformation of cryopreserved lymphocytes, prolonged experience with technique, letter to the editor, Am. J. Hum. Genet. 49:467 [1991]). During years 4–5, whole blood was collected from an additional 667 subjects from the other centers. Thus, DNA was available from a total of 891 subjects. DNA was isolated following standard protocols. (B. G. Herrman and A. Frischauf, Isolation of Genomic DNA, Methods in Enzymology 152:180–83 [1987]).

Example 5

Genotyping

Conventional agarose gel techniques were used to genotype the LA cohort for the biallelic LPL HindIII polymorphism following Heizmann et al. (C. Heizmann et al., RFLP for the human lipoprotein lipase (LPL) gene. HindIII, Nucleic Acids Res. 15:6763 [1987]). DNA samples from the remaining subjects were genotyped for this polymorphism as well as four additional LPL polymorphisms using fluorescent semi-automated technology. In FIG. 1(a), the location of polymorphisms in the LPL gene was assembled from information in GenBank, accession numbers G 187209, G34390, M76722, and M76723, and other published sources. (F. Mailly et al., A common variant in the gene for lipoprotein lipase (asp9-asn). functional implications and prevalence in normal and hyperlipidemic subjects, Arterioscler. Thromb. Vasc. Biol. 15:468–78 [1995]; P. W. A. Reymer et al., A lipoprotein lipase mutation (asn291ser) is associated with reduced HDL cholesterol levels in premature atherosclerosis, Nat Genet 1995;10:28–34 [1995]; C. Heizmann et al., DNA polymorphism haplotypes of the human lipoprotein lipase gene: possible association with high density lipoprotein levels, Hum. Genet. 86:578–84 [1991]; G. Zuliani and H. H. Hobbs, Tetranucleotide repeat polymorphism in the LPL gene, Nucleic Acids Res. 18:4958 [1990]).

Marker genotypes were determined using a PCR with primers listed below as recommended by the manufacturer of Ampli-Taq Gold (Perkin Elmer, Foster City, Calif.) in a Perkin Elmer 9600 thermocycler. (All PCR runs began with 95° for 10 min. to activate the polymerase). After digestion with the appropriate restriction enzyme, PCR products for each subject were pooled from all five genotyping reactions and run together on 6% Long Ranger gels in a semi-automated DNA sequencer (ABI 373 DNA sequencer, Applied Biosystems, Foster City, Calif.) with gel processing using Genescan and Genotyper software.

D9N (exon 2). The assay of Mailley et al. (1995) was redesigned using the sequence in GenBank accession G187209 so that the forward primer (5'-Hex-ACT CCG GGA ATG AGG T; SEQ. ID. NO.:107) carried the detection dye and the reverse primer (CCA GAA AGA AGA GAT TTT GTC; SEQ. ID. NO.:108) introduced a SalI restriction site if the PCR fragment carried the mutated D9N allele, and resulted in a 98 bp fragment for the D allele (1 allele) and a 77 bp fragment for the N allele (2 allele) after SalI digestion. PCR conditions were 35 cycles of 94° C. 30 sec, 46° C. 30 sec, 72° C. 30 sec.

N291S (exon 6). The procedure of Reymer et al. (1995) was followed with Hex added to the forward primer. PCR conditions were 35 cycles of 94° C. 30 sec, 60° C. 30 sec, 72° C. 30 sec. The reverse primer introduces a partial RsaI site so that the N allele gave a 242 bp fragment (1 allele) and the S allele gave a 218 bp fragment (2 allele) after the RsaI digestion.

PvuII (intron 6). The assay of Li et al. (S. Li et al., PvuII RFLP at the human lipoprotein [LPL] gene locus, Nucleic Acids Res. 16:2358 [1988]) was redesigned using the sequence in GenBank accession number g34390 so that the resulting fragments would run less than 350 bp in size on the ABI 373. The forward primer was 5'-Tet-CTG CTT TAG ACT CTT GTC CAG GTG (SEQ. ID. NO.:109) and the reverse primer was 5'-GGG TTC AAG GCT CTG TCA GTG TCC (SEQ. ID. NO.:110) PCR conditions were 35 cycles of 94° C. 30 sec, 55° C. 30 sec, 72° C. 30 sec. A 155 bp fragment was detected if the PvuII site was present (1 allele) and a 282 bp fragment was detected if the PvuII site was absent (2 allele).

$(TTTA)_n$ (intron 6). The procedure of Zuliani and Hobbs (1990) was followed using FAM-labeled GZ-15 primer (5'-CCT GGG TAA CTG AGC GAG ACT GTG TC-3'; SEQ. ID. NO.:33) and GZ-14 primer (5'-ATC TGA CCA AGG ATA GTG GGA TAT A-3'; SEQ. ID. NO.:34). PCR conditions were 35 cycles of 94° C. 30 sec, 68° C. 3 min. Allele 1 ran at a size of 119 bp, 2 at 123 bp, 3 at 127 bp, 3 at 127 bp, 4 at 131 bp, and 5 at 135 bp.

HindIII (intron 8). The assay of Heinzmann et al. (1987) was used for stage 1 and then was redesigned for stage 2 using the sequence in GenBank accession numbers M76722 and M76723. Reverse primer was 5'-Fam-GCA TCT GCC TTC AGC TAG ACA TTG (SEQ. ID. NO.:1) and forward primer was 5'-TCT TCC AGA AGG GTG AGA TTC AAA (SEQ. ID. No.:2). PCR conditions were the same as described above for PvuII. Using this primer set of SEQ. ID. NOS.:1 and 2, a 228 bp fragment was detected if the HindIII restriction site was present (1 allele) and a 330 bp fragment if absent (2 allele).

Example 6

Statistical Methods

Differences in baseline characteristics between treatment groups and between genotype groups were tested by one-way analysis of variance or Chi-square tests. Log-transformed HDL and TG values were used to perform all statistical analyses in order to adjust for their skewed distributions, but are presented in the tables as untransformed means±SE. The association between graft worsening and LPL genotype was tested by Chi-square test. Mantel-Haenszel statistics were used for testing the interactions between genotypes and treatment groups. The proportion of grafts showing worsening per subject was used as the quantitative measurement of graft worsening, and multiple regression was performed to for this proportion as a function of genotype and treatment group to identify predictors. Adjusted variables for this trait included age, gender, body mass index, smoking status, number of years since CABG, systolic and diastolic blood pressure, current medicine use, and family history as listed in Table 1. All statistical analyses were carried out with SAS software (version 6.12, SAS Institute, Cary, N.C.).

Example 7

Baseline Characteristics

Table 1(a) compares the baseline characteristics of the subjects in the aggressive and moderate drug treatment groups. Minor differences were observed in the percent of subjects with a history of stroke, percent using diabetic therapies, systolic and diastolic blood pressures, and baseline LDL levels. The highly significant difference in the steady state levels of total cholesterol and LDL-cholesterol between these two groups reflects the effect of the drug treatment. As shown in Table 1(b), significant differences were observed between the 891 subjects in the genetic study and the 460 subjects who were not included: frequency of prior myocardial infarction, 46% vs. 55%, p=0.001; smoking 9% vs. 14%, p=0.005; mean years from CABG to enrollment, 4.7 vs. 5.2 years, p<0.001; and aspirin use, 79% vs. 69%, p=0.001.

TABLE 1

Characteristics of Subjects by Treatment Group (1a) or by Inclusion or Exclusion in Genetic Study (1b).

| Characteristic | 1a: By Treatment Group | | | 1b: By Inclusion or Exclusion in Genetic Study | | |
|---|---|---|---|---|---|---|
| | Aggressive (N = 430) | Moderate (N = 406) | p | Included (N = 891) | Excluded (N = 460) | p |
| Age (yr, mean(SE) | 62.2 ± 0.4 | 61.5 ± 0.4 | | 62 | 61 | |
| Caucasian (%) | 94 | 96 | | 94 | 96 | |
| Male (%) | 91 | 92 | | 92 | 93 | |
| Body mass index (kg/m$^2$, mean(SE) | 27.2 ± 0.2 | 27.3 ± 0.2 | | | | |
| Current smoking (%) | 15 | 9 | | 9 | 14 | 0.005 |
| History of myocardial infarction (%) | 45 | 48 | | 46 | 55 | 0.001 |
| Time between CABG and enrollment (yr, mean(SE) | 4.7 ± 0.1 | 4.8 ± 0.1 | | 4.7 | 5.2 | <0.001 |
| Ejection fraction (%): | 56 | 57 | | 57 | 57 | |
| Family history of (%): | | | | | | |
| Coronary artery disease | 76 | 70 | | 70 | 71 | |
| Diabetes | 36 | 33 | | * | | |

TABLE 1-continued

Characteristics of Subjects by Treatment Group (1a) or by Inclusion or Exclusion in Genetic Study (1b).

| Characteristic | 1a: By Treatment Group | | | 1b: By Inclusion or Exclusion in Genetic Study | | |
|---|---|---|---|---|---|---|
| | Aggressive (N = 430) | Moderate (N = 406) | p | Included (N = 891) | Excluded (N = 460) | p |
| Hypertension | 58 | 56 | | | | |
| Peripheral vascular disease | 19 | 21 | | | | |
| Stroke | 41 | 48 | | | | 0.05 |
| Current medications (%): | | | | | | |
| Aspirin | 82 | 77 | | 79 | 69 | 0.001 |
| Beta-blocker | 25 | 24 | | 24 | 26 | |
| Calcium-channel blocker | 27 | 21 | | 24 | 23 | |
| Insulin or oral antidiabetic agent | 10 | 6 | 0.03 | 10 | 8 | |
| Thiazide diuretic | 12 | 9 | | 11 | 11 | |
| Systolic blood pressure (mmHg, mean(SE) | 134.4 ± 0.8 | 133.0 ± 0.9 | 0.03 | 134.0 | 134.8 | |
| Diastolic blood pressure (mmHg, mean(SE) | 79.3 ± 0.4 | 79.7 ± 0.4 | 0.02 | 79.6 | 80.1 | |
| Baseline lipid levels (mg/dl):† | | | | | | |
| Total cholesterol | 227.3 ± 1.2 | 227.4 ± 1.3 | | 226.9 | 226.4 | |
| LDL cholesterol | 156.1 ± 1.0 | 155.3 ± 1.0 | 0.04 | 155.3 | 155.8 | |
| HDL cholesterol | 39.3 ± 0.5 | 39.5 ± 0.5 | | 39.4 | 39.0 | |
| Triglycerides | 160.3 ± 73.2 | 162.2 ± 3.7 | | 161.1 | 157.6 | |
| Steady state lipid levels (mg/dl): | | | | | | |
| Total cholesterol | 172.6 ± 1.6 | 209.5 ± 1.6 | 0.001 | 191.1 | 194.3 | |
| LDL cholesterol | 97.1 ± 1.3 | 133.0 ± 1.3 | 0.001 | 120.4 | 114.6 | 0.002 |
| HDL cholesterol | 44.9 ± 0.6 | 43.7 ± 0.6 | | 44.3 | 42.0 | 0.001 |
| Triglyecrides | 157.4 ± 4.5 | 164.5 ± 4.4 | | 163.1 | 160.6 | |

Drug treatment groups and included/excluded in genetic study groups were compared by the analysis of variance.
Blank p values were nonsignificant.
For the LPL HindIII genotype, "1" indicates the presence, "2" the absence, of the restriction site in intron 8.
Complete data for every category in this table was available for 836 of the 891 subjects in this study.
*Comparable family histoty data is unavailable on subjects that were not included in the genetic study and so these groups cannot be compared for these characteristics.
†Values listed are those measured most recently before enrollment.
To convert cholesterol values to mmol/l, multiply by 0.02586; to convert triglyceride values to mmol/l, multiply by 0.01129.

Example 8
LPL HindIII and Graft Worsening in L.A. Cohort

Genotyping of the L.A. cohort for the LPL HindIII polymorphism demonstrated that the proportion of subjects with graft worsening increased with the number of HindIII 2 alleles: 42% in those with no HindIII 2 allele, 54% in those with one, and 72% in those with two ($X^2$ 2×3 test of association, p=0.05). Further, the percent of grafts showing worsening was calculated per subject and the mean of this percentage also increased with the number of LPL HindIII 2 alleles, with 22% in the subjects with HindIII 1/1, 31% in subjects with 1/2, and 53% in subjects with 2/2 (analysis of variance, p=0.001).

Example 9
LPL HindIII and Graft Worsening in All Subjects

With this result, the remaining 667 subjects were genotyped. A comparison of the percent of subjects with graft worsening for the two LPL HindIII genotypes for all 891 subjects is shown in Table 2. A significant difference in the percent of subjects showing graft worsening was observed between those with the LPL HindIII 2/2 genotype compared to those with the LPL HindIII 1/1 and 1/2 genotypes combined; 58% of those with the LPL HindIII 2/2 genotype exhibited worsening compared with 42% of those with either 1/1 or 1/2 (odds ratio=1.9, 95% confidence interval 1.2–3.2, p=0.011). The mean proportion of grafts showing worsening per subject was also significantly increased for those with the LPL HindIII 2/2 genotype (40% for HindIII 2/2 compared with 27% for LPL HindIII 1/1 and 1/2; p=0.0066). There were no significant differences in graft worsening between subjects with the LPL HindIII 1/1 and 1/2 genotypes.

TABLE 2

Graft Worsening and LPL HindIII Genotype.

| | LPL HindIII Genotype | | |
|---|---|---|---|
| Phenotype | 2/2 (N = 65) | 1/1 & 1/2 (N = 723) | p value |
| Subjects with Worsening (%) | 58 | 41 | 0.011 |
| Mean Grafts with Worsening/Subject (%) | 40 | 27 | 0.0066 |

"Subjects with worsening" defined as subjects with one or more grafts showing worsening, defined as a decrease (0.6 mm in vessel diameter; "mean grafts with worsening/subject" defined as the mean number of grafts showing worsening/total number of grafts per subject. Complete worsening data were available for 788 subjects.
"Subjects with worsening" were compared using the Chi square test of association;
"mean grafts with worsening/subject" were compared using analysis of variance.
For the LPL HindIII genotype, "1" indicates the presence, "2" the absence, of the restriction site in intron 8.

Example 10
LPL Genotypes and Graft Worsening

Four additional LPL polymorphisms were tested for association with graft worsening in the entire genetic study cohort (FIG. 1). Complete worsening data were available for 792 subjects; complete genotyping data for each marker represented in FIG. 1: D9N (exon 2; Mailley et al. [1995], N291S (exon 6; Reymer et al. [1995]), PvuII (intron 6; "1"=site is present, "2"=site is absent; S. Li et al.[1988]), $(TTTA)_n$ (intron 6; allele 1 is 119 bp, 2 is 123 bp, 3 is 127 bp, 4 is 131 bp, 5 is 135 bp; D.-A. Wu et al., Quantitative trait locus mapping of human blood pressure to a genetic region at or near the lipoprotein gene locus on chromosome 8p22, J. Clin. Invest. 97:2111–18 [1996]), HindIII (intron 8; "1"=site is present, "2"=site is absent; C. Heizmann et al. [1987]). A designation of "X" is an abbreviation for "other" genotypes. The percent of subjects with graft worsening is the percent of subjects with one or more grafts showing a reduction in diameter $\geq 0.6$ mm.

Only the $(TTTA)_n$ and HindIII polymorphisms were significantly associated with graft worsening by the Chi square test of association. There was no association between graft worsening and the functional D9N and N291S polymorphisms and also no association with the PvuII polymorphism. In contrast, the 4/4 genotype of the $(TTTA)_n$ polymorphism was associated with graft worsening: 63% of $(TTTA)_n$ 4/4 subjects had worsening of one or more grafts compared to 43% of subjects with other $(TTTA)_n$ genotypes (OR=2.2, 95% CI 1.1–4.6; p=0.027). The $(TTTA)_n$ 4 allele was found to be in strong linkage disequilibrium with the HindIII 2 allele (p<0.001, data not shown). Consequently, the combined genotype of $(TTTA)_n$ 4/4 and HindIII 2/2 was also associated with graft worsening at a significance level similar to the $(TTTA)_n$ 4/4 or HindIII 2/2 genotypes alone.

Graft worsening was significantly associated with the LPL HindIII 2/2 genotype and tetranucleotide $(TTTA)_n$ 4/4 polymorphisms, both individually and together. The LPL HindIII 2/2 polymorphism did not appear to be acting through any lipid variables, but was associated with significant differences in systolic and diastolic blood pressure.

In contrast, no associations between clinical endpoints and the LPL D9N, N291S, or PvuII polymorphisms were observed, indicating that the as yet unknown functional mutation associated with graft worsening is in linkage disequilibrium with the $(TTTA)_n$ and HindIII polymorphisms, and thus resides in the 3'-end of the LPL gene.

Multiple regression analysis demonstrated that there were no differences in the baseline or steady-state serum lipid values, or the response to lipid-lowering therapy between those subjects with the LPL HindIII 2/2 genotype and those with the other HindIII genotypes (i.e., 1/1 or 1/2). While the present invention is not committed to any particular mechanism, this observation indicates that the LPL polymorphism does not act through an effect on LDL-cholesterol. This result is congruent with that of Peacock et al. (1992) who observed an association between the LPL HindIII 2 allele and the angiographic severity of atherosclerosis without observing concomitant differences in the mean fasting serum lipid levels in a comparison of young myocardial infarction survivors and age-matched controls.

Some significant differences in important risk factors for atherosclerosis were observed among the group of subjects in the genetic study described herein, including: the frequency of prior myocardial infarction, smoking, aspirin use, and mean years from CABG to enrollment. But if a survival bias occurred, it would lead to an underestimate of the effect of the LPL HindIII 2/2 genotype on the risk of graft worsening. Further, in the 891 subjects for which DNA was available, there were no important differences between the aggressive and moderate treatment groups as to the effect of HindIII 2/2 upon responsiveness to statin treatment, as described below.

Example 11
Characteristics of the HindIII 2/2 Genotype Group

To investigate potential mechanisms for the association between the LPL HindIII 2/2 genotype and graft worsening, baseline characteristics and response of the subjects to the lipid-lowering action of lovastatin were compared between subjects (Table 3). There were no differences observed between the baseline values for total cholesterol, HDL-cholesterol, and triglycerides. However, a small difference in LDL-cholesterol was observed, 159.6±2.1 mg/dl for subjects with HindIII 2/2 compared with 155.0±0.7 for 1/1 and 1/2, p=0.04. There were no differences in any of the lipid values attained as a result of drug treatment during the trial, nor was the amount of drug necessary to achieve target lipid values significantly different between the two genotype groups. In contrast to the essentially similar lipid profile of the LPL HindIII genotype groups, the HindIII 2/2 subjects did vary consistently on one set of physiologic parameters. They had a higher average blood pressure, systolic pressure 138.6±2.1 mmHg vs. 133.7±0.6 for subjects with other genotypes, p=0.03; and diastolic pressure 82.1±1.0 mmHg vs. 79.4±0.3 for subjects with other genotypes, p=0.02.

Multiple regression analysis showed that graft worsening or stenosis was associated with an interaction between the LPL genotype and blood pressure. The LPL HindIII 2/2 effect on blood pressure observed here probably has little effect in normal subjects. However, in the presence of ongoing vascular pathology or clinical atherosclerosis, a modest change due to a genetic factor might exert a greater effect. For example, while a blood pressure increase within the normal range has little effect in the general population, slight increases in blood pressure are a significant risk factor for nephropathy in type I diabetes, such that blood-pressure lowering intervention is recommended for some normotensive type I diabetic subjects. (J. Barzilay et al., Predisposition to hypertension: risk factor for nephropathy and hypertension in IDDM, Kidney Int. 42:723–30 [1992]; E. J. Lewis et al., The effect of angiotensin-converting enzyme inhibition on diabetic nephropathy, N. Engl. J. Med. 329:1456–62 [1993]). Thus, for those patients with an unfavorable LPL genotype (e.g., HindIII 2/2) other therapies may be indicated in addition to or instead of lipid-lowering statin treatment for prevention of atherosclerotic stenosis.

TABLE 3

Characteristics of Subjects with HindIII 2/2 Genotype

| | LPL HindIII Genotype | |
| --- | --- | --- |
| Characteristic | 2/2 (N = 74) | 1/1 & 1/2 (N = 817) |
| Age (yr, mean(SE) | 62.2 ± 0.8 | 61.7 ± 0.3 |
| Caucasian (%) | 97 | 94 |
| Male (%) | 92 | 92 |
| Current smoking (%) | 15 | 9 |
| Body mass index (kg/m², mean(SE) | 26.7 ± 0.4 | 27.3 ± 0.2 |
| History of myocardial infarction (%) | 47 | 46 |
| Time between CABG and enrollment (yr, mean(SE) | 5.0 ± 0.3 | 4.7 ± 0.1 |
| Ejection fraction (%) | 57 | 57 |

TABLE 3-continued

Characteristics of Subjects with HindIII 2/2 Genotype

| | LPL HindIII Genotype | |
|---|---|---|
| Characteristic | 2/2 (N = 74) | 1/1 & 1/2 (N = 817) |
| Family history of (%): | | |
| Coronary heart disease | 76 | 70 |
| Diabetes | 36 | 33 |
| Hypertension | 58 | 56 |
| Peripheral vascular disease | 19 | 21 |
| Stroke | 41 | 45 |
| Current medications (%): | | |
| Aspirin | 82 | 79 |
| Beta-blocker | 23 | 24 |
| Calcium-channel blocker | 26 | 24 |
| Insulin or oral antidiabetic agent | 7 | 8 |
| Thiazide diuretic | 7 | 11 |
| Systolic blood pressure (mmHg, mean(SE)* | 138.6 ± 2.1 | 133.7 ± 0.6 |
| Diastolic blood pressure (mmHg, mean(SE)* | 82.1 ± 1.0 | 79.4 ± 0.3 |
| Baseline lipid levels (mg/dl): | | |
| Total cholesterol | 230.7 ± 2.7 | 226.7 ± 0.9 |
| LDL Cholesterol* | 159.6 ± 2.1 | 155.0 ± 0.7 |
| HDL cholesterol | 41.0 ± 1.1 | 39.3 ± 0.3 |
| Triglycerides | 150.8 ± 7.3 | 161.7 ± 2.4 |
| Steady state lipid levels (mg/dl):† | | |
| Total cholesterol | 191.1 ± 4.8 | 191.0 ± 1.3 |
| LDL cholesterol | 115.1 ± 4.3 | 114.7 ± 1.1 |
| HDL cholesterol | 46.7 ± 1.6 | 44.1 ± 0.4 |
| Triglycerides | 151.0 ± 9.6 | 163.6 ± 3.4 |
| Lipid change (%): | | |
| Total cholesterol | 16.9 ± 2.0 | 15.2 ± 0.6 |
| LDL cholesterol | 53.5 ± 6.9 | 45.1 ± 1.5 |
| HDL cholesterol | 14.1 ± 3.1 | 14.2 ± 1.0 |
| Triglycerides | 6.0 ± 5.8 | 8.2 ± 2.0 |
| Mean lovastatin dose required to reach target lipid levels (mg/day): | | |
| Aggressive treatment group | 37 | 36 |
| Moderate treatment group | 6.0 | 6.5 |

LPL HindIII genotype groups were compared by the analysis of variance.
Blank p values were nonsignificant.
For the LPL HindIII genotype, "1" indicates the presence, "2" the absence, of the restriction site in intron 8.
*p-value less than 0.05.
For the difference between the systolic blood pressures, p = 0.03, for the difference between the diastolic blood pressures, p = 0.02, for the difference between the LDL cholesterol levels, p = 0.04.
†Values listed are those measured most recently before enrollment.
To convert cholesterol values to mmol/l, multiply by 0.02586; to convert triglyceride values to mmol/l, multiply by 0.01129.

Example 12
HindIII 2/2 Genotype and Statin Drug Treatment

The percent of subjects with graft worsening when stratified by lovastatin treatment group and LPL HindIII genotype is shown in FIG. 2. Complete LPL HindIII genotype data and worsening data were available for 786 subjects.

The highest percentage of subjects with worsening were those with the HindIII 2/2 genotype assigned to the moderate lipid-lowering treatment group (65%). The lowest percentage of subjects with worsening were those with the HindIII 1/1 or 1/2 genotype assigned to the aggressive lipid-lowering treatment group (35%). Within the LPL HindIII 1/1 and 1/2 genotype group, the moderate drug treatment group had a significantly higher percent of subjects with graft worsening than the aggressive treatment group, 49% compared with 35%, odds ratio=1.8, 95% confidence interval 1.3 to 2.4, p<0.001. Within the aggressive treatment group, the LPL HindIII 2/2 genotype group had a significantly higher percent of subjects with graft worsening, 54% vs. 35%; OR=2.14, 95% CI 1.11–4.11, p=0.023. The effect of genotype on graft worsening, adjusted for treatment, was significant at p=0.006, OR=2.06, 95% CI 1.23–3.43, and the effect of treatment on graft worsening, adjusted for genotype was significant at p=0.001, OR=1.78, 95% CI 1.32–2.4. The combined effect of both the unfavorable LPL HindIII genotype with moderate drug treatment yielded an odds ratio of 3.5 for graft worsening, 95% CI 1.4–8.7, p=0.002.

Using the proportion of grafts with worsening per subject as the dependent variable, the interactions between factors were tested using multiple regression analysis. After adjustments were made for age, sex, body mass index (BMI), smoking, current medication usage, medical history, and family history, the drug treatment group (p=0.000 1) and the interaction between the LPL HindIII 2/2 genotype and diastolic blood pressure (p=0.0046) remained significant. No interaction between the dose of lovastatin required to bring each subject to their target LDL-cholesterol level and the HindIII 2/2 genotype was observed.

When subjects were stratified by their LPL HindIII genotype and drug treatment group, each factor had a similar effect on graft worsening, with odds ratios of 2.1 and 1.8 respectively. The combined effect of both the unfavorable LPL HindIII genotype and moderate lipid-lowering yielded an odds ratio for graft worsening of 3.5 (95% CI 1.4–8.7, p=0.002). This analysis demonstrates that the LPL HindIII 2/2 genotype is an independent and additive risk factor for worsening of grafts with an odds ratio of the same magnitude as that for lipid-lowering in the post-CABG trial.

The foregoing examples being illustrative but not an exhaustive description of the embodiments of the present invention, the following claims are presented.

---

We claim:

1. A method of detecting a genetic predisposition in a human subject for non-responsiveness to treatment with a statin drug selected from the group consisting of lovastatin, pravastatin, and simvastatin, comprising:
  a) collecting a tissue sample from a human subject;
  b) amplifying nucleic acids that include the normal locus of the HindIII recognition site in intron 8 of the human lipoprotein lipase gene (LPL) from said tissue sample to obtain amplification products; and
  c) analyzing the amplification products for the absence of a HindIII recognition site in intron 8 of the human lipoprotein lipase gene, homozygosity for an absence of said HindIII recognition site indicating a genetic predisposition for non-responsiveness to treatment with a statin drug selected from the group consisting of lovastatin, pravastatin, and simvastatin.

2. The method of claim 1, wherein the tissue sample is a blood sample.

3. The method of claim 1, further comprising restricting the amplification products with a restriction enzyme before analyzing the amplification products.

4. The method of claim 1, wherein the restriction enzyme is HindIII.

5. The method of claim 1, wherein an oligonucleotide primer is used in amplifying said nucleic acids.

6. The method of claim 1, wherein an oligonucleotide primer comprising the sequence GCA TCT GCC TTC AGC TAG ACA TTG (SEQ. ID. NO. 1) is used in amplifying said nucleic acids.

7. The method of claim 1, wherein an oligonucleotide primer comprising the sequence TCT TCC AGA AGG GTG AGA TTC CAA (SEQ. ID. NO. 2) is used in amplifying said nucleic acids.

8. The method of claim 1, wherein an oligonucleotide primer having the sequence GCA TCT GCC TTC AGC TAG ACA TTG (SEQ. ID. NO. 1) or TCT TCC AGA AGG GTG AGA TTC CAA (SEQ. ID. NO. 2) is used in amplifying said nucleic acids.

9. The method of claim 1, wherein a reverse oligonucleotide primer having the sequence 5'-GCA TCT GCC TTC AGC TAG ACA TTG-3' (SEQ. ID. NO. 1) and a forward oligonucleotide primer having the sequence 5'-TCT TCC AGA AGG GTG AGA TTC CAA-3' (SEQ. ID. NO. 2) are used in amplifying said nucleic acids.

10. The method of claim 1, wherein an oligonucleotide primer is used in amplifying said nucleic acids, said primer comprising a sequence selected from the group essentially consisting of (SEQ. ID. NO.:1), (SEQ. ID. NO.:2), (SEQ. ID. NO.:3), (SEQ. ID. NO.:4), (SEQ. ID. NO.:5), (SEQ. ID. NO.:6), (SEQ. ID. NO.:7), (SEQ. ID. NO.:8), (SEQ. ID. NO.:9), (SEQ. ID. NO.:10), (SEQ. ID. NO.:10), (SEQ. ID. NO.:11), (SEQ. ID. NO.:12), (SEQ. ID. NO.:13), (SEQ. ID. NO.:14), (SEQ. ID. NO.:15), (SEQ. ID. NO.:16), (SEQ. ID. NO.:17), (SEQ. ID. NO.:18), (SEQ. ID. NO.:19), (SEQ. ID. NO.:20), (SEQ. ID. NO.:21), (SEQ. ID. NO.:22), (SEQ. ID. NO.:23), (SEQ. ID. NO.:24), (SEQ. ID. NO.:25), (SEQ. ID. NO.:26), (SEQ. ID. NO.:27), (SEQ. ID. NO.:28), (SEQ. ID. NO.:29), (SEQ. ID. NO.:30), (SEQ. ID. NO.:31), (SEQ. ID. NO.:32), (SEQ. ID. NO.:35), (SEQ. ID. NO.:36), (SEQ. ID. NO.:37), (SEQ. ID. NO.:38), (SEQ. ID. NO.:39), (SEQ. ID. NO.:40), (SEQ. ID. NO.:41), (SEQ. ID. NO.:42), (SEQ. ID. NO.:43), (SEQ. ID. NO.:44), (SEQ. ID. NO.:45),(SEQ. ID. NO.:46), (SEQ. ID. NO.:47), (SEQ. ID. NO.:48), (SEQ. ID. NO.:49), (SEQ. ID. NO.:50), (SEQ. ID. NO.:51), (SEQ. ID. NO.:52), (SEQ. ID. NO.:53), (SEQ. ID. NO.:54), (SEQ. ID. NO.:55), (SEQ. ID. NO.:56), (SEQ. ID. NO.:57), (SEQ. ID. NO.:58), (SEQ. ID. NO.:59), (SEQ. ID. NO.:60), (SEQ. ID. NO.:61), (SEQ. ID. NO.:62), (SEQ. ID. NO.:63), (SEQ. ID. NO.:64), (SEQ. ID. NO.:65), (SEQ. ID. NO.:66), (SEQ. ID. NO.:67), (SEQ. ID. NO.:68), (SEQ. ID. NO.:69), (SEQ. ID. NO.:70), (SEQ. ID. NO.:71), (SEQ. ID. NO.:72), (SEQ. ID. NO.:73), (SEQ. ID. NO.:74), (SEQ. ID. NO.:75), (SEQ. ID. NO.:76), (SEQ. ID. NO.:77), (SEQ. ID. NO.:78), or (SEQ. ID. NO.:79), or comprising a sequence overlapping the sequence of any of these with respect to its position on the Nickerson reference sequence.

11. The method of claim 5, wherein said oligonucleotide primer is labeled with a fluorescent dye.

12. The method of claim 11, wherein said dye is SYBR Green I, YO-PRO-1, thiazole orange, Hex, pico green, edans, fluorescein, FAM, or TET.

13. A method of detecting a genetic predisposition for non-responsiveness to lovastatin, pravastatin, or simvastatin treatment in a human subject with coronary artery disease, comprising:
  a) collecting a tissue sample from a human subject;
  b) amplifying nucleic acids comprising the HindIII restriction site in intron 8 of the human lipoprotein lipase gene (LPL) from said tissue sample to obtain amplification products; and
  c) analyzing the amplification products for the absence of a HindIII recognition site in intron 8 of the human lipoprotein lipase gene, homozygosity for an absence of said HindIII recognition site indicating a genetic predisposition in said human subject for non-responsiveness to lovastatin, pravastatin, or simvastatin treatment for coronary artery disease.

14. The method of claim 13, wherein the tissue sample is a blood sample.

15. The method of claim 13, further comprising restricting the amplification products with a restriction enzyme before analyzing the amplification products.

16. The method of claim 13, wherein the restriction enzyme is HindIII.

17. The method of claim 13, wherein an oligonucleotide primer is used in amplifying said nucleic acids.

18. The method of claim 13, comprising the sequence GCA TCT GCC TTC AGC TAG ACA TTG (SEQ. ID. NO. 1) is used in amplifying said nucleic acids.

19. The method of claim 13, wherein an oligonucleotide primer comprising the sequence TCT TCC AGA AGG GTG AGA TTC CAA (SEQ. ID. NO. 2) is used in amplifying said nucleic acids.

20. The method of claim 13, wherein an oligonucleotide primer having the sequence GCA TCT GCC TTC AGC TAG ACA TTG (SEQ. ID. NO. 1) or TCT TCC AGA AGG GTG AGA TTC CAA (SEQ. ID. NO. 2) is used in amplifying said nucleic acids.

21. The method of claim 13, wherein a reverse oligonucleotide primer having the sequence 5'-GCA TCT GCC TTC AGC TAG ACA TTG-3' (SEQ. ID. NO. 1) and a forward oligonucleotide primer having the sequence 5'-TCT TCC AGA AGG GTG AGA TTC CAA-3' (SEQ. ID. NO. 2) are used in amplifying said nucleic acids.

22. The method of claim 13, wherein an oligonucleotide primer is used in amplifying said nucleic acids, said primer comprising a nucleotide sequence of (SEQ. ID. NO.:1), (SEQ. ID. NO.:2), (SEQ. ID. NO.:3), (SEQ. ID. NO.:4), (SEQ. ID. NO.:5), (SEQ. ID. NO.:6), (SEQ. ID. NO.:7), (SEQ. ID. NO.:8), (SEQ. ID. NO.:9), (SEQ. ID. NO.:10), (SEQ. ID. NO.:11), (SEQ. ID. NO.:12), (SEQ. ID. NO.:13), (SEQ. ID. NO.:14), (SEQ. ID. NO.:15), (SEQ. ID. NO.:16), (SEQ. ID. NO.:17), (SEQ. ID. NO.:18), (SEQ. ID. NO.:19), (SEQ. ID. NO.:20), (SEQ. ID. NO.:21), (SEQ. ID. NO.22), (SEQ. ID. NO.:23), (SEQ. ID. NO.:24), (SEQ. ID. NO.:25), (SEQ. ID. NO.:26), (SEQ. ID. NO.27), (SEQ. ID. NO.:28), (SEQ. ID. NO.:29), (SEQ. ID. NO.:30), (SEQ. ID. NO.:31), (SEQ. ID. NO.:32), (SEQ. ID. NO.:35), (SEQ. ID. NO.:36), (SEQ. ID. NO.:37), (SEQ. ID. NO.:38), (SEQ. ID. NO.:39), (SEQ. ID. NO.:40), (SEQ. ID. NO.:41), (SEQ. ID. NO.:42), (SEQ. ID. NO.:43), (SEQ. ID. NO.:44), (SEQ. ID. NO.:45), (SEQ. ID. NO.:46), (SEQ. ID. NO.:47), (SEQ. ID. NO.:48), (SEQ. ID. NO.:49), (SEQ. ID. NO.:50), (SEQ. ID. NO.:51), (SEQ. ID. NO.:52), (SEQ. ID. NO.:53), (SEQ. ID. NO.:54), (SEQ. ID. NO.:55), (SEQ. ID. NO.:56), (SEQ. ID. NO.:57), (SEQ. ID. NO.:58), (SEQ. ID. NO.:59), (SEQ. ID. NO.:60), (SEQ. ID. NO.:61), (SEQ. ID. NO.:62), (SEQ. ID. NO.:63), (SEQ. ID. NO.:64), (SEQ. ID. NO.:65), (SEQ. ID. NO.:66), (SEQ. ID. NO.:67), (SEQ. ID. NO.:68), (SEQ. ID. NO.:69), (SEQ. ID. NO.:70), (SEQ. ID. NO.:71), (SEQ. ID. NO.:72), (SEQ. ID. NO.:73), (SEQ. ID. NO.:74), (SEQ. ID. NO.:75), (SEQ. ID. NO.:76), (SEQ. ID. NO.:77), (SEQ. ID. NO.:78), or (SEQ. ID. NO.:79), or comprising a sequence overlapping the sequence of any of these with respect to its position on the Nickerson reference sequence.

23. The method of claim 13, wherein said oligonucleotide primer is labeled with a fluorescent dye.

24. The method of claim 23, wherein said dye is SYBR Green I, YO-PRO-1, thiazole orange, Hex, pico green, edans, fluorescein, FAM, or TET.

25. The method of claim 13, wherein said human subject is a coronary artery bypass graft patient.

26. A method of detecting genetic predisposition in a CABG patient for non-responsiveness to treatment with a statin drug selected from the group consisting of lovastatin, pravastatin, and simvastatin, comprising:
   a) collecting a tissue sample from a CABG patient;
   b) amplifying nucleic acids comprising the locus of the HindIII recognition site in intron 8 of the human lipoprotein lipase (LPL) gene from said blood sample to obtain amplification products; and
   c) analyzing the amplification products for the absence of the HindIII recognition site in intron 8 of the human lipoprotein lipase gene, homozygosity for an absence of said HindIII recognition site indicating a genetic predisposition in said CABG patient for non-responsiveness to treatment for coronary artery disease with a statin drug selected from the group consisting of lovastatin, pravastatin, and simvastatin.

27. The method of claim 26, wherein said tissue sample is a blood sample.

28. The method of claim 26, further comprising restricting the amplification products with a restriction enzyme before analyzing the amplification products.

29. The method of claim 28, wherein the restriction enzyme is HindIII.

30. The method of claim 26, wherein an oligonucleotide primer is used in amplifying said nucleic acids.

31. The method of claim 26, comprising the sequence GCA TCT GCC TTC AGC TAG ACA TTG (SEQ. ID. NO. 1) is used in amplifying said nucleic acids.

32. The method of claim 26, wherein an oligonucleotide primer comprising the sequence TCT TCC AGA AGG GTG AGA TTC CAA (SEQ. ID. NO. 2) is used in amplifying said nucleic acids.

33. The method of claim 26, wherein an oligonucleotide primer having the sequence GCA TCT GCC TTC AGC TAG ACA TTG (SEQ. ID. NO. 1) or TCT TCC AGA AGG GTG AGA TTC CAA (SEQ. ID. NO. 2) is used in amplifying said nucleic acids.

34. The method of claim 26, wherein a reverse oligonucleotide primer having the sequence 5'-GCA TCT GCC TTC AGC TAG ACA TTG-3' (SEQ. ID. NO. 1) and a forward oligonucleotide primer having the sequence 5'-TCT TCC AGA AGG GTG AGA TTC CAA-3' (SEQ. ID. NO. 2) are used in amplifying said nucleic acids.

35. The method of claim 26, wherein an oligonucleotide primer is used in amplifying said nucleic acids, said primer comprising a sequence of (SEQ. ID. NO.:1), (SEQ. ID. NO.:2), (SEQ. ID. NO.:3), (SEQ. ID. NO.:4), (SEQ. ID. NO.:5), (SEQ. ID. NO.:6), (SEQ. ID. NO.:7), (SEQ. ID. NO.:8), (SEQ. ID. NO.:9), (SEQ. ID. NO.:10), (SEQ. ID. NO.:11), (SEQ. ID. NO.:12), (SEQ. ID. NO.:13), (SEQ. ID. NO.:14), (SEQ. ID. NO.:15), (SEQ. ID. NO.:16), (SEQ. ID. NO.:17), (SEQ. ID. NO.:18), (SEQ. ID. NO.:19), (SEQ. ID. NO.:20), (SEQ. ID. NO.:21), (SEQ. ID. NO.:22), (SEQ. ID. NO.:23), (SEQ. ID. NO.:24), (SEQ. ID. NO.:25), (SEQ. ID. NO.:26), (SEQ. ID. NO.:27), (SEQ. ID. NO.:28), (SEQ. ID. NO.:29), (SEQ. ID. NO.:30), (SEQ. ID. NO.:31), (SEQ. ID. NO.:32), (SEQ. ID. NO.:35), (SEQ. ID. NO.:36), (SEQ. ID. NO.:37), (SEQ. ID. NO.:38), (SEQ. ID. NO.:39), (SEQ. ID. NO.:40), (SEQ. ID. NO.:41), (SEQ. ID. NO.:42), (SEQ. ID. NO.:43), (SEQ. ID. NO.:44), (SEQ. ID. NO.:45),(SEQ. ID. NO.:46), (SEQ. ID. NO.:47), (SEQ. ID. NO.:48), (SEQ. ID. NO.:49), (SEQ. ID. NO.:50), (SEQ. ID. NO.:51), (SEQ. ID. NO.:52), (SEQ. ID. NO.:53), (SEQ. ID. NO.:54), (SEQ. ID. NO.:55), (SEQ. ID. NO.:56), (SEQ. ID. NO.:57), (SEQ. ID. NO.:58), (SEQ. ID. NO.:59), (SEQ. ID. NO.:60), (SEQ. ID. NO.:61), (SEQ. ID. NO.:62), (SEQ. ID. NO.:63), (SEQ. ID. NO.:64), (SEQ. ID. NO.:65), (SEQ. ID. NO.:66), (SEQ. ID. NO.:67), (SEQ. ID. NO.:68), (SEQ. ID. NO.:69), (SEQ. ID. NO.:70), (SEQ. ID. NO.:71), (SEQ. ID. NO.:72), (SEQ. ID. NO.:73), (SEQ. ID. NO.:74), (SEQ. ID. NO.:75), (SEQ. ID. NO.:76), (SEQ. ID. NO.:77), (SEQ. ID. NO.:78), or (SEQ. ID. NO.:79), or comprising a sequence overlapping the sequence of any of these with respect to its position on the Nickerson reference sequence.

36. The method of claim 30, wherein said oligonucleotide primer is labeled with a fluorescent dye.

37. The method of claim 36, wherein said dye is SYBR Green I, YO-PRO-1, thiazole orange, Hex, pico green, edans, fluorescein, FAM, or TET.

38. A method of detecting genetic predisposition in a CABG for non-responsiveness to treatment with lovastatin, pravastatin, or simvastatin, comprising:

a) collecting a tissue sample from a CABG patient, b) amplifying nucleic acids comprising the normal locus of the HindIII recognition site in intron 8 of the human lipoprotein lipase (LPL) gene from said blood sample to obtain amplification products, by using a reverse oligonucleotide primer having the sequence 5'-GCA TCT GCC TTC AGC TAG ACA TTG-3' (SEQ. ID. NO. 1) and a forward oligonucleotide primer having the sequence 5'-TCT TCC AGA AGG GTG AGA TTC CAA-3' (SEQ. ID. NO. 2); and c) analyzing the amplification products for the absence of the HindIII recognition site in intron 8 of the human lipoprotein lipase gene, homozygosity for an absence of said HindIII recognition site indicating a genetic predisposition in said CABG patient for non-responsiveness to treatment for coronary artery disease with lovastatin, pravastatin, or simvastatin.

39. The method of claim 38, wherein said tissue sample is a blood sample.

40. The method of claim 38, wherein said oligonucleotide primer is labeled with a fluorescent dye.

41. The method of claim 40, wherein said dye is SYBR Green I, YO-PRO-1, thiazole orange, Hex, pico green, edans, fluorescein, FAM, or TET.

42. A method of detecting in a human subject a genetic predisposition for non-responsiveness to treatment for coronary artery disease with a statin drug selected from the group consisting of lovastatin, pravastatin, or simvastatin, said method comprising:

a) collecting a tissue sample from a human subject;

b) amplifying nucleic acids comprising the normal locus of the HindIII recognition site in intron 8 of the human lipoprotein lipase (LPL) gene from said blood sample to obtain amplification products, by using a reverse oligonucleotide primer having the sequence 5'-GCA TCT GCC TTC AGC TAG ACA TTG-3' (SEQ. ID. NO. 1) and a forward oligonucleotide primer having the sequence 5'-TCT TCC AGA AGG GTG AGA TTC CAA-3' (SEQ. ID. NO. 2);

c) restricting said amplification products with HindIII; and d) analyzing the restriction fragments for the absence of the HindIII recognition site in intron 8 of the human lipoprotein lipase gene, wherein homozygosity for an absence of said HindIII recognition site indicates a genetic predisposition for non-responsiveness to treatment for coronary artery disease with a statin drug selected from the group consisting of lovastatin, pravastatin, or simvastatin.

43. The method of claim 42, wherein the tissue sample is a blood sample.

44. The method of claim 42, wherein said oligonucleotide primer is labeled with a fluorescent dye.

45. The method of claim 42, wherein said dye is SYBR Green I, YO-PRO-1, thiazole orange, Hex, pico green, edans, fluorescein, FAM, or TET.

46. A method of detecting a genetic predisposition in a human subject for non-responsiveness to treatment with a statin drug selected from the group consisting of lovastatin, pravastatin, or simvastatin, said method comprising:

a) collecting a tissue sample from a human subject;

b) amplifying nucleic acids comprising the normal locus of the $(TTTA)_n$ tetranucleotide repeat sequence in intron 6 of the human lipoprotein lipase gene (LPL) from said tissue sample to obtain amplification products; and c) analyzing the amplification products for $(TTTA)_n$ tetranucleotide repeat alleles present in said nucleic acids, homozygosity for a $(TTTA)_n$ 4 allele indicating a genetic predisposition for non-responsiveness to treatment for coronary artery disease with a statin drug selected from the group consisting of lovastatin, pravastatin, or simvastatin.

47. The method of claim 46, wherein the tissue sample is a blood sample.

48. The method of claim 46, wherein an oligonucleotide primer is used in amplifying said nucleic acids.

49. The method of claim 46, comprising the sequence 5'-CCT GGG TAA CTG AGC GAG ACT GTG TC-3' (SEQ. ID. NO.:33) is used in amplifying said nucleic acids.

50. The method of claim 46, wherein an oligonucleotide primer comprising the sequence 5'- ATC TGA CCA AGG ATA GTG GGA TAT A-3' (SEQ. ID. NO.:34) is used in amplifying said nucleic acids.

51. The method of claim 46, wherein an oligonucleotide primer having the sequence 5'-CCT GGG TAA CTG AGC GAG ACT GTG TC-3' (SEQ. ID. NO.:33) or 5'-ATC TGA CCA AGG ATA GTG GGA TAT A-3' (SEQ. ID. NO.:34) is used in amplifying said nucleic acids.

52. The method of claim 46, wherein a reverse oligonucleotide primer having the sequence 5'-CCT GGG TAA CTG AGC GAG ACT GTG TC-3' (SEQ. ID. NO.:33) and a forward oligonucleotide primer having the sequence 5'-ATC TGA CCA AGG ATA GTG GGA TAT A-3' (SEQ. ID. NO.:34) are used in amplifying said nucleic acids.

53. The method of claim 46, wherein amplifying said nucleic acids is done using an oligonucleotide primer comprising a nucleotide sequence of (SEQ. ID. NO.:33), (SEQ. ID. NO.:34), (SEQ. ID. NO.:82), (SEQ. ID. NO.:83), (SEQ. ID. NO.:84), (SEQ. ID. NO.:85), (SEQ. ID. NO.:86), (SEQ. ID. NO.:87), (SEQ. ID. NO.:88), (SEQ. ID. NO.:89), (SEQ. ID. NO.:90), (SEQ. ID. NO.:91), or (SEQ. ID. NO.:92), or comprising a sequence overlapping the sequence of any of these with respect to its position on the Nickerson reference sequence.

54. The method of claim 53, wherein said oligonucleotide primer is labeled with a fluorescent dye.

55. The method of claim 54, wherein said dye is SYBR Green I, YO-PRO-1, thiazole orange, Hex, pico green, edans, fluorescein, FAM, or TET.

* * * * *

UNITED STATES PATENT AND TRADEMARK OFFICE
CERTIFICATE OF CORRECTION

| | | |
|---|---|---|
| PATENT NO. | : 6,297,014 B1 | Page 1 of 1 |
| APPLICATION NO. | : 09/347114 | |
| DATED | : October 2, 2001 | |
| INVENTOR(S) | : Kent D. Taylor et al. | |

It is certified that error appears in the above-identified patent and that said Letters Patent is hereby corrected as shown below:

Column 1, Line 4-5 under the title, please insert the following:

--GOVERNMENT LICENSE RIGHTS

The U.S. Government has a paid-up license in this invention and the right in limited circumstances to require the patent owner to license others on reasonable terms as provided for by the terms of Grant Nos. NHLB7 HL 028481 and NHLB7 HL 000030 awarded by the National Institutes of Health.--

Signed and Sealed this

Thirteenth Day of April, 2010

David J. Kappos
*Director of the United States Patent and Trademark Office*

SEQUENCE LISTING

<160> NUMBER OF SEQ ID NOS: 110

<210> SEQ ID NO 1
<211> LENGTH: 24
<212> TYPE: DNA
<213> ORGANISM: Homo sapiens

<400> SEQUENCE: 1
gcatctgcct tcagctagac attg    24

<210> SEQ ID NO 2

-continued

```
<211> LENGTH: 24
<212> TYPE: DNA
<213> ORGANISM: Homo sapiens

<400> SEQUENCE: 2
tcttccagaa gggtgagatt ccaa                                            24

<210> SEQ ID NO 3
<211> LENGTH: 21
<212> TYPE: DNA
<213> ORGANISM: Homo sapiens

<400> SEQUENCE: 3
ggaaaacata agccctgaat c                                               21

<210> SEQ ID NO 4
<211> LENGTH: 21
<212> TYPE: DNA
<213> ORGANISM: Homo sapiens

<400> SEQUENCE: 4
gaaaacataa gccctgaatc g                                               21

<210> SEQ ID NO 5
<211> LENGTH: 21
<212> TYPE: DNA
<213> ORGANISM: Homo sapiens

<400> SEQUENCE: 5
aacataagcc ctgaatcgct c                                               21

<210> SEQ ID NO 6
<211> LENGTH: 21
<212> TYPE: DNA
<213> ORGANISM: Homo sapiens

<400> SEQUENCE: 6
cctgaatcgc tcacagttat t                                               21

<210> SEQ ID NO 7
<211> LENGTH: 21
<212> TYPE: DNA
<213> ORGANISM: Homo sapiens

<400> SEQUENCE: 7
ctgaatcgct cacagttatt c                                               21

<210> SEQ ID NO 8
<211> LENGTH: 21
<212> TYPE: DNA
<213> ORGANISM: Homo sapiens

<400> SEQUENCE: 8
aatcgctcac agttattcag t                                               21

<210> SEQ ID NO 9
<211> LENGTH: 21
<212> TYPE: DNA
<213> ORGANISM: Homo sapiens

<400> SEQUENCE: 9
ttggcactgt tcttgtaagt t                                               21
```

-continued

<210> SEQ ID NO 10
<211> LENGTH: 21
<212> TYPE: DNA
<213> ORGANISM: Homo sapiens

<400> SEQUENCE: 10
cactatagtt tgcaaaatcc c                                          21

<210> SEQ ID NO 11
<211> LENGTH: 24
<212> TYPE: DNA
<213> ORGANISM: Homo sapiens

<400> SEQUENCE: 11
caaacctccg agatgctacc tgga                                       24

<210> SEQ ID NO 12
<211> LENGTH: 24
<212> TYPE: DNA
<213> ORGANISM: Homo sapiens

<400> SEQUENCE: 12
agatgctacc tggataatca aaga                                       24

<210> SEQ ID NO 13
<211> LENGTH: 24
<212> TYPE: DNA
<213> ORGANISM: Homo sapiens

<400> SEQUENCE: 13
gatgctacct ggataatcaa agat                                       24

<210> SEQ ID NO 14
<211> LENGTH: 24
<212> TYPE: DNA
<213> ORGANISM: Homo sapiens

<400> SEQUENCE: 14
cttccagaag ggtgagattc caag                                       24

<210> SEQ ID NO 15
<211> LENGTH: 24
<212> TYPE: DNA
<213> ORGANISM: Homo sapiens

<400> SEQUENCE: 15
ccagaagggt gagattccaa gata                                       24

<210> SEQ ID NO 16
<211> LENGTH: 24
<212> TYPE: DNA
<213> ORGANISM: Homo sapiens

<400> SEQUENCE: 16
cagaagggtg agattccaag ataa                                       24

<210> SEQ ID NO 17
<211> LENGTH: 24
<212> TYPE: DNA
<213> ORGANISM: Homo sapiens

<400> SEQUENCE: 17
cccacccatg tgtacccata aaat                                       24

<210> SEQ ID NO 18
<211> LENGTH: 24
<212> TYPE: DNA
<213> ORGANISM: Homo sapiens

<400> SEQUENCE: 18
ccacccatgt gtacccataa aatg                                    24

<210> SEQ ID NO 19
<211> LENGTH: 24
<212> TYPE: DNA
<213> ORGANISM: Homo sapiens

<400> SEQUENCE: 19
cccatgtgta cccataaaat gaat                                    24

<210> SEQ ID NO 20
<211> LENGTH: 24
<212> TYPE: DNA
<213> ORGANISM: Homo sapiens

<400> SEQUENCE: 20
gtacccataa aatgaattac acag                                    24

<210> SEQ ID NO 21
<211> LENGTH: 24
<212> TYPE: DNA
<213> ORGANISM: Homo sapiens

<400> SEQUENCE: 21
cccataaaat gaattacaca gaga                                    24

<210> SEQ ID NO 22
<211> LENGTH: 24
<212> TYPE: DNA
<213> ORGANISM: Homo sapiens

<400> SEQUENCE: 22
atgaattaca cagagatcgc tata                                    24

<210> SEQ ID NO 23
<211> LENGTH: 24
<212> TYPE: DNA
<213> ORGANISM: Homo sapiens

<400> SEQUENCE: 23
acacagagat cgctatagga ttta                                    24

<210> SEQ ID NO 24
<211> LENGTH: 24
<212> TYPE: DNA
<213> ORGANISM: Homo sapiens

<400> SEQUENCE: 24
ttataacatt tccatcccca agat                                    24

<210> SEQ ID NO 25
<211> LENGTH: 24
<212> TYPE: DNA
<213> ORGANISM: Homo sapiens

<400> SEQUENCE: 25
catctgcctt cagctagaca ttgc                                    24

```
<210> SEQ ID NO 26
<211> LENGTH: 24
<212> TYPE: DNA
<213> ORGANISM: Homo sapiens

<400> SEQUENCE: 26
ctgcattaag gaattagggc atct                                          24

<210> SEQ ID NO 27
<211> LENGTH: 24
<212> TYPE: DNA
<213> ORGANISM: Homo sapiens

<400> SEQUENCE: 27
agatcaactc tgccatctct tagc                                          24

<210> SEQ ID NO 28
<211> LENGTH: 24
<212> TYPE: DNA
<213> ORGANISM: Homo sapiens

<400> SEQUENCE: 28
tcttatgtta ctgggctttc acca                                          24

<210> SEQ ID NO 29
<211> LENGTH: 24
<212> TYPE: DNA
<213> ORGANISM: Homo sapiens

<400> SEQUENCE: 29
agcctagagc agtcttatgt tact                                          24

<210> SEQ ID NO 30
<211> LENGTH: 24
<212> TYPE: DNA
<213> ORGANISM: Homo sapiens

<400> SEQUENCE: 30
cagcctagag cagtcttatg ttac                                          24

<210> SEQ ID NO 31
<211> LENGTH: 24
<212> TYPE: DNA
<213> ORGANISM: Homo sapiens

<400> SEQUENCE: 31
acagcctaga gcagtcttat gtta                                          24

<210> SEQ ID NO 32
<211> LENGTH: 24
<212> TYPE: DNA
<213> ORGANISM: Homo sapiens

<400> SEQUENCE: 32
agacagccta gagcagtctt atgt                                          24

<210> SEQ ID NO 33
<211> LENGTH: 26
<212> TYPE: DNA
<213> ORGANISM: Homo sapiens

<400> SEQUENCE: 33
```

-continued cctgggtaac tgagcgagac tgtgtc                                              26

<210> SEQ ID NO 34
<211> LENGTH: 25
<212> TYPE: DNA
<213> ORGANISM: Homo sapiens

<400> SEQUENCE: 34
atctgaccaa ggatagtggg atata                                               25

<210> SEQ ID NO 35
<211> LENGTH: 26
<212> TYPE: DNA
<213> ORGANISM: Homo sapiens

<400> SEQUENCE: 35
ctttataaca tttccatccc caagat                                              26

<210> SEQ ID NO 36
<211> LENGTH: 26
<212> TYPE: DNA
<213> ORGANISM: Homo sapiens

<400> SEQUENCE: 36
tgtacccata aaatgaatta cacaga                                              26

<210> SEQ ID NO 37
<211> LENGTH: 26
<212> TYPE: DNA
<213> ORGANISM: Homo sapiens

<400> SEQUENCE: 37
acccataaaa tgaattacac agagat                                              26

<210> SEQ ID NO 38
<211> LENGTH: 26
<212> TYPE: DNA
<213> ORGANISM: Homo sapiens

<400> SEQUENCE: 38
aaaatgaatt acacagagat cgctat                                              26

<210> SEQ ID NO 39
<211> LENGTH: 26
<212> TYPE: DNA
<213> ORGANISM: Homo sapiens

<400> SEQUENCE: 39
ttacacagag atcgctatag gattta                                              26

<210> SEQ ID NO 40
<211> LENGTH: 25
<212> TYPE: DNA
<213> ORGANISM: Homo sapiens

<400> SEQUENCE: 40
cagcctagag cagtcttatg ttact                                               25

<210> SEQ ID NO 41
<211> LENGTH: 25
<212> TYPE: DNA
<213> ORGANISM: Homo sapiens

<400> SEQUENCE: 41

```
acagcctaga gcagtcttat gttac                                            25

<210> SEQ ID NO 42
<211> LENGTH: 25
<212> TYPE: DNA
<213> ORGANISM: Homo sapiens

<400> SEQUENCE: 42
gacagcctag agcagtctta tgtta                                            25

<210> SEQ ID NO 43
<211> LENGTH: 28
<212> TYPE: DNA
<213> ORGANISM: Homo sapiens

<400> SEQUENCE: 43
ataaaatgaa ttacacagag atcgctat                                         28

<210> SEQ ID NO 44
<211> LENGTH: 26
<212> TYPE: DNA
<213> ORGANISM: Homo sapiens

<400> SEQUENCE: 44
aagattcttt ataacatttc catccc                                           26

<210> SEQ ID NO 45
<211> LENGTH: 28
<212> TYPE: DNA
<213> ORGANISM: Homo sapiens

<400> SEQUENCE: 45
aattacacag agatcgctat aggattta                                         28

<210> SEQ ID NO 46
<211> LENGTH: 26
<212> TYPE: DNA
<213> ORGANISM: Homo sapiens

<400> SEQUENCE: 46
acagcctaga gcagtcttat gttact                                           26

<210> SEQ ID NO 47
<211> LENGTH: 19
<212> TYPE: DNA
<213> ORGANISM: Homo sapiens

<400> SEQUENCE: 47
cccacccatg tgtacccat                                                   19

<210> SEQ ID NO 48
<211> LENGTH: 18
<212> TYPE: DNA
<213> ORGANISM: Homo sapiens

<400> SEQUENCE: 48
ccacccatgt gtacccat                                                    18

<210> SEQ ID NO 49
<211> LENGTH: 21
<212> TYPE: DNA
<213> ORGANISM: Homo sapiens
```

```
<400> SEQUENCE: 49
cacccatgtg tacccataaa a                                    21

<210> SEQ ID NO 50
<211> LENGTH: 20
<212> TYPE: DNA
<213> ORGANISM: Homo sapiens

<400> SEQUENCE: 50
acccatgtgt acccataaaa                                      20

<210> SEQ ID NO 51
<211> LENGTH: 22
<212> TYPE: DNA
<213> ORGANISM: Homo sapiens

<400> SEQUENCE: 51
ggctttcacc aagagatgat aa                                   22

<210> SEQ ID NO 52
<211> LENGTH: 22
<212> TYPE: DNA
<213> ORGANISM: Homo sapiens

<400> SEQUENCE: 52
gggctttcac caagagatga ta                                   22

<210> SEQ ID NO 53
<211> LENGTH: 22
<212> TYPE: DNA
<213> ORGANISM: Homo sapiens

<400> SEQUENCE: 53
tgaattacac agagatcgct at                                   22

<210> SEQ ID NO 54
<211> LENGTH: 22
<212> TYPE: DNA
<213> ORGANISM: Homo sapiens

<400> SEQUENCE: 54
acagagatcg ctataggatt ta                                   22

<210> SEQ ID NO 55
<211> LENGTH: 17
<212> TYPE: DNA
<213> ORGANISM: Homo sapiens

<400> SEQUENCE: 55
gttactgggc tttcacc                                         17

<210> SEQ ID NO 56
<211> LENGTH: 20
<212> TYPE: DNA
<213> ORGANISM: Homo sapiens

<400> SEQUENCE: 56
cttatgttac tgggctttca                                      20

<210> SEQ ID NO 57
<211> LENGTH: 20
<212> TYPE: DNA
<213> ORGANISM: Homo sapiens
```

```
<400> SEQUENCE: 57
tcttatgtta ctgggctttc                                          20

<210> SEQ ID NO 58
<211> LENGTH: 19
<212> TYPE: DNA
<213> ORGANISM: Homo sapiens

<400> SEQUENCE: 58
ccacccatgt gtacccata                                           19

<210> SEQ ID NO 59
<211> LENGTH: 18
<212> TYPE: DNA
<213> ORGANISM: Homo sapiens

<400> SEQUENCE: 59
cacccatgtg tacccata                                            18

<210> SEQ ID NO 60
<211> LENGTH: 18
<212> TYPE: DNA
<213> ORGANISM: Homo sapiens

<400> SEQUENCE: 60
acccatgtgt acccataa                                            18

<210> SEQ ID NO 61
<211> LENGTH: 18
<212> TYPE: DNA
<213> ORGANISM: Homo sapiens

<400> SEQUENCE: 61
cccatgtgta cccataaa                                            18

<210> SEQ ID NO 62
<211> LENGTH: 20
<212> TYPE: DNA
<213> ORGANISM: Homo sapiens

<400> SEQUENCE: 62
caactctgcc atctcttagc                                          20

<210> SEQ ID NO 63
<211> LENGTH: 20
<212> TYPE: DNA
<213> ORGANISM: Homo sapiens

<400> SEQUENCE: 63
tcaactctgc catctcttag                                          20

<210> SEQ ID NO 64
<211> LENGTH: 20
<212> TYPE: DNA
<213> ORGANISM: Homo sapiens

<400> SEQUENCE: 64
atcaactctg ccatctctta                                          20

<210> SEQ ID NO 65
<211> LENGTH: 18
<212> TYPE: DNA
```

```
<213> ORGANISM: Homo sapiens

<400> SEQUENCE: 65
gaaaacataa gccctgaa                                                 18

<210> SEQ ID NO 66
<211> LENGTH: 19
<212> TYPE: DNA
<213> ORGANISM: Homo sapiens

<400> SEQUENCE: 66
aaaacataag ccctgaatc                                                19

<210> SEQ ID NO 67
<211> LENGTH: 17
<212> TYPE: DNA
<213> ORGANISM: Homo sapiens

<400> SEQUENCE: 67
acataagccc tgaatcg                                                  17

<210> SEQ ID NO 68
<211> LENGTH: 17
<212> TYPE: DNA
<213> ORGANISM: Homo sapiens

<400> SEQUENCE: 68
ctgaatcgct cacagtt                                                  17

<210> SEQ ID NO 69
<211> LENGTH: 19
<212> TYPE: DNA
<213> ORGANISM: Homo sapiens

<400> SEQUENCE: 69
tgaatcgctc acagttatt                                                19

<210> SEQ ID NO 70
<211> LENGTH: 19
<212> TYPE: DNA
<213> ORGANISM: Homo sapiens

<400> SEQUENCE: 70
atcgctcaca gttattcag                                                19

<210> SEQ ID NO 71
<211> LENGTH: 19
<212> TYPE: DNA
<213> ORGANISM: Homo sapiens

<400> SEQUENCE: 71
tcgctcacag ttattcagt                                                19

<210> SEQ ID NO 72
<211> LENGTH: 19
<212> TYPE: DNA
<213> ORGANISM: Homo sapiens

<400> SEQUENCE: 72
cgctcacagt tattcagtg                                                19

<210> SEQ ID NO 73
<211> LENGTH: 20
```

```
<212> TYPE: DNA
<213> ORGANISM: Homo sapiens

<400> SEQUENCE: 73
aatcccagca catttagtat                                              20

<210> SEQ ID NO 74
<211> LENGTH: 20
<212> TYPE: DNA
<213> ORGANISM: Homo sapiens

<400> SEQUENCE: 74
actatagttt gcaaatccc                                               20

<210> SEQ ID NO 75
<211> LENGTH: 18
<212> TYPE: DNA
<213> ORGANISM: Homo sapiens

<400> SEQUENCE: 75
tgagagctgg gattagaa                                                18

<210> SEQ ID NO 76
<211> LENGTH: 19
<212> TYPE: DNA
<213> ORGANISM: Homo sapiens

<400> SEQUENCE: 76
gagagctggg attagaagt                                               19

<210> SEQ ID NO 77
<211> LENGTH: 19
<212> TYPE: DNA
<213> ORGANISM: Homo sapiens

<400> SEQUENCE: 77
agagctggga ttagaagtc                                               19

<210> SEQ ID NO 78
<211> LENGTH: 20
<212> TYPE: DNA
<213> ORGANISM: Homo sapiens

<400> SEQUENCE: 78
aatcccagca catttagtat                                              20

<210> SEQ ID NO 79
<211> LENGTH: 20
<212> TYPE: DNA
<213> ORGANISM: Homo sapiens

<400> SEQUENCE: 79
cccacccatg tgtacccata                                              20

<210> SEQ ID NO 80
<211> LENGTH: 9734
<212> TYPE: DNA
<213> ORGANISM: Homo sapiens

<400> SEQUENCE: 80
tgtaacacaa aattaaaata agtagaatta gttttcagta tttcctatat ttggaaaaca    60
atatttatat tcattttgtt tcttttagtt ttattttgg cagaactgta agcaccttca   120
```

-continued

| | |
|---|---|
| ttttctttt cttccaaagg aggagtttaa ctaccctctg acaatgtcc atctcttggg | 180 |
| atacagcctt ggagcccatg ctgctggcat tgcaggaagt ctgaccaata agaaagtcaa | 240 |
| cagaattact ggtaagaaag caatttcgtt ggtcttatca taagaggtga aaagactgtc | 300 |
| attctgagag agaatcagaa caaattttgt taaatacccca catgtgtggt gttcttccg | 360 |
| gagacatgac cagcacttga ttatctcatt gtagggctct ttattaggga taagaaaaaa | 420 |
| cacagacgct ctcactggct tactatccac tggcaatagc acagaaataa agcataatta | 480 |
| cacacaatgc ctgcagattt ctctgggaag cctgtttcct cccactctca gctctgtgtt | 540 |
| ttagtagtgt aaatgcacat cagtactagg agaaagaag aaggaccaat tccagaggcc | 600 |
| acttcgaaag aagaccgtca tctaggcaaa ggtgtggcat acacacagag agaaagaacc | 660 |
| caccactgtt tatacatctt ctcgacatat tcagaaataa tctacaaaag gaaatccagc | 720 |
| catcctgagt ggaaattgct gcataaggct agtttaagag actcaaattc attttagaag | 780 |
| gagccaagcc tcctttatg tctctctaag taaagatacc atgactgtag aataggagct | 840 |
| aataagaatc taaatagctg ccagtgcatt caaatgatga gcagtgacat gcgaatgtca | 900 |
| tacgaatgga aatttacaaa tctgtgttcc tgctttttc ccttttaagg cctcgatcca | 960 |
| gctggaccta actttgagta tgcagaagcc ccgagtcgtc tttctcctga tgatgcagat | 1020 |
| tttgtagacg tcttacacac attcaccaga gggtcccctg gtcgaagcat tggaatccag | 1080 |
| aaaccagttg ggcatgttga catttacccg aatggaggta cttttcagcc aggatgtaac | 1140 |
| attggagaag ctatccgcgt gattgcagag agaggacttg gaggtaaata ttatttagaa | 1200 |
| gcgaattaaa tgtgactctt atccttaacc cttattgacc caatgtccta ctcagtagct | 1260 |
| tcaaagtatg tagtttttcat atacacattt ggccaaatta tgtttctgaa gaattctgca | 1320 |
| atgttcagca tgaccacctt agagccaggc agacagccat tttatcttt atttactata | 1380 |
| ctgtaggcta cactgagcag tgcacttaca gtagcaagag aaaaaggtgg gattttagac | 1440 |
| aggaagactc cactgacctc aataatggca tcataaaatg ctatctggcc acatgttgtc | 1500 |
| ataccttgaa tgtagctgca aagccaatgg aaagatttta gatgttactg aacagaaga | 1560 |
| tgttaattag cataaatctt ccaaaatgtt cagaacataa tgttagctta atgttttact | 1620 |
| ttaataatgt tagcttgtgt taaatttatg atttttgttt gttttgtttttt tgagatagag | 1680 |
| tcttattcta ttgcccaagc tggggtgcag tcacacaatc acagggactt gcaatgttgc | 1740 |
| ccaggctggt ctcaaactcc tggcctcaag tgatcctcct gcctcagcct cccaaagttc | 1800 |
| tgggattgca gctgtgagcc accacgccca gtttacgatt tattttaag agccccttgc | 1860 |
| atactttata gacattggga cctacctagg atattctcgt tattttgtg cacgtaatag | 1920 |
| aacttagagc atattgttac tattttcgat tgtcctaaaa acttacaagg aattcattct | 1980 |
| tatggcattg ctgattattt ctatgttcat ttgatataaa agagtgttag taggggcaga | 2040 |
| accctcaatt gtacataata tcaatgataa aatacaattc atttaacaat taccctctta | 2100 |
| agatgtggtt tctagaaata caaattgtcc ctaacttaca gttttccaac tttacaattg | 2160 |
| ggctgtaaca ccatttaag ttgagaagca cgtgatggtt tgacttaaaa cttttgaca | 2220 |
| ttatgatggg ttttgggggt attaagtgca tttgactta cagtattttt gacttatgaa | 2280 |
| gaatttattg taaggcaagg ggcaggtata tgttctaga agcacctaga agtgttagac | 2340 |
| actttcaatg taagagaagg atgagataa caaggaaatc acacctccac cttggaggct | 2400 |
| tattacagct tcataaacat actcataaat ataagaagca caaagtcaa aaattccctg | 2460 |
| tgaacttgca actttcactc tcttgaaggt gggtgggccg ctaccaccaa gaatatctcc | 2520 |

```
tgaaataggg cctacaatca taaatgcaca ggactatatc cttgggtgat tctactctaa  2580
caccacatct cacctatttt agacatgcca aatgaaacac tctttgtgaa tttctgccga  2640
gatacaatct tggtgtctct tttttaccca gatgtggacc agctagtgaa gtgctcccac  2700
gagcgctcca ttcatctctt catcgactct ctgttgaatg aagaaaatcc aagtaaggcc  2760
tacaggtgca gttccaagga agcctttgag aaagggctct gcttgagttg tagaaagaac  2820
cgctgcaaca atctgggcta tgagatcaat aaagtcagag ccaaaagaag cagcaaaatg  2880
tacctgaaga ctcgttctca gatgccctac aaaggtaggc tggagactgt tgtaaataag  2940
gaaaccaagg agtcctattt catcatgctc actgcatcac atgtactgat tctgtccatt  3000
ggaacagaga tgatgactgg tgttactaaa ccctgagccc tggtgtttct gttgataggg  3060
ggttgcattg atccatttgt ctgaggcttc taattcccat tgtcagcaag gtcccagtgc  3120
tcagtgtggg atttgcagcc ttgctcgctg ccctcccctg taaatgtggc cattagcatg  3180
ggctaggcta tcagcacaga gctcagagct catttggaac catccacctc gggtcaacaa  3240
actataaccc ttgtgccaaa tccagcctac ttcctgcttt tgtaaatagt ttttttaaaa  3300
cttttaagtt caggggtacg tatgtaggtt tgctaaaaag gtaaacttgt gacatgggag  3360
tttgttgtcc agaatattcc atcacccagg tattaagctt agtacccatt agttactttt  3420
cctgaagctc tccctcctcc caccctctgg gaggcccag tgtctgttgt tccctctat  3480 gtgctcatgc aaagttttat taggacacag ccacacacat tcattaccat attgtcaaag  3540
gctggtttca tgccaccata acagagttga tagcccacag agcctaaaat atttactccc  3600
tggcccttta cagaatgttc acaacttaca taaaggcaag gaccatctgt cttatttatt  3660
tatttattta atttgagatg aagtctagct ttctcctagg ctggaggaga ggggcatgat  3720
cttggctcac cacaacctct gcctcccggg ttcaaatgat tcccctgcct cagcctccgg  3780
agtagctggg ataacaggca tgcaccatca tgcccagcta attttttgtat ttttagtaga  3840 gaggggggttt caccgtgttg accaggctgg tctcgaactg ctgacctcag gtgatctgcc  3900
ctccttggcc tcatctgtct ttttaaatgc aactattcct ggaaggcaag aatatctcac  3960
accttctaag atactgccat tttgccagga gttttgtttca cacttgaatt tcaagcttgg  4020
cctcttgttt agaggcagac ctaaaggaat ggtcggaaaa tgagagagga ggtcttcgga  4080
taaatccggt gagagggacc aacttcagga agggtggctt ttgtggaatc cagatggaaa  4140
cctgagggaa gggatgatat taaagaacag tggccccagg taaaacatat ggcacccatg  4200
tgtaaggtga ttcttagaat ctgtagaggt gtctttcgtg gtatagaggt tgaggcacct  4260
gtgcttcaag gaaaccttaa ctcttcaaaa tcaggcaatg cgtatgaggt aaagagagga  4320
ctgtgggacc ataatcttga agacacagac aggcttcact catccctgcc tcctgcacca  4380
gtgggttcaa ggctctgtca gtgtcccta gggcacctc accactccca gcttcttcag  4440
ctctggcctg tcctgctgcc tgcaagggtt ttgcttaatt ctcaattcaa tgtctcttca  4500
tcttttagta gctgtgggt tttgttgttg ttcttctgtt tttgcttagt atctgactac  4560 ttttaatta taaaagaga tgtatctaaa caaatagag attgttatca gaagttcaca  4620
acatttatta aaaatttttt cacctggaca agagtctaaa gcagcataaa aatatggtct  4680
gctatattct aaaccatcag tcttaagaga tctgtgtctc agcttaagag aaaatacatt  4740
taatagacag taacacaaat aagaaaaaaa tctgaccaag gatagtggga tatagaagaa  4800
aaaacattcc aagaattatt ttatttattt atttatttat ttatttattt atttatttat  4860
```

-continued

```
ttttgagaca cggtctcgct cagttaccca ggctggagtg cagcggcgca atcttaactc    4920
actgcaacct ctgctttccg gttcaagcga ttctcctgcc tcagcctcct gagtaactgg    4980
gattacaggc acccgccacc acgcccaact aatttctgta ttttcttag tagaaacagg    5040 gtttcaccat gttggccaag ctagtctcaa actcctgacc tcaggtgatt cacccaccaa    5100
ggcctcccaa agtgctggga ttacaggcat gagccaccat gcctggcctc caaaaactct    5160
tttttcctcc atcatcatgg ttctatttta gtcctgctgc cttttctttt aacctctccc    5220
caggcccatt tgctcagggt ttttggtaga gaccagagga ggggcaggga ggagatatag    5280
aagttcaact acctgcttcc agaggctgtc cctagtatag aatactttag ggctggctt    5340 tacaaggcag tccttgtggc ctcactgatg gctcaatgaa ataagttctt ttttaaaaaa    5400
aattttattt atttccatag gttattgggg gaacaggtgg tgtttggtta catgagtaag    5460
ttctttagta gtgatttgtg agattttggt gtgcccatta cggaatggaa aaatcaacga    5520 ataagttct atgatgcacc tactagacac ctaatctgca ctagatggtg ggggaattaa    5580
gagcatgggc atgatcctgt gaccggaagc ccgcttacag tcaggtgga ggacagacct    5640 actcatgaaa caaacacagt gacatatagt gacacagaag caaatgtcaa atatgcttgc    5700
tccagatgct aaggcacaag atggccaagg atggcggagt tcatggagaa agcatcatga    5760
gtgttttggc cttctgattt gatctcccta gcaccctca aagatggcta cttcctaatg    5820
ctgcttggca attcagacac atttgggttt tccctatgca taaccaca cttttctgaa    5880 agggagtaga attcaaggtc tgcattttct aggtatgaac actgtgcatg atgaagtctt    5940
tccaagccac accagtggtt ccatgtgtgt gcacttccgg tttgagtgct agtgagatac    6000
ttctgtggtt ctgaattgcc tgactatttg gggttgtgat atttttcataa agattgatca    6060 acatgttcga atttcctccc caacagtctt ccattaccaa gtaaagattc attttctgg    6120 gactgagagt gaaacccata ccaatcaggc ctttgagatt tctctgtatg caccgtggc    6180 cgagagtgag aacatcccat tcactctgtg agtagcacag ggggcggtc atcatggcac    6240 cagtccctcc cctgccataa cccttggtct gagcagcaga agcagagagc gatgcctaga    6300
aaacaagtct ttagttaaaa aaatcagaat tcaaaattg aggtctttcc tctatttgat    6360
attgagaaaa aaatgcttca aattggccat tttattttca cttactagtt atattttttt    6420
atttatcatc ttatatctgt ttatttcttt tataaagctg ctgttaaaca atataattaa    6480
actatctcaa aaggtttgac attaaagaaa atgagcaatg gtaacaggaa accactctat    6540
agatgtacat ataatatgta cagaaaatat aagtagtaag aagtccatga caaagtgtta    6600
gctctttttt tttttttttt ttttttttt tttgagatgg agtctctctc ctattgccca    6660
ggctggagtg cagtgattcg atctcagctc actgcaacct ctacctcccg agttcaaaca    6720
attcttctgt ctcagcctcc cgagtagctg ggctgcagg tgcccaccac catgcccagc    6780
taatttttgt attttagta gcgacagggt ctcaccatgt tggccaagct ggtcttgaat    6840
tcctgatctc aggtgatcca cccgcctcgg cctcccaaag tgctgggatt acaggtgtga    6900
gccaccatgc ccagcctacc ctttactact aatcaaagaa ataaagtaa ggcaacttga    6960 tacttttaca attactagat gaacaaatct ttaaaaatag ccagtgcaga caaggtggtg    7020
aagcagaaca tgcgaaccta ccatgcatca ttcacggcta gaaccctcca ggtgcggaag    7080
gtagtatttt aataactttc catagctaca aatatattt acatagaagg gagtgatttt    7140
tttctaatat ttatcctaaa gaaatagtca acaaacattt ttaaaaaaca tcaattacag    7200
tcgtacctat actagcataa attagaaacc cagtatccaa cattgaggca gtgggtaaat    7260
```

```
gaatcgtggt ttatcaagtc attaaaatca atctagcctt taaaaactat aattgtagga      7320
aacccaggaa aacatagtaa aaaatggaat ataaaatcta aagagaataa agaatagaga      7380
atcgtatgtg tgctatgatt gtagctaaat aatgttcaag tatcaacaca aattgaaaag      7440
gaatacatga aaatgaaaat tatatttctg aatgattgac ttcaggattt tcttttagaa      7500
ttgtattaaa tagttcatgt cattaggata aatgctggaa tgtggatata atttaaaata      7560
tactaaatgc catcgacctt cattttgagt tctttgttgg acattttgt gcattttaa        7620 aatatcccct aaataataaa gctatttata tttggagagg agaaaaaaaa gtgggggca       7680 gggagagctg atctctataa ctaaccaaat ttattgcttt tttgtttagg cctgaagttt      7740
ccacaaataa gacatactcc ttcctaattt acacagaggt agatattgga gaactactca     7800
tgttgaagct caaatggaag agtgattcat actttagctg gtcagactgg tggagcagtc    7860
ccggcttcgc cattcagaag atcagagtaa aagcaggaga gactcagaaa agtaattaa     7920 atgtatttt cttccttcac tttagacccc cacctgatgt caggacctag ggctgtatt      7980 tcagggcct tcacaattca gggagagctt taggaaacct tgtatttatt actgtatgat     8040
gtagattttc tttaggagtc ttcttttatt ttcttatttt tgggggggcgg gggggaagt     8100 gacagtattt ttgtatttca tgtaaggaaa acataagccc tgaatcgctc acagttattc    8160
agtgagagct gggattagaa gtcaggaatc tcagcttctc atttggcact gtttcttgta    8220
agtacaaaat agttagggaa caaacctccg agatgctacc tggataatca aagattcaaa    8280
ccaacctctt caagaagggt gagattccaa gataatctca acctgtctcc gcagccccac    8340
ccatgtgtac ccataaaatg aattacacag agatcgctat aggatttaaa gcttttatac   8400
taaatgtgct gggatttgc aaactatagt gtgctgttat tgttaattta aaaaaactct     8460
aagttaggat tgacaaatta tttctctta gtcatttgct tgtatcacca agaagcaaa      8520 caaacaaaca aaaaaaaaa gaaaaagatc ttggggatgg aaatgttata aagaatcttt     8580
tttacactag caatgtctag ctgaaggcag atgccctaat tccttaatgc agatgctaag    8640
agatggcaga gttgatcttt tatcatctct tggtgaaagc ccagtaacat aagactgctc    8700
taggctgtct gcatgcctgt ctatctaaat taactagctt ggttgctgaa caccgggtta    8760
ggctctcaaa ttaccctctg attctgatgt ggcctgagtg tgacagttaa ttattgggaa    8820
tatcaaaaca attacccagc atgatcatgt attatttaaa cagtcctgac agaactgtac    8880 cttttgtgaac agtgcttttg attgttctac atggcatatt cacatccatt ttcttccaca   8940
gggtgatctt ctgttctagg gagaaagtgt ctcatttgca gaaaggaaag gcacctgcgg   9000
tatttgtgaa atgccatgac aagtctctga ataagaagtc aggctggtga gcattctggg   9060
ctaaagctga ctgggcatcc tgagcttgca ccctaaggga ggcagcttca tgcattcctc   9120
ttcaccccat caccagcagc ttgccctgac tcatgtgatc aaagcattca atcagtcttt   9180
cttagtcctt ctgcatatgt atcaaatggg tctgttgctt tatgcaatac ttcctctttt   9240
tttctttctc ctcttgtttc tcccagcccg gaccttcaac ccaggcacac attttaggtt   9300
ttattttact ccttgaacta cccctgaatc ttcacttctc ctttttttctc tactgcgtct  9360 ctgctgactt tgcagatgcc atctgcagag catgtaacac aagtttagta gttgccgttc   9420
tggctgtggg tgcagctctt cccaggatgt attcagggaa gtaaaaagat ctcactgcat   9480
cacctgcagc cacatagttc ttgattctcc aagtgccagc atactccggg acacacagcc   9540
aacagggctg ccccaagcac ccatctcaaa accctcaaag ctgccaagca aacagaatga   9600
```

-continued

| | |
|---|---|
| gagttatagg aaactgttct ctcttctatc tccaaacaac tctgtgcctc tttcctacct | 9660 |
| gacctttagg gctaatccat gtggcagctg ttagctgcat cttccagag cgtcagtact | 9720 |
| gagaggacac taag | 9734 |

<210> SEQ ID NO 81
<211> LENGTH: 3867
<212> TYPE: DNA
<213> ORGANISM: Homo sapiens

<400> SEQUENCE: 81

| | |
|---|---|
| gaattcaagg tctgcatttt ctaggtatga acactgtgca tgatgaagtc tttccaagcc | 60 |
| acaccagtgg ttccatgtgt gtgcacttcc ggtttgagtg ctagtgagat acttctgtgg | 120 |
| ttctgaattg cctgactatt tggggttgtg atattttcat aaagattgat caacatgttc | 180 |
| gaatttcctc cccaacagtc ttccattacc aagtaaagat tcatttttct gggactgaga | 240 |
| gtgaaaccca taccaatcag gcctttgaga tttctctgta tggcaccgtg gccgagagtg | 300 |
| agaacatccc attcactctg tgagtagcac aggggggcgg tcatcatggc accagtccct | 360 |
| ctcctgccat aaccttggt ctgagcagca gaagcagaga gcgatgccta gaaaacaagt | 420 |
| ctttagttaa aaaaatcaga atttcaaaat tgaggtcttt cctctatttg atattgagaa | 480 |
| aaaaatgctt caaattggcc attttatttt cacttactag ttatattttt ttatttatca | 540 |
| tcttatatct gtttatttct tttataaagc tgctgttaaa caatataatt aaaaggtttg | 600 |
| acattaaaga aaatgagcaa tggtaacagg aaaccactct atagatgtac atataatatg | 660 |
| tacagaaaat ataagtagta agaagtccat gacaaagtgt tagctctttt ttttttttt | 720 |
| tttttttttt tttttgagat ggagtctctc tctattgccc aggctggagt gcagtgattc | 780 |
| gatctcagct cactgcaacc tctacctccc gagttcaaac aattcttctg tctcagcctc | 840 |
| ccgagtagct ggggctgcag gtgcccacca ccatgcccag ctaattttg tattttagt | 900 |
| agcgacaggg tctcaccatg ttggccaagc tggtcttgaa ttcctgatct caggtgatcc | 960 |
| acccgcctcg gcctcccaaa gtgctgggat tacaggtgtg agccaccatg cccagcctac | 1020 |
| cctttactac taatcaaaga aataaaagta aggcaacttg atacttttac aattactaga | 1080 |
| tgaacaaatc tttaaaaata gccagtgcag acaaggtggt gaagcagaac atgcgaacct | 1140 |
| accatgcatc attcacggct agaaccctcc aggtgcggaa ggtagtattt taataacttt | 1200 |
| ccatagctac aaaatattat tacatagaag ggagtgattt ttttctaata tttatcctaa | 1260 |
| agaaatagtc aacaaacatt tttaaaaaca tcaattacag tcgtacctat actagcataa | 1320 |
| attagaaacc cagtatccaa cattgaggca gtgggtaaat gaatcgtggt ttatcaagtc | 1380 |
| attaaaatca atctagcctt taaaaactat aattgtagga aacccaggaa acatagtaa | 1440 |
| aaaatggaat ataaaatctg aagagaataa agaatagaga atcgtatgtg tgctatgatt | 1500 |
| gtagctaaat aatgttcaag tatcaacaca aattgaaaag gaatacatga aaatgaaaat | 1560 |
| tatatttctg aatgattgac ttcaggattt tcttttagaa ttgtattaaa tagttcatgt | 1620 |
| cattaggata aatgctggaa tgtggatata atttaaaata tactaaatgc catcgaccttt | 1680 |
| cattttgagt tctttgttgg acattttgt gcattttaa aatatcccct aaataataaa | 1740 |
| gctatttata tttggagagg agaaaaaaaa gtgggggca gggagagctg atctctataa | 1800 |
| ctaaccaaat ttattgcttt tttgtttagg cctgaagttt ccacaaataa gacctactcc | 1860 |
| ttcctaattt acacagaggt agatattgga gaactactca tgttgaagct caaatggaag | 1920 |
| agtgattcat actttagctg gtcagactgg tggagcagtc ccggcttcgc cattcagaag | 1980 |

```
atcagagtaa aagcaggaga gactcagaaa agtaattaa atgtattttt cttccttcac    2040
tttagacccc cacctgatgt caggacctag gggctgtatt tcaggggcct tcacaattca    2100
gggagagctt taggaaacct tgtatttatt actgtatgat gtagattttc tttaggagtc    2160 ttctttatt ttcttatttt tggggggcgg gggggaagt gacagtattt ttgtatttca      2220
tgtaaggaaa acataagccc tgaatcgctc acagttattc agtgagagct gggattagaa    2280
gtcaggaatc tcagcttctc atttggcact gtttcttgta agtacaaaat agttagggaa    2340
caaacctccg agatgctacc tggataatca aagattcaaa ccaacctctt ccagaagggt    2400
gagattccaa gataatctca acctgtctcc gcagccccac ccatgtgtac ccataaaatg    2460
aattacacag agatcgctat aggatttaaa gcttttatac taaatgtgct gggattttgc    2520
aaactatagt gtgctgttat tgttaattta aaaaaactct aagttaggat tgacaaatta    2580
tttctcttta gtcatttgct tgtatcacca agaagcaaa caaacaaaca aaaaaaaaa       2640 gaaaaagatc ttggggatgg aaatgttata agaatctttt tttacactag caatgtctag    2700
ctgaaggcag atgccctaat tccttaatgc agatgctaag agatggcaga gttgatcttt    2760
tatcatctct tggtgaaagc ccagtaacat aagactgctc taggctgtct gcatgcctgt    2820
ctatctaaat taactagctt ggttgctgaa caccaggtta ggctctcaaa ttaccctctg    2880
attctgatgt ggcctgagtg tgacagttaa ttattgggaa tatcaaaaca attacccagc    2940
atgatcatgt attattaaa cagtcctgac agaactgtac ctttgtgaac agtgcttttg     3000
attgttctac atggcatatt cacatccatt ttcttccaca gggtgatctt ctgttctagg    3060
gagaaagtgt ctcatttgca gaaaggaaag gcacctgcgg tatttgtgaa atgccatgac    3120
aagtctctga ataagaagtc aggctggtga gcattctggg ctaaagctga ctgggcatcc    3180
tgagcttgca ccctaaggga ggcagcttca tgcattcctc ttcacccat caccagcagc      3240 ttgccctgac tcatgtgatc aaagcattca atcagtcttt cttagtcctt ctgcatatgt    3300
atcaaatggg tctgttgctt tatgcaatac ttcctctttt tttctttctc ctcttgtttc    3360
tcccagcccg gaccttcaac ccaggcacac attttaggtt ttatttact ccttgaacta      3420 cccctgaatc ttcacttctc cttttttctc tactgcgtct ctgctgactt tgcagatgcc    3480
atctgcagag catgtaacac aagtttagta gttgccgttc tggctgtggg tgcagctctt    3540
cccaggatgt attcagggaa gtaaaaagat ctcactgcat cacctgcagc cacatagttc    3600
ttgattctcc aagtgccagc atactccggg acacacagcc aacagggctg ccccaagcac    3660
ccattctcaa aaccctcaaa gctgccaagc aaacagaatg agagttatag gaaactgttc    3720
tctcttctat ctccaaacaa ctctgtgcct ctttcctacc tgacctttag ggctaatcca    3780
tgtggcagct gttagctgca tctttccaga gcgtcagtac tgagaggaca ctaagcatgt    3840
gaccttcact actcctgttc tgaattc                                         3867
```

<210> SEQ ID NO 82
<211> LENGTH: 24
<212> TYPE: DNA
<213> ORGANISM: Homo sapiens

<400> SEQUENCE: 82
ctggacaaga gtctaaagca gcat    24

<210> SEQ ID NO 83
<211> LENGTH: 20
<212> TYPE: DNA

-continued

<210> SEQ ID NO 84
<211> LENGTH: 24
<212> TYPE: DNA
<213> ORGANISM: Homo sapiens

<400> SEQUENCE: 83
gaatcgcttg aaccggaaag                                        20

<210> SEQ ID NO 84
<211> LENGTH: 24
<212> TYPE: DNA
<213> ORGANISM: Homo sapiens

<400> SEQUENCE: 84
accatcagtc ttaagagatc tgtg                                   24

<210> SEQ ID NO 85
<211> LENGTH: 24
<212> TYPE: DNA
<213> ORGANISM: Homo sapiens

<400> SEQUENCE: 85
cacagatctc ttaagactga tggt                                   24

<210> SEQ ID NO 86
<211> LENGTH: 20
<212> TYPE: DNA
<213> ORGANISM: Homo sapiens

<400> SEQUENCE: 86
tttttcacct ggacaagagt                                        20

<210> SEQ ID NO 87
<211> LENGTH: 20
<212> TYPE: DNA
<213> ORGANISM: Homo sapiens

<400> SEQUENCE: 87
gggtaactga gcgagaccgt                                        20

<210> SEQ ID NO 88
<211> LENGTH: 20
<212> TYPE: DNA
<213> ORGANISM: Homo sapiens

<400> SEQUENCE: 88
ttcacctgga caagagtcta                                        20

<210> SEQ ID NO 89
<211> LENGTH: 15
<212> TYPE: DNA
<213> ORGANISM: Homo sapiens

<400> SEQUENCE: 89
gcttgaaccg gaaag                                             15

<210> SEQ ID NO 90
<211> LENGTH: 20
<212> TYPE: DNA
<213> ORGANISM: Homo sapiens

<400> SEQUENCE: 90
tcacctggac aagagtctaa                                        20

<210> SEQ ID NO 91
<211> LENGTH: 17

<210> SEQ ID NO 92
<211> LENGTH: 20
<212> TYPE: DNA
<213> ORGANISM: Homo sapiens

<400> SEQUENCE: 91
ctccagcctg ggtaact                                                    17

<210> SEQ ID NO 92
<211> LENGTH: 20
<212> TYPE: DNA
<213> ORGANISM: Homo sapiens

<400> SEQUENCE: 92
acaagagtct aaagcagcat                                                 20

<210> SEQ ID NO 93
<211> LENGTH: 668
<212> TYPE: DNA
<213> ORGANISM: Homo sapiens

<400> SEQUENCE: 93
tcttttagta gctgtggggt tttgttgttg ttcttctgtt tttgcttagt atctgactac     60
tttttaatta taaaagaga tgtatctaaa caaaatagag attgttatca gaagttcaca    120
acatttatta aaaattttt cacctggaca agagtctaaa gcagcataaa aatatggtct    180
gctatattct aaaccatcag tcttaagaga tctgtgtctc agcttaagag aaaatacatt    240
taatagacag taacacaaat aagaaaaaaa tctgaccaag gatagtggga tatagaagaa    300
aaaacattcc aagaattatt ttatttattt atttatttat ttatttattt atttatttat    360
ttatttattt ttgagacacg gtctcgctca gttacccagg ctggagtgca gcggcgcaat    420
cttaactcac tgcaacctct gctttccggt tcaagcgatt ctcctgcctc agcctcctga    480
gtaactggga ttacaggcac ccgccaccac gcccaactaa tttctgtatt tttcttagta    540
gaaacagggt ttcaccatgt tggccaagct agtctcaaac tcctgacctc aggtgattca    600
cccaccaagg cctcccaaag tgctgggatt acaggcatga gccaccatgc ctggcctcca    660
aaaactct                                                            668

<210> SEQ ID NO 94
<211> LENGTH: 3240
<212> TYPE: DNA
<213> ORGANISM: Homo sapiens

<400> SEQUENCE: 94
gaattctctc taaaaataaa atgatgtatg atttgttgtt ggcatcccct ttattaattc     60
attaaatttc tggatttggg ttgtgaccca gggtgcatta acttaaaaga ttcactaaag    120
cagcacatag cactgggaac tctggctccg aaaaactttg ttatatatat caaggatgtt    180
ctggctttac attttattta ttagctgtaa atacatgtgt ggatgtgtaa atggagcttg    240
tacatattgg aaaggtcatt gtggctatct gcatttataa atgtgtggtg ctaactgtat    300
gtgtctttat cagtgatggt ctcacagagc caactcactc ttatgaaatg ggctttaaca    360
aaacaagaaa gaaacgtact taactgtgtg aagaaatgga atcagctttt aataaaattg    420
acaacatttt attaccacac taagtcatta ttttgtatca ttttttaaagt aaatttattc    480
ttaggtcaga ttcactcagc atattttgac taagtaacca ctgtacttag taaaccgaag    540
agcttctgag aattatagtg taccgtatag atatttttaa catttatatt tgtataaagc    600
taaagaaagc cttacatatc ctttaaactg actatagaag aaaatgatac agaattttgc    660

```
ctgcataaag tacacaggac tattcttgcc tacaatatgc ttttcacaa gcaaaatgtt      720 agactaatat aaggcatctt tggccatttt atagtgtaca tcatctctat ttctgaggcc      780
tcattgttag ctgtaacgca agtagcattt gtgcaataaa atgaactatt tgggatggga      840
gggtacattt tttagaactt tgctttgggt tgccttgata attaatagca tatagtccat      900
ttatgcagct aagtagggat tgcttcttag tacagtcagg aagaatttag cccagaaaac      960
aattatttca atggccactg acccaaactt ccaggctgaa gagcaatggc gtgatcatgg     1020
ctcactgcac ctccacctcc caggctcaag tgattctcct gcctcagcct cccaagtaga     1080
tggtactaca agcacacgcc actgcaccca gctaattttt gtattttttg tagagatggg     1140
ggtttcacca tgttgcccag gctggtctta aattcctggc tcaagtgtc tgcccccctt     1200 ggcctcccaa agtgctggaa ttacaggcat gagccaccat gtccagcctt gacccaaact     1260
tttattgtca gttagctatt gggggcttct ggagtttggg tctcccctga caggaggggg     1320
ctccccagtt cacacttggc cactgcccat caattcctgt tgatatgatc aacaagatag     1380
acaattgcaa atgttgctga ggatgtggag aagtgtgaac ctgtgtaagt ggctgatggg     1440
aatgtaaaat ggcacagcca ctatggagaa caatttggta gtatttccaa agttaagcat     1500
agagtttaac ccatatgacc cagcaattcc actcctagat atatacccaa gagaaatgaa     1560
aacacagatc cacaaagatt tgcacacaca ggttcatagc agcattaatc agattagtcc     1620
caaagtggac aacccaaatg tccatgaact tgtgaaagag ataagcaaaa tgtgacaaat     1680
tcacataata aatatattt cagaagtaaa agaacaagc agcagatata tgatacaaca     1740
cgatgcgcct tgaaaacgtt tagccatatg aaagaaacca gatgcaaaat ggaaccatgg     1800
cttaggggag gagaacggca caatggtgta aaagttgcag agaggaacaa aaaggctacc     1860
tgcctcgctc ccaggccaag taacacagga ggaaagaaaa tatccacata tgcgagggct     1920
aaaggaaaga ggtgttctca agctgaagca ggaggtggga ctcaactctg gaggtgggcc     1980
tcacacactg taccaaattg aggactagct aaaacaggga tgggggtgaa agcacctttt     2040
cgtaagacat gccaccatt gtcccgttct cctcccttaa gcccttgtct tgctcatgtc     2100
agcaagctta ttgccatcta ttcttcctag ttacagacat ctgtggagct ctgagttttt     2160
tgcctaatca ttattttaga acctggttca ctctctctcc cttctacact agttctgtca     2220
ttattattac tgatttcagt acctctgagg tgatagattt tattttccaa tggcagccac     2280
aacactacct cccattctat atgttcccct gcaatgttgc cttgacatcc ctattaagag     2340
ttggaatcta gtcaccccgc ttttctagtc tccccactcc tttgaacttg tgtgggccct     2400
aagattgctt ctactagtag aatagaacta aaatgaccct ggaccagtgt ggggtgcagc     2460
ccttaactgg cctggcagct tctgcttttg gttccttggg gcactcactc ttgggaaact     2520
tccctttgga actcagcatt catgatgcgg aagttgaagc cacatgaaaa gagcatatgg     2580
tggttctctc agctcccagc caacaaccag tctcgactgt cagccatgtg agtgaggcat     2640
cttggacctc cggccagttg agtgttcaga agactgcagc tcgagctggc atctggatgc     2700
aaccacatga gagacgctct gcccagccaa gcccagccaa ctcacagtac tatgagagat     2760
actaataact tgttgttgtt gttgttgttg ttgtttttat tattaaactt taagttttag     2820
catacacgtg cacaacgtgc aggttagtta catatgtata cctgggccat gttggtgtgc     2880
tgcacccagt aactcgtcat ttaacattag gtatatctcc aaatgctatc cctcccccct     2940
ccctaagttt ttaggagttt gctttgcaac gatagatagt tgaaacatct ggatgatgca     3000
tccagtattc tggcttctca ctgcctttac ctcctctctc ccatggcctt gtcttctaaa     3060
```

```
tctacctttta catagaaaca ttcagtcacg tgctatacta tatcatgcca ttactaataa      3120
ctcataaact caatttcaac ttctcccttc tttgactacc acatgctatc tttttacttt      3180
aatcagtcta gtgctctcag ttcaacagct cctcaactgc cccaggacct ccaatacatt      3240
```

<210> SEQ ID NO 95
<211> LENGTH: 22
<212> TYPE: DNA
<213> ORGANISM: Homo sapiens

<400> SEQUENCE: 95

```
atgaaaagag catatggtgg tt                                                22
```

<210> SEQ ID NO 96
<211> LENGTH: 25
<212> TYPE: DNA
<213> ORGANISM: Homo sapiens

<400> SEQUENCE: 96

```
tggcccaggt atacatatgt aacta                                             25
```

<210> SEQ ID NO 97
<211> LENGTH: 25
<212> TYPE: DNA
<213> ORGANISM: Homo sapiens

<400> SEQUENCE: 97

```
ggcccaggta tacatatgta actaa                                             25
```

<210> SEQ ID NO 98
<211> LENGTH: 22
<212> TYPE: DNA
<213> ORGANISM: Homo sapiens

<400> SEQUENCE: 98

```
tgaaaagagc atatggtggt tc                                                22
```

<210> SEQ ID NO 99
<211> LENGTH: 21
<212> TYPE: DNA
<213> ORGANISM: Homo sapiens

<400> SEQUENCE: 99

```
gaaaagagca tatggtggtt c                                                 21
```

<210> SEQ ID NO 100
<211> LENGTH: 25
<212> TYPE: DNA
<213> ORGANISM: Homo sapiens

<400> SEQUENCE: 100

```
gcccaggtat acatatgtaa ctaac                                             25
```

<210> SEQ ID NO 101
<211> LENGTH: 20
<212> TYPE: DNA
<213> ORGANISM: Homo sapiens

<400> SEQUENCE: 101

```
aaaagagcat atggtggttc                                                   20
```

<210> SEQ ID NO 102

```
<211> LENGTH: 25
<212> TYPE: DNA
<213> ORGANISM: Homo sapiens

<400> SEQUENCE: 102
ggttctctca gctcccagcc aacaa                                              25

<210> SEQ ID NO 103
<211> LENGTH: 23
<212> TYPE: DNA
<213> ORGANISM: Homo sapiens

<400> SEQUENCE: 103
agcacaccaa catggcccag gta                                                23

<210> SEQ ID NO 104
<211> LENGTH: 25
<212> TYPE: DNA
<213> ORGANISM: Homo sapiens

<400> SEQUENCE: 104
ctcagctccc agccaacaac cagtc                                              25

<210> SEQ ID NO 105
<211> LENGTH: 24
<212> TYPE: DNA
<213> ORGANISM: Homo sapiens

<400> SEQUENCE: 105
cagcacacca acatggccca ggta                                               24

<210> SEQ ID NO 106
<211> LENGTH: 25
<212> TYPE: DNA
<213> ORGANISM: Homo sapiens

<400> SEQUENCE: 106
agctcccagc caacaaccag tctcg                                              25

<210> SEQ ID NO 107
<211> LENGTH: 16
<212> TYPE: DNA
<213> ORGANISM: Homo sapiens

<400> SEQUENCE: 107
actccgggaa tgaggt                                                        16

<210> SEQ ID NO 108
<211> LENGTH: 21
<212> TYPE: DNA
<213> ORGANISM: Homo sapiens

<400> SEQUENCE: 108
ccagaaagaa gagattttgt c                                                  21

<210> SEQ ID NO 109
<211> LENGTH: 24
<212> TYPE: DNA
<213> ORGANISM: Homo sapiens

<400> SEQUENCE: 109
ctgctttaga ctcttgtcca ggtg                                               24
```

-continued

```
<210> SEQ ID NO 110
<211> LENGTH: 24
<212> TYPE: DNA
<213> ORGANISM: Homo sapiens

<400> SEQUENCE: 110
gggttcaagg ctctgtcagt gtcc                                              24
```